US005824642A

United States Patent [19]
Attie et al.

[11] Patent Number: 5,824,642
[45] Date of Patent: Oct. 20, 1998

[54] TREATMENT OF PARTIAL GROWTH HORMONE INSENSITIVITY SYNDROME

[75] Inventors: Kenneth Attie, San Francisco, Calif.; Lena M. S. Carlsson, Goteborg, Sweden; Neil Gesundheit, Los Altos; Audrey Goddard, San Francisco, both of Calif.

[73] Assignee: Genentech, Inc., South San Francisco, Calif.

[21] Appl. No.: 468,580

[22] Filed: Jun. 6, 1995

Related U.S. Application Data

[63] Continuation of Ser. No. 410,452, Mar. 24, 1995, abandoned, which is a continuation-in-part of Ser. No. 224,982, Apr. 7, 1994, Pat. No. 5,646,113.

[51] Int. Cl.⁶ .......................... C07K 13/00; A61K 38/00; A61K 38/28
[52] U.S. Cl. .............................. 514/12; 514/12; 530/303; 530/311; 530/399
[58] Field of Search ...................... 514/12, 21; 530/303, 530/311, 399

[56] References Cited

U.S. PATENT DOCUMENTS

| 5,126,324 | 6/1992 | Clark et al. | 514/12 |
| 5,187,151 | 2/1993 | Clark et al. | 514/3 |

FOREIGN PATENT DOCUMENTS

WO 91/18621  12/1991  WIPO.

OTHER PUBLICATIONS

Shimasaki and Ling, Progress in Growth Factor Research, vol. 3 pp. 243–266, 1991.
*Pediatric and Adolescent Endocrinology: Lessons from Laron Syndrome (LS) 1966–1992*, Laron et al., Basel:Karger vol. 24:1–367 (1992).
Aguirre et al., "High–Affinity Serum Growth–Hormone–Binding Protein, Absent in Laron–Type Dwarfism, is Diminished in Heterozygous Parents" *Horm. Res.* 34:4–8 (1990).
Albertson–Wikland, "Growth Hormone Treatment in Short Children—Short–Term and Long–Term Effects on Growth" *Acta Paediatr Scand Suppl.* 343:77–84 (1988).
Albertsson–Wikland et al., "Analyses of 24–Hour Growth Hormone Profiles in Children: Relation to Growth" *J. Clin. Endocrin. and Metabol.* 67(3):493–500 (1988).
Amselem et al., "Larson Dwarfism and Mutations of the Growth Hormone–Receptor Gene" *New England J. of Med.* 321(15):989–995 (1989).
Amselem et al., "Molecular Basis of Laron Dwarfism" *TEM*, Elsevier Science Publishing Co., Inc. pp. 35–40 (1991).
Amselem et al., "Molecular Defects in the Growth Hormone Receptor" *Acta Paediatr Scand [Suppl]* 377:81–86 (1991).
Amselem et al., "Spectrum of Growth Hormone Receptor Mutations and Associated Haplotypes in Laron Syndrome" *Human Molecular Genetics* 2(4):355–359 (1993).

Attie et al., "Evidence for Partial Growth Hormone (GH) Insensitivity among Idiopathic Short Stature (ISS) Patients Treated with Growth Hormone" *4th Joint LWPES/ESPE Meeting* (San Francisco) (1993).
Attie et al., "Evidence for partial growth hormone insensitivity among patients with idiopathic short stature" *J. Pediatrics* 127:244–250 (Aug. 1995).
August et al., "Growth Hormone Treatment in the United States: Demographic and Diagnostic Features of 2331 Children" *J. Pediatr.* 116(6):899–903 (1990).
Backeljauw et al., "Effects of Prolonged IGF–I Treatment in Children with Growth Hormone Insensitivity Syndrome (GHIS)" *Pediatr. Res.* 33:S56, 5 Suppl., #314 (1993).
Baumann et al., "Absence of the Plasma Growth Hormone–Binding Protein in Laron–Type Dwarfism" *J. Clin. Endocrin. and Metabol.* 65(4):814–816 (1987).
Baumann et al., "Circulating Molecular Variants of Growth Hormone in Childhood" *Pediatr. Res.* 22(1):21–22 (1987).
Baumann et al., "Short Stature and Decreased Serum Growth Hormone–Binding Protein in the Mountain Ok People of Papua New Guinea" *J. Clin. Endocrin. and Metabol.* 72(6):1346–1349 (1991).
Baumbach et al., "the Growth Hormone–Binding Protein in Rat Serum is an Alternatively Spliced Form of the Rat Growth Hormone Receptor" *Gene & Development* 3:1199–1205 (1989).
Baumgartner et al., "The Role of the WSXWS Equivalent Motif in Growth Hormone Receptor Function" *J. Biol. Chemistry* 269(46):290494–29101 (1994).
Bierich et al., "Die Spontansekretion des Wachstumshormons bei der konstittionellen Entwicklingsverzoegerung und der fruehnormalen Pubertat" *Monatsschritt fur Kinderheilkunde* (English abstract) 127:561–565 (1979).

(List continued on next page.)

*Primary Examiner*—Cecilia J. Tsang
*Assistant Examiner*—P. Lynn Touzeau
*Attorney, Agent, or Firm*—Flehr Hohbach Test Albritton & Herbert LLP; Walter H. Dreger

[57] ABSTRACT

Methods for increasing the growth rate of a human patient having partial growth hormone insensitivity syndrome, but not Laron syndrome, are described. One such method comprises administering an effective dose of growth hormone, preferably growth hormone with a native human sequence, with or without an N-terminal methionine, to the patient. The patient is characterized as having a height of less than about –2 standard deviations below normal for age and sex, a serum level of high-affinity growth hormone binding protein that is at least 2 standard deviations below normal levels, a serum level of IGF-I that is below normal mean levels, and a serum level of growth hormone that is at least normal. In another such method, the same patient population is treated with an effective amount of IGF-I, given alone or in combination with an amount of growth hormone that is effective in combination with the IGF-I.

16 Claims, 12 Drawing Sheets

OTHER PUBLICATIONS

Bjarnason et al., "Seasonal Variation in Growth Hormone Binding Protein (GHBP) Levels in Prepubertal Normal Growing Healthy Children" *The Endocrine Society 77th Annual Meeting* (Abstract P3–137) p. 500 (Jun. 1995).

Blum et al., "Clinical Studies of IGFBP–2 by Radioimmunoassay" *Growth Regulations* 3:100–104 (1993).

Blum et al., "Growth Hormone Insensitivity Syndromes: A Preliminary Report On Changes in Insulin–Like Growth Factors and Their Binding Proteins During Treatment with Recombinant Insulin–Like Growth Factor I" *Acta Paediatr Suppl* 391:15–19 (1993).

Blum et al., "Improvemant of Diagnostic Criteria in Growth Hormone Insensitivity Syndrome: Solutions and Pitfalls" *Acta Paediatr. Suppl.*, B. Lippe et al., Lisbon, Portugal vol. 399:117–124 (Presented Oct. 1993).

Bramswig et al., "Adult Height in Boys and Girls with Untreated Short Stature and Constitutional Delay of Growth–And Puberty: Accuracy of Five Different Methods of Height Prediction" *J. Pediatr.* 117:886–891 (1990).

Buchanan et al., "Laron–Type Dwarfism with Apparently Normal High Affinity Serum Growth Hormone–Binding Protein" *Clinical Endocrinology* 35:179–185 (1991).

Carlsson et al., "Analysis of 24–Hour Plasma Profiles of Growth Hormone (GH)–Binding Protein, GH/GH–Binding Protein–Complex, and GH in Healthy Children" *J. Clin. Endocrin. and Metabol.* 77(2) :356–361 (1993).

Carlsson et al., "Decreased Growth Hormone (GH)—Binding Protien and Normal Endogenous GH Secretion in Children with Idiopathic Short Stature" (The Amer. Pediatric Society/The Society for Pediatric Research) (1992).

Carlsson et al., "Ligand–Mediated Immunofunctional Assay for Quantitation of Growth Hormone–Binding Protein in Human Blood" *J. Clin. Endocrin. and Metabol.* 73(6) :1216–1223 (1991).

Carlsson et al., "Reduced Concentration of Serum Growth Hormone–Binding Protein in Children with Idiopathic Short Stature" *J. Clin. Endocrin. and Metabol.* 78(6) :1325–1330 (1994).

Chan et al., "Expression of Insulin–Like Growth Factor–1 un Uremic Rats: Growth Hormone Resistance and Nutritional Intake" *Kidney International* 43:790–795 (1993).

Chanoine et al., "Growth Hormone (GH) Treatment in Short Normal Children: Absence of Influence of Time of Injection and Resistance to GH Autofeedback" *J. Clin. Endocrin. and Metabol.* 73(6):1269–1275 (1991).

Clackson et al., "A Hot Spot of Binding Energy in a Hormone–Receptor Interface" *Science* 267:383–386 (1995).

Clemons et al., "Laron Dwarfism: Growth and Immunoreactive Insulin Following Treatment with Human Growth Hormone" *J.Pediatr.*, 88(3):427–433 (1976).

Costantino et al., "Insulin–Resistant MDA–MB231 Human Breast Cancer Cells Contain a Tyrosine Kinase Inhibiting Activity" *Molecular Endocrinology* 7(12):1667–1676 (1993).

Cotterill et al., "The Effect of Recombinant Human Insulin–Like Growth Factor–I Treatment on Growth Hormone Secretion in Two Subjects with Growth Hormone Insensitivity (Laron Syndrome)" *Clin. Endocrin.* 39:119–122 (1993).

Cowell et al., "Effects of Growth Hormone in Short, Slowly Growing Children Without Growth Hormone Deficiency" *Acta Paediatr Scand Suppl.* 366:29–30 (1990).

Crowne et al., "Final Height in Boys with Untreated Constitutional Delay in Growth and Puberty" *Archives of Disease in Childhood* 65:1109–1112 (1990).

Cunningham et al., "Growth Hormone Binding Protein Enhances the Growth Promoting Activity of GH in the Rat" *The Endocrine Society—Program and Abstracts* (73rd Annual Meeting) 1611:433 (1991).

Daughaday et al., "Absence of Serum Growth Hormone Binding Protein in Patients with Growth Hormone Receptor Deficiency (Laron Dwarfism)" *Proc. Natl. Acad. Sci. USA* 84:4636–4640 (1987).

De Vos et al., "Human Growth Hormone and Extracellular Domain of its Receptor: Crystal Structure of the Complex" *Science* 255:306–312 (1992).

Diamond et al., "Hormonal, Metabolic and Pharmacokinetic Changes in Adults with Growth Hormone Receptor Deficiency Treated with Recombinant Human Insulin–Like Growth Factor I" *Acta Paediatr Suppl.* 383:148 (1992).

Eshet et al., "Defect of Human Growth Hormone Receptors in the Liver of Two Patients with Laron–Type Dwarfism" *Is. J. Med. Sci.* 20:8–11 (1984).

Fielder et al., "Expression of Serum Insulin–Like Growth Factors, Insulin–Like Growth Factor–Binding Proteins, and the Growth Hormone–Binding Protein in Heterozygote Relatives of Equadorian Growth Hormone Receptor Deficient Patients" *J. Clin. Edocrin. and Metabol.* 74:743–750 (1992).

Fielder et al., "Serum Profiles of Insulin–Like Growth Factors and Their Binding Proteins in Adults with Growth Hormone Receptor Deficiency Treated with Insulin–Like Growth Factor I" *Acta Paediatr Suppl.* 388:40–43 (1993).

Fine et al., "Growth After Recombinant Human Growth Hormone Treatment in Children with Chronic Renal Failure: Report of a Multicenter Randomized Double–Blind Placebo–Controlled Study" *J. Pediat.* 124(3):374–382 (Mar. 1994).

Fontoura et al., "Effect of growth hormone on the low level of growth hormone binding protein in idiopathic short stature" *Clin. Endocrin.* 37:249–253 (1992).

Frasier et al., "Clinical Review 11: The Rational Use of Growth Hormone During Childhood" *J. Clin. Endocrin. and Metabol.* 71:269–273 (1990).

Gargosky et al., "The Composition and Distribution of Insulin–Like Growth Factors (IGFs) and IGF–Binding Proteins (IGFBPs) in the Serum of Growth Hormone Receptor–Deficient Patients: Effects of IGF–I Therapy on IGFBP–3" *J. Clin Endocrin. and Metabol.* 77:1683–1689 (1993).

Genentech, Inc., "Response to Growth Hormone in Children with Idiopathic Short Stature" *Acta Paediatr Scand* (Suppl.) 366:24–26 (1990).

Gillespie et al., "Enhanced Potency of Truncated Insulin–Like Growth Factor–I (des (1–3) IGF–I) Relative to IGF–I in lit/lit mice" *J. Endocrin.* 127:401–405 (1990).

Gluckman et al., "Therapeutic use of insulin–like growth factor I: lessons from in vivo animal studies" *Acta Paediatr* (Suppl.) 383:134–136 (1992).

Goddard et al., "Growth Hormone (GH) Receptor Defects are Present in Selected Children with Non–GH–Deficient Short Stature: A Molecular Basis for Partial GH–Insensitivity" *Proc. 76th Ann. Meeting of Endocrine Society* p. 204 (Jun. 1994).

Godowski et al., "Characterization of the human growth hormone receptor gene and demonstration of a partial gene deletion in two patients with Laron–type dwarfism" *Proc. Natl. Acad. Sci. USA* 86:8083–8087 (1989).

Gourmelen et al., "Effects of Exogenous Insulin–Like Growth Factor I on Insulin–Like Growth Factor Binding Proteins in a Case of Growth Hormone Insensitivity (Laron–Type)" *Acta Paediatr Scand Suppl.* 377:115–117 (1991).

Grahnen et al., "Pharmacokinetics of recombinant human insulin–like growth factor I given subcutaneously to healthy volunteers and to patients with growth hormone receptor deficiency" *Acta Paediatr Suppl.* 391:9–13 (1993).

Grunt et al. "Growth, Short Stature, and the Use of Growth Hormone: Considerations for the Practicing Pediatrician" *Current Problems in Pediatrics* 22:390–412 (1992).

Guevara–Aguirre et al., "Growth Hormone Receptor Deficiency (Laron Syndrome): Clinical and Genetic Characteristics" *Acta Paediatr Scand* (Suppl.) 377:96–103 (1991).

Hamill et al., "Physical Growth: National Center for Health Statistics Percentiles" *Amer. J. Clin. Nutrition* 32:607–629 (1979).

Hayek et al., "Growth and Somatomedin–C Responses to Growth Hormone in Dwarfed Children" *J. Pediatr.* 99(6):868–872 (1981).

Heinrich et al., "Multicenter Clinical Trial with Recombinant Human Growth Hormone (GH) in GH–Deficient and Non–GH–Deficient Children"*ACTA Endocrinologica* 120:82–83 (1989).

Heinrichs et al., "Effects on 17 months treatment using recombinant insulin–like growth factor–I in two children with growth hormone insensitivity (Laron) syndrome" *Clin. Endocrin.* 38:647–651 (1993)

Hochberg et al., "Regulation of Growth Hormone Receptor Turnover by Growth Hormone" *Acta Paediatr Scand* (Suppl.) 367:148–152 (1990).

Hopwood et al., "Growth response of children with non–growth–hormone deficiency and marked short stature during three years of growth hormone therapy" *J. Pediatr.* 123:215–222 (1993).

Ilondo et al., "Serum Growth Hormone Levels Measured by Radioimmunoassay and Radioreceptor Assay: A Useful Diagnostic Tool in Children with Growth Disorders?" *J. Clin. Endocrin. and Metabol.* 70(5):1445–1451 (1990).

Kalckreuth, "Constitutional Delay of Growth and Puberty: Do They Really Reach Their Target Height?" *Hormone Res.* 35:222–225 (1991).

Kanety et al., "Long–term treatment of Laron type dwarfs with insulin–like growth factor–1 increases serum insulin–like growth factor–binding protein–3 in the absence of growth hormone activity" *Acta Endocrinologica* 128:144–149 (1993).

Kaplan et al., "Clinical Studies with Recombinant–DNA–Derived Methiony Human Growth Hormone in Growth Hormone Deficient Children"*Lancet* 1:697–700 (1986).

Kerrigan et al., "Altered Growth Hormone Secretory Dynamics in Prepubertal Males with Constitutional Delay of Growth" *Pediatr. Res.* 33(3):278–283 (1993).

Kerrigan et al., "Variations of Pulsatile Growth Hormone Release in Healthy Short Prepubertal Boys" *Pediatr. Res.* 28:11–14 (1990).

Kou et al., "Amino Acid Substitutions in the Intracellular Part of the Growth Hormone Receptor in a Patient with the Laron Syndrome" *J. Clin. Endocrin. and Metabol.* 76:54–59 (1993).

Kowarski et al., "Growth Failure with Normal Serum RIA–GH and Low Somatomedin Activity: Somatomedin Restoration and Growth Acceleration After Exogenous GH" *J. Clin. Endocrin. and Metabol.* 47(2): 461–464 (1978).

Krassas et al., "GH, GHBP and IGF–I Axis in Idiopathic Tall Stature" *14th Joint Mtg. of the British Endocrine Soc.* (Abstract P246) 144(Suppl) (Mar. 1995).

LaFranchi et al., "Constitutional Delay of Growth: Expected versus Final Adult Height" *Pediatrics–Articles* 87:82–87 (1991).

Lajara et al., "Low Prevalence of Insulin–Like Growth Factor–I Gene Mutations in Human Growth Disorders" *J. Clin. Endocrin. and Metabol.* 70(3):687–692 (1990).

Lanes, "Diagnostic Limitations of Spontaneous Growth Hormone Measurements in Normally Growing Prepubertal Children" *AJDC* 143:1284–1286 (1989).

Laron, "Disorders of growth hormone resistance in childhood" *Current Science* (Endocrine and Metabolism) pp. 474–480 (1993).

Laron, "IGF–I therapy can promote growth in GH insensitivity" *Oxford Clin. Communications* (Int'l Workshop, Amsterdam), Kabi Pharmacia Growth Service pp. 1–4 (1992).

Laron, "Laron Syndrome: From Description to Therapy" *The Endocrinologist* 3:22–28 (1993).

Laron, "An update on Laron syndrome" *Archives of Disease in Childhood* 68:345–346 (1993).

Laron et al., "Biochemical and hormonal changes induced by one week of administration of rIGF–I to patients with Laron type dwarfism" *Clin. Endocrin.* 35:145–150 (1991).

Laron et al. "Body Fat in Laron Syndrome Patients: Effect of Insulin–Like Growth Factor I Treatment" *Hormone Res.* 40:16–22 (1993).

Laron et al., "Classification of growth hormone insensitivity syndrome" *J. Pediatr.* 122(2):241 (1993).

Laron et al., "Effect of Acute Administration of Insulin–Like Growth Factor I in Patients with Laron–Type Dwarfism" *Lancet* 2:1170–1172 (1988).

Laron et al., "Effects of insulin–like growth factor on linear growth, head circumference, and body fat in patients with Laron–type dwarfism" *Lancet* 339:1258–1260 (1992).

Laron et al., "Growth curves for Laron syndrome" *Archives of Disease in Childhood* 68:768–770 (1993).

Laron et al., "Larson syndrome due to a post–receptor defect: response to IGF–I treatemetn" *Israel J. Med. Sciences* 29:757–763 (1993).

Laron et al., "Serum GH Binding Protein Activities Identifies the Heterozygous Carriers for Laron Type Dwarfism" *Acta Endocrinologica* 121:603–608 (1989).

Leonard et al., "Anthropometric assessment of anabolic and lipolytic effects of recombinant IGF–I therapy in 3 children with growth hormone insensitivity syndrome (GHIS)" *Pediatr. Res.* 33:S43 (1993).

LeRoith et al., "Insulin–like Growth Factors in Health and Disease" *Annals of Internal Med.* 116:854–862 (1992).

Leung et al., "Growth hormone receptor and serum binding protein: purification, cloning and expression" *Nature* 330:537–543 (1987).

Lim et al., "Regulation of Growth Hormone (GH) Bioactivity by a Recombinant Human GH–Binding Protein" *The Endocrine Society* 127:1287–1291 (1990).

Lippe et al., "Conventional and Nonconventional Uses of Growth Hormone" *Recent Progress in Hormone Res.* 48:179–235 (1993).

Lippe et al., "IGF–I: wide–ranginge benefits" *ACTA Paediatr.* (2nd Int'l Workshop, Estoril Portugal) 83(Supp. 339) (1994).

Maddux et al., "Inhnibitors of Insulin–Receptor Tyrosine Kinase in Fibroblasts from Diverse Patients with Impaired Insulin Action: Evidence for a Novel Mechanism of Postreceptor Insulin–Resistance" *J. Clin. Endocrin. Metabol.* 77(1):73–79 (Jul 1993).

Martha et al., "Growth Hormone–Binding Protein Activity Is Inversely Related to 24–Hour Growth Hormone Release in Normal Boys" *J. Clin Endocrin. and Metabol.* 73: 175–181 (1991).

Martha et al., "Short term metabolic changes and long term response to recombinant IGF–I (rhIGF–I) therapy in a North American child with GH insensitivity (GHIS; Laron Syndrome)" *Pediatr. Res.* 33:S49 (1993).

Martha, Jr. et al., "Serum Growth Hormone (GH)–Binding Protein/Receptor: An Important Determinant of GH Responsiveness" *J. Clin. Endocrin. and Metabol.* 75:1464–1469 (1992).

Martin et al., "Effects of Insulin–Like Growth Factor–I Peptides in Rats with Acute Renal Failure" *J. Endocrin.* 140:23–32 (1994).

Martin et al., "IGF–I and its Variant, des–(1–3)IGF–I, Enhance Growth in Rats with Reduced Renal Mass" *Am. J. Physiol.* 261:F626–F633 (1991).

Martin et al., "Insulin–Like Growth Factor I and its Variant, Des(1–3)IGF–I, Improve Nitrogen Balance and Food Utilization in Rats with Renal Failure" *Miner. Electrolyte Metabol.* 18:264–268 (1992).

Mauras et al., "Growth Hormone–Binding Protein Levels: Studies of Children with Short Stature" *Metabolism* 43(3):357–359 (1994).

Merimee et al., "Growth Hormone–Binding Protein: II. Studies in Pygmies and Normal Statured Subjects" *J. Clin. Endocrin. and Metabol.* 71:1183–1188 (1990).

Merimee et al., "Hormone and Receptor Studies: Relationship to Linear Growth in Childhood and Puberty" *J. Clin. Endocrin. and Metabol.* 73:1031–1037 (1991).

Momoi et al., "Short stature with normal growth hormone and elevated IGF–I" *Euro. J. Pediatr.* 151:321–325 (1992).

Pierson et al., "Le Nanisme Familial de Type Laron, Deficit Genetique Primaire en Somatomedine" *Arch. Franc. Pediatr.* (English abstract) 35:151–164 (1978).

Postel–Vinay et al., "Human Plasma Growth Hormone (GH)–Binding Proteins Are Regulated by GH and Testosterone" *J. Clin. Endocrin. and Metabol.* 73:197–201 (1991).

Preece, "Discussion—Could you elaborate on the management of the four patients with severe hypglycaermia?" *Acta Paediatr Suppl.* 391:21 (1993).

Ranke et al., "Adult Height in Children with Constitutional Short Stature" *Acta Paediatr Scand Suppl.* 362:27–31 (1989).

Rabnik–Glavac et al., "Sensitivity of single–strand conformation polymorphism and heteroduplex method for mutation detection in the cystic fibrosis gene" *Hum. Mol. Genet.* 3(5):801–807 (1994).

Read et al., "Insulin–Like Growth Factor–I and its N–terminal Modified Analogues Induce Marked Gut Growth in Dexamethasone–Treated Rats" *J. Endocrin.* 133:421–431 (1992).

Rose et al., "The Advantage of Measuring Stimulated as Compared with Spontaneous Growth Hormone Levels in the Diagnosis of Growth Hormone Deficiency" *New England J. of Med.* 319:201–207 (1988).

Rosenbloom,, "The chronicle of growth hormone receptor deficiency (Laron syndrome)" *Actapaediatr Suppl.* 383:117–120 (1992).

Rosenbloom et al., "Is There Heterozygote Expression of Growth Hormone Receptor Deficiency?" *Acta Paediatr. Suppl.* 399:125–127 (1994).

Rosenfeld et al., "Growth Hormone (GH) Insensitivity Due to Primary GH Receptor Deficiency" *Endocrine Reviews* 15(3):369–390 (1994).

Santiago, "Lessons From the Diabetes Control and Complications Trail" *Diabetes* 42:1549–1554 (1993).

Savage et al., "Clinical Features and Endocrine Status in Patients with Growth Hormone Insensitivity (Laron Syndrome)" *J. Clin. Endocrin. and Metabol.* 77(6):1465–1471 (1993).

Savage et al., "Clinical Spectrum of the Syndrome of Growth Hormone Insensitivity" *Acta Paediatr Scand Suppl.* 377:87–90 (1991).

Savage et al., "Therapeutic response to recombinant IGF–1 in thirty two patients with growth hormone insensitivity" *Pediatr. Res.* 33:S5 (1993).

Sbraccia et al., "Production of Inhibitor of insulin–Receptor Tyrosine Kinase in Fibroblasts from Patient with Insulin Resistance and NIDDM" *Diabetes* 40:295–299 (1991).

Shafrir, "Genetic dwarfism with high growth hormone levels–multiple causation of GH nonresponsiveness" *Israel J. of Med. Sciences* 29:800–801 (1993).

Smith et al., "Mouse Serum Growth Hormone (GH) Binding Protein has GH Receptor Extracellular and Substituted Transmembrane Domains" *Molecular Endocrinology* 3:984–990 (1989).

Sotiropoulos et al., "Evidence For Generation of the Growth Hormone–Binding Protein Through Proteolysis of the Growth Hormone Membrane Receptor" *Endocrinology* 132(4):1863–1865 (1993).

Spiliotis et al., "Growth Hormone Neurosecretory Dysfunction" *Journal of the American Medical Assn.* 251:2223–2230 (1984).

Takano et al., "Effects of Short–Term Growth Hormone Therapy in Short Children without Growth Hormone Deficiency" *Acta Paediatr Scand* (Suppl.) 366:14–22 (1990).

Taylor et al., "Mutations in the Insulin Receptor Gene" *Endocrine Rev.* 13(3):566–595 (1992).

Tomas et al., "Anabolic Effects of Insulin–Like Growth Factor–I (IGF–I) and an IGF–I Variant in Normal Female Rats" *J. Endocrin.* 137:413–421 (1993).

Tomas et al., "Insulin–Like Growth Factor–I and More Potent Variants Restore Growth of Diabetic Rats without Inducing All Characteristic Insulin Effects" *Biochemical Journal* 291:781–786 (1993).

Tonshoff et al., "Effects of Two Years of Growth Hormone Treatment in Short Children with Renal Disease" *Acta Paediatr Scand* 379:33–41 (1991).

Trivedi et al., "Release of Growth Hormone Binding Protein from IM–9 Lymphocytes by Endopeptidase is Dependent on Sulfydryl Group Inactivation" *The Endocrine Society* 123:2201–2206 (1988).

Underwood et al., "IGFs: Function and Clinical Importance 6 Therapy With Recombinant Human Insulin–like Growth Factor I in Children With Insensitivity to Growth Hormone and in catabolic conditions" *J. Internal Med.* 234:571–577 (1993).

Vaccarello et al., "Hormonal and Metabolic Effects and Pharmacokinetics of Recombinant Insulin–Like Growth Factor–I in Growth Hormone Receptor Deficiency/Laron Syndrome" *J. Clin. Endocrin. and Metabol.* 77:273–280 (1993).

Valenta et al., "Pituitary Dwarfism in a Patient with Circulating Abnormal Growth Hormone Polymers" *New England J. of Med.* 312:214–217 (1985).

Veldhuis et al., "Properties of Spontaneous Growth Hormone Secretory Bursts and Half–Life of Endogenous Growth Hormone in Boys with Idiopathic Short Stature" *J. Clin. Endocrin. and Metabol.* 74:766–733 (1992).

Vidal–Puig et al., "Comparative Sensitivity of Alternatibe Single–Strand Conformation Polymorphism (SSCP) Methods" *Biotechniques* 17(3):490–496 (1994).

Walker et al., "Effects of Recombinant Insulin–Like Growth Factor I on IGF Binding Proteins and the Acid–Libile Subunit in Growth Hormone Insensitivity Syndrome" *Growth Regulation* pp. 109–112.

Walker et al., "Effects of the infusion of insulin–like growth factor I in a child with growth hormone insensitivity syndrome (Laron dwarfism)" *Brief Report* 324:1483–1488 (1991).

Walker et al., "Stimulation of statural growth by recombinant insulin–like growth factor I in a child with growth hormone insensitivity syndrome (Laron type)" *J. Pediatr.* 121:641–646 (1992).

Wilton et al., "Treatment with recombinant human insulin–like growth factor I of children with growth hormone receptor deficiency (Laron syndrome)" *Acta Paediatr Suppl* 383:137–141 (1992).

Zadik et al., "Do Short Children Secrete Insufficient Growth Hormone?" *Pediatrics–Articles* 76:355–360 (1985).

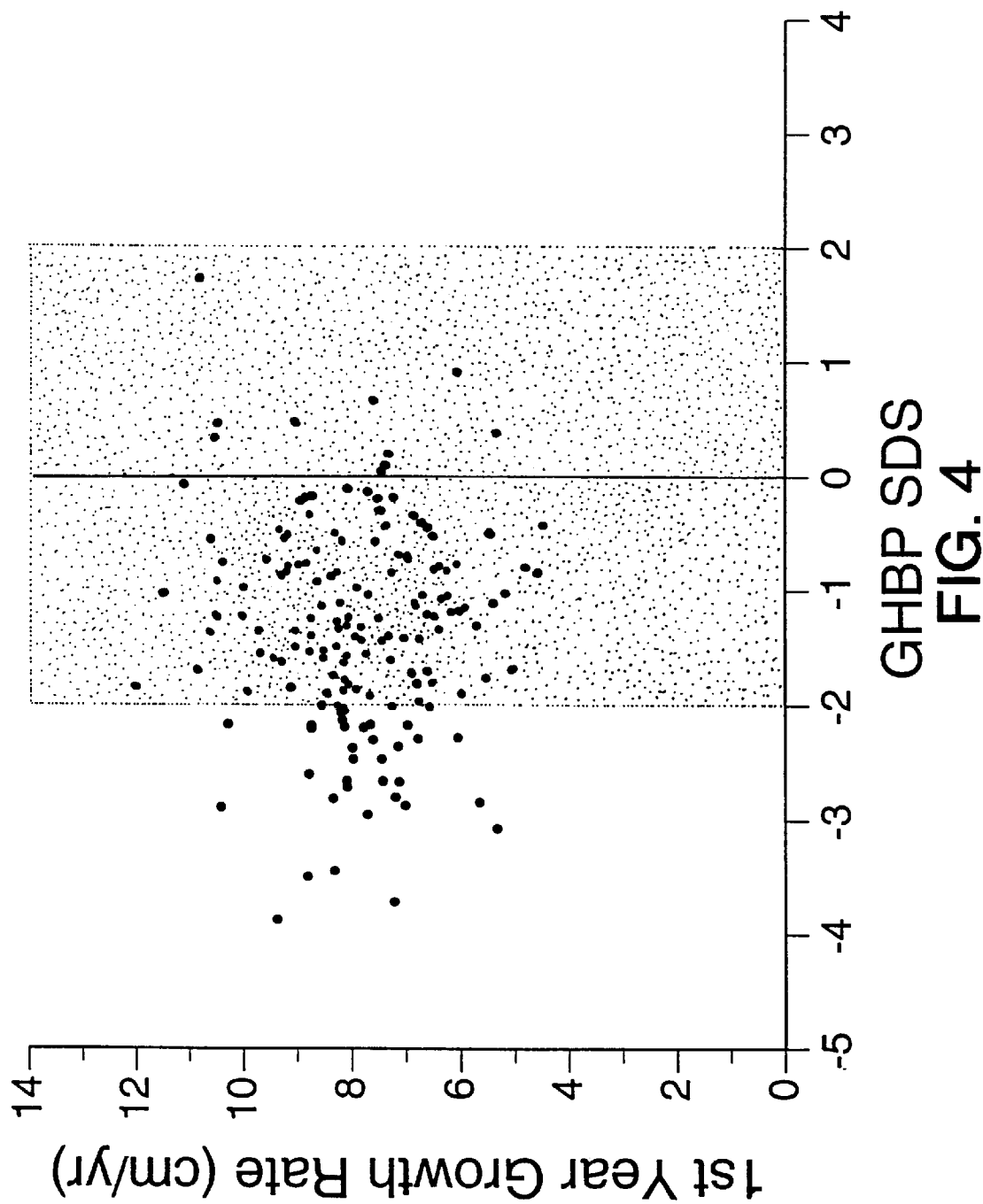

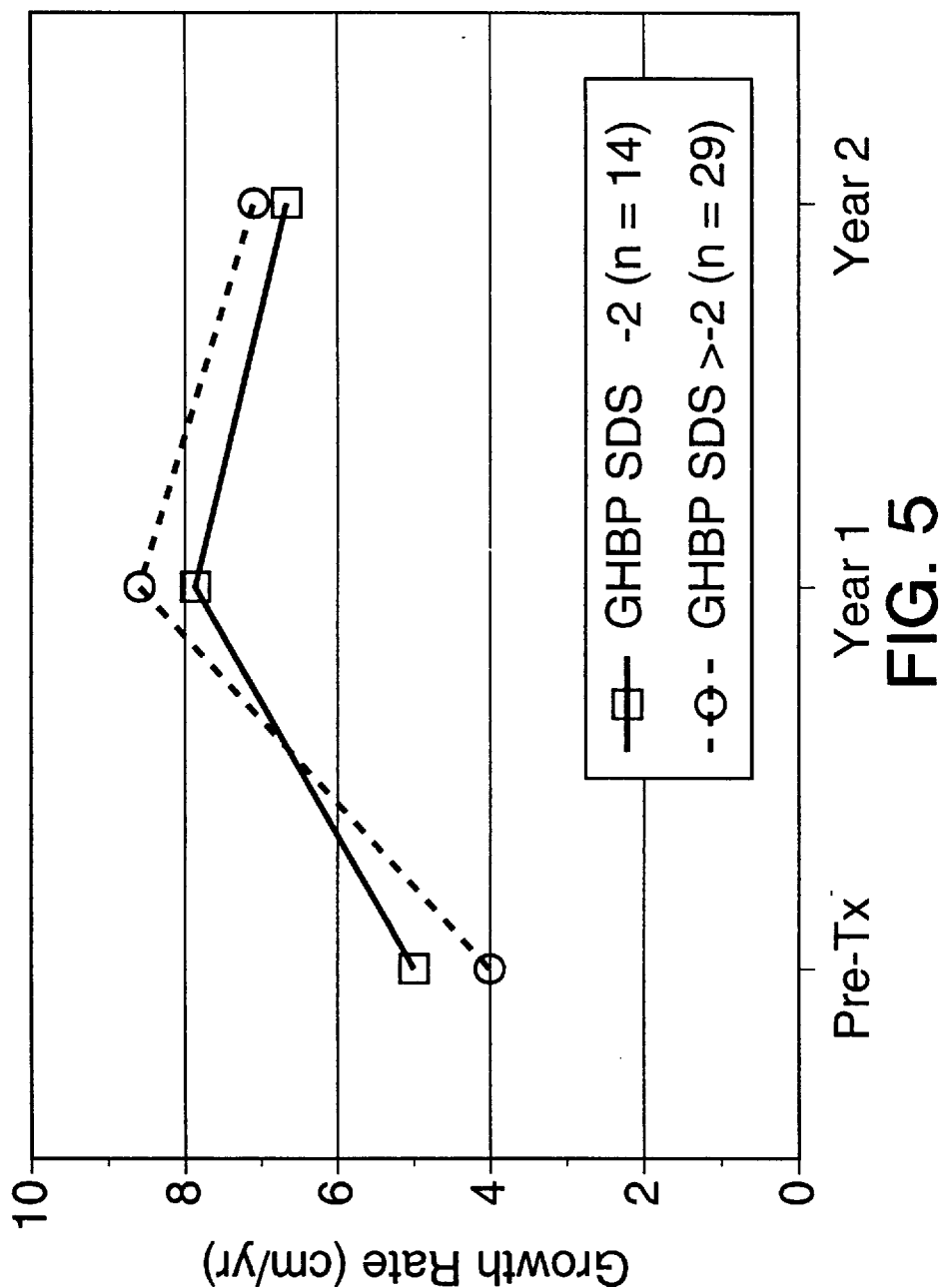

| | |
|---|---|
| GHR allele 1 | ATCCTCTAAG GAGCCTAAAT TCACCAAGTG CCGTTCACCT GAGCGAGAGA CTTTTTCATG CCACTGGACA |
| | S S K E P K F T K C R S P E R E T F S C H W T |
| GHR allele 2 | ATCCTCTAAG GAGCCTAAAT TCACCAAGTG CCGTTCACCT GAGCGAAAGA CTTTTTCATG CCACTGACA |
| | S S K E P K F T K C R S P E R [K] F S C H W T |
| GHR allele 1 | GATGAGGTTC ATCATGGTAC AAAGAACCTA GGACCCATAC AGCTGTTCTA TACCAGAAG\|G AACACTCAAG |
| | D E V H H G T K N L G P I Q L F Y T R R N T Q E |
| GHR allele 2 | GATGAGGTTC ATCATGGTAC AAAGAACCTA GGACCCATAC AGCTGTTCTA TACCAGAAG\|G AACACTCAAG |
| | D E V H H G T K N L G P I Q L F Y T R R N T Q E |
| GHR allele 1 | AATGGACTCA AGAATGGAAA GAATGCCCTG ATTATGTTTC TGCTGGGAA AACAGCTGTT ACTTAATTC |
| | W T Q E W K E C P D Y V S A G E N S C Y F N S |
| GHR allele 2 | AATGGACTCA AGAATGGAAA GAATGCCCTG ATTATGTTTC TGCTGGGAA AACAGCTGTT ACTTAATTC |
| | W T Q E W K E C P D Y V S A G E N S C Y F N S |
| GHR allele 1 | ATCGTTTACC TCCATCTGGA TACCTTATTG TATCAAGCTA ACTAGCAATG TTGCCCTCAA CTGGACTTTA CTGAACGTCA |
| | S F T S I W I P Y C I K L T S N G T V D E K |
| GHR allele 2 | ATCGTTTACC TCCATCTGGA TACCTTATTG TATCAAGCTA ACTAGCAATG TTGCCCTCAA CTGGACTTTA CTGAACGTCA |
| | S F T S I W I P Y C I K L T S N G T V D E K |
| GHR allele 1 | TGTTTCTCTG TTGATGAAAT AG\|TGCAACCA GATCCACCA TTGCCCTCAA CTGGACTTTA CTGAACGTCA GTGGTACAGT GGATGAAAAG |
| | C F S V D E I V\|Q P D P P I A L N W T L N V S |
| GHR allele 2 | TGTTTCTCTG TTGATGAAAT AG\|TGCAACCA GATCCACCA TTGCCCTCAA CTGGACTTTA CTGAACGTCA GTGGTACAGT GGATGAAAAG |
| | C F S V D E I V\|Q P D P P I A L N W T L N V S |
| GHR allele 1 | GTTTAACTGG GATTCATGCA GATATCCAAG TGAGATGGGA AGCACCATGC AATGCAGATA TTCAGAAAGG |
| | L T G I H A D I Q V R W E A P N A D I Q K G |
| GHR allele 2 | GTTTAACTGG GATTCATGCA GATATCCAAG TGAGATGGGA AGCACCACGC AATGCAGATA TTCAGAAAGG |
| | L T G I H A D I Q V R W E A P R N A D I Q K G |
| GHR allele 1 | GTGGATGGTT CTGGAGTATG AACTT |
| | W M V L E Y E L |
| GHR allele 2 | GTGGATGGTT CTGGAGTATG AACTT |
| | W M V L E Y E L |

FIG. 8

| | | | | | | |
|---|---|---|---|---|---|---|
|GHR allele 1|GAACACTCAA|GAATGGACTC|AAGAATGGAA|AGAATGCCCT|GATTATGTTT|CTGCTGGGGA|
| |N T Q|E W T Q|E W K|E C P|D Y V S|A G E|
|GHR allele 2|GAACACTCAA|GAATGGACTC|AAGAATGGAA|AGAATGCCCT|GATTATGTTT|CTGCTGGGGA|
| |N T Q|E W T Q|E W K|E C P|D Y V S|A G E|
| | | | | | | |
|GHR allele 1|AAACAGCTGT|TACTTTAATT|CATCGTTTAC|CTCCATCTGG|ATACCTTATT|GTATCAAGCT|
| |N S C|Y F N S|S F T|S I W|I P Y C|I K L|
|GHR allele 2|AAACAGCTGT|TACTTTAATT|CATCGTTTAC|CTCCATCTGG|ATACCTTATT|GTATCAAGCT|
| |N S C|Y F N S|S F T|S I W|I P Y C|I K L|
| | | | | | | |
|GHR allele 1|AACTAGCAAT|GGTGGTACAG|TGGATGAAAA|GTGTTTCTCT|GTTGATGAAA|TAG|
| |T S N|G G T V|D E K|C F S|V D E I| |
|GHR allele 2|AACTAGCAAT|GGTGGTACAG|TGGATGAAAA|GTGATTCTCT|GTTGATGAAA|TAG|
| |T S N|G G T V|D E K|ㅤ|ㅤ|Stop|

FIG. 9

```
GHR allele 1   gactctttgg ccaatatgcg tttatatttt gtcttgaaag|ATGGACCCTA TATTGACAAC
                                                          |M  D  P  I  L  T  T
GHR allele 2   gactctttgg ccaatatgcg tttatatttt gtcttgaaag|ATGGACCCTA TATTGACAAC
                                                          |M  D  P  I  L  T  T GHR allele 1   ATCAGTTCCA GTGTACTCAT TGAAAGTGGA TAAGGAATAT GAAGTGCGTG TGAGATCCAA
                S  V  P   V  Y  S  L  K  V  D   K  E  Y   E  V  R  V   R  S  K
GHR allele 2   ATCAGTTCCA GTGTACTCAT TGAAAGTGGA TAAGGAATAT GAAGTGCATG TGAGATCCAA
                S  V  P   V  Y  S  L  K  V  D   K  E  Y   E  V  [H] V  R  S  K GHR allele 1   ACAACGAAAC TCTGGAAATT ATGGCGAGTT CAGTGAGGTG CTCTATGTAA CACTTCCTCA
                Q  R  N   S  G  N  Y  G  E  F  S  E  V   L  Y  V  T   L  P  Q
GHR allele 2   ACAACGAAAC TCTGGAAATT ATGGCGAGTT CAGTGAGGTG CTCTATGTAA CACTTCCTCA
                Q  R  N   S  G  N  Y  G  E  F  S  E  V   L  Y  V  T   L  P  Q GHR allele 1   GATGAGCCAA TTTACATGTG AAGAAG|gtaa aagaaataaa agattaaaat agtagctaac
                M  S  Q   F  T  C  E  E  E   |
GHR allele 2   GATGAGCCAA TTTACATGTG AAGAAG|gtaa aagaaataaa agattaaaat agtagctaac
                M  S  Q   F  T  C  E  E  E   |
```

FIG. 10

```
GHR allele 1         gactctttgg ccaatatgcg tttatatttt gtcttgaaag|ATGGACCCTA TATTGACAAC
                                                               |M  D  P  I  L  T  T
GHR allele 2         gactctttgg ccaatatgcg tttatatttt gtcttgaaag|ATGGACCCTA TATTGACAAC
                                                               |M  D  P  I  L  T  T GHR allele 1  ATCAGTTCCA GTGTACTCAT TGAAAGTGGA TAAGGAATAT GAAGTGCGTG TGAGATCCAA
              S  V  P    V  Y  S  L    K  V  D    K  E  Y    E  V  R  V    R  S  K
GHR allele 2  ATCAGTTCCA GTGTACTCAT TGAAAGTGGA TAAGGAATAT GAAGTGCGTG TGAGATCCAA
              S  V  P    V  Y  S  L    K  V  D    K  E  Y    E  V  R  V    R  S  K GHR allele 1  ACAACGAAAC TCTGGAAATT ATGGCGAGTT CAGTGAGGTG CTCTATGTAA CACTTCCTCA
              Q  R  N    S  G  N  Y    G  E  F    S  E  V    L  Y  V  T    L  P  Q
GHR allele 2  ACAACGAAAC TCTGGAAATT ATGGCGACTT CAGTGAGGTG CTCTATGTAA CACTTCCTCA
              Q  R  N    S  G  N  Y    G  [D]  F    S  E  V    L  Y  V  T    L  P  Q GHR allele 1  GATGAGCCAA TTTACATGTG AAGAAG|gtaa aagaaataaa agattaaaat agtagctaac
              M  S  Q    F  T  C  E    E  |
GHR allele 2  GATGAGCCAA TTTACATGTG AAGAAG|gtaa aagaaataaa agattaaaat agtagctaac
              M  S  Q    F  T  C  E    E  |
```

FIG. 11

SEQUENCE LISTING ( 1 ) GENERAL INFORMATION:

( i i i ) NUMBER OF SEQUENCES: 57

( 2 ) INFORMATION FOR SEQ ID NO:1:

( i ) SEQUENCE CHARACTERISTICS:
        ( A ) LENGTH: 445 bases
        ( B ) TYPE: nucleic acid
        ( C ) STRANDEDNESS: single
        ( D ) TOPOLOGY: linear ( x i ) SEQUENCE DESCRIPTION: SEQ ID NO:1:

```
ATCCTCTAAG  GAGCCTAAAT  TCACCAAGTG  CCGTTCACCT  GAGCGAGAGA      50
CTTTTTCATG  CCACTGGACA  GATGAGGTTC  ATCATGGTAC  AAAGAACCTA     100
GGACCCATAC  AGCTGTTCTA  TACCAGAAGG  AACACTCAAG  AATGGACTCA     150
AGAATGGAAA  GAATGCCCTG  ATTATGTTTC  TGCTGGGGAA  AACAGCTGTT     200
ACTTTAATTC  ATCGTTTACC  TCCATCTGGA  TACCTTATTG  TATCAAGCTA     250
ACTAGCAATG  GTGGTACAGT  GGATGAAAAG  TGTTTCTCTG  TTGATGAAAT     300
AGTGCAACCA  GATCCACCCA  TTGCCCTCAA  CTGGACTTTA  CTGAACGTCA     350
GTTTAACTGG  GATTCATGCA  GATATCCAAG  TGAGATGGGA  AGCACCATGC     400
AATGCAGATA  TTCAGAAAGG  GTGGATGGTT  CTGGAGTATG  AACTT          445
```

( 2 ) INFORMATION FOR SEQ ID NO:2:

( i ) SEQUENCE CHARACTERISTICS:
        ( A ) LENGTH: 445 bases
        ( B ) TYPE: nucleic acid
        ( C ) STRANDEDNESS: single
        ( D ) TOPOLOGY: linear ( x i ) SEQUENCE DESCRIPTION: SEQ ID NO:2:

```
ATCCTCTAAG  GAGCCTAAAT  TCACCAAGTG  CCGTTCACCT  GAGCGAAAGA      50
CTTTTTCATG  CCACTGGACA  GATGAGGTTC  ATCATGGTAC  AAAGAACCTA     100
GGACCCATAC  AGCTGTTCTA  TACCAGAAGG  AACACTCAAG  AATGGACTCA     150
AGAATGGAAA  GAATGCCCTG  ATTATGTTTC  TGCTGGGGAA  AACAGCTGTT     200
ACTTTAATTC  ATCGTTTACC  TCCATCTGGA  TACCTTATTG  TATCAAGCTA     250
ACTAGCAATG  GTGGTACAGT  GGATGAAAAG  TGTTTCTCTG  TTGATGAAAT     300
AGTGCAACCA  GATCCACCCA  TTGCCCTCAA  CTGGACTTTA  CTGAACGTCA     350
GTTTAACTGG  GATTCATGCA  GATATCCAAG  TGAGATGGGA  AGCACCACGC     400
AATGCAGATA  TTCAGAAAGG  GTGGATGGTT  CTGGAGTATG  AACTT          445
```

( 2 ) INFORMATION FOR SEQ ID NO:3:

( i ) SEQUENCE CHARACTERISTICS:
        ( A ) LENGTH: 148 amino acids
        ( B ) TYPE: amino acid
        ( D ) TOPOLOGY: linear ( x i ) SEQUENCE DESCRIPTION: SEQ ID NO:3:

```
Ser  Ser  Lys  Glu  Pro  Lys  Phe  Thr  Lys  Cys  Arg  Ser  Pro  Glu  Arg
 1              5                        10                       15

Glu  Thr  Phe  Ser  Cys  His  Trp  Thr  Asp  Glu  Val  His  His  Gly  Thr
                20                       25                       30
```

| | | | | | | | | | | | | | | |
|---|---|---|---|---|---|---|---|---|---|---|---|---|---|---|
|Lys|Asn|Leu|Gly|Pro<br>35|Ile|Gln|Leu|Phe|Tyr<br>40|Thr|Arg|Arg|Asn|Thr<br>45|
|Gln|Glu|Trp|Thr|Gln<br>50|Glu|Trp|Lys|Glu|Cys<br>55|Pro|Asp|Tyr|Val|Ser<br>60|
|Ala|Gly|Glu|Asn|Ser<br>65|Cys|Tyr|Phe|Asn|Ser<br>70|Ser|Phe|Thr|Ser|Ile<br>75|
|Trp|Ile|Pro|Tyr|Cys<br>80|Ile|Lys|Leu|Thr|Ser<br>85|Asn|Gly|Gly|Thr|Val<br>90|
|Asp|Glu|Lys|Cys|Phe<br>95|Ser|Val|Asp|Glu|Ile<br>100|Val|Gln|Pro|Asp|Pro<br>105|
|Pro|Ile|Ala|Leu|Asn<br>110|Trp|Thr|Leu|Leu|Asn<br>115|Val|Ser|Leu|Thr|Gly<br>120|
|Ile|His|Ala|Asp|Ile<br>125|Gln|Val|Arg|Trp|Glu<br>130|Ala|Pro|Cys|Asn|Ala<br>135|
|Asp|Ile|Gln|Lys|Gly<br>140|Trp|Met|Val|Leu|Glu<br>145|Tyr|Glu|Leu<br>148| | |

( 2 ) INFORMATION FOR SEQ ID NO:4:

( i ) SEQUENCE CHARACTERISTICS:
        ( A ) LENGTH: 148 amino acids
        ( B ) TYPE: amino acid
        ( D ) TOPOLOGY: linear ( x i ) SEQUENCE DESCRIPTION: SEQ ID NO:4:

| | | | | | | | | | | | | | | |
|---|---|---|---|---|---|---|---|---|---|---|---|---|---|---|
|Ser<br>1|Ser|Lys|Glu|Pro<br>5|Lys|Phe|Thr|Lys|Cys<br>10|Arg|Ser|Pro|Glu|Arg<br>15|
|Lys|Thr|Phe|Ser|Cys<br>20|His|Trp|Thr|Asp|Glu<br>25|Val|His|His|Gly|Thr<br>30|
|Lys|Asn|Leu|Gly|Pro<br>35|Ile|Gln|Leu|Phe|Tyr<br>40|Thr|Arg|Arg|Asn|Thr<br>45|
|Gln|Glu|Trp|Thr|Gln<br>50|Glu|Trp|Lys|Glu|Cys<br>55|Pro|Asp|Tyr|Val|Ser<br>60|
|Ala|Gly|Glu|Asn|Ser<br>65|Cys|Tyr|Phe|Asn|Ser<br>70|Ser|Phe|Thr|Ser|Ile<br>75|
|Trp|Ile|Pro|Tyr|Cys<br>80|Ile|Lys|Leu|Thr|Ser<br>85|Asn|Gly|Gly|Thr|Val<br>90|
|Asp|Glu|Lys|Cys|Phe<br>95|Ser|Val|Asp|Glu|Ile<br>100|Val|Gln|Pro|Asp|Pro<br>105|
|Pro|Ile|Ala|Leu|Asn<br>110|Trp|Thr|Leu|Leu|Asn<br>115|Val|Ser|Leu|Thr|Gly<br>120|
|Ile|His|Ala|Asp|Ile<br>125|Gln|Val|Arg|Trp|Glu<br>130|Ala|Pro|Arg|Asn|Ala<br>135|
|Asp|Ile|Gln|Lys|Gly<br>140|Trp|Met|Val|Leu|Glu<br>145|Tyr|Glu|Leu<br>148| | |

( 2 ) INFORMATION FOR SEQ ID NO:5:

( i ) SEQUENCE CHARACTERISTICS:
        ( A ) LENGTH: 173 bases
        ( B ) TYPE: nucleic acid
        ( C ) STRANDEDNESS: single
        ( D ) TOPOLOGY: linear ( x i ) SEQUENCE DESCRIPTION: SEQ ID NO:5:

| | | | | | |
|---|---|---|---|---|---|
|GAACACTCAA|GAATGGACTC|AAGAATGGAA|AGAATGCCCT|GATTATGTTT|50|
|CTGCTGGGGA|AAACAGCTGT|TACTTTAATT|CATCGTTTAC|CTCCATCTGG|100|

```
ATACCTTATT GTATCAAGCT AACTAGCAAT GGTGGTACAG TGGATGAAAA                    150

GTGTTTCTCT GTTGATGAAA TAG                                                173
```

( 2 ) INFORMATION FOR SEQ ID NO:6:

( i ) SEQUENCE CHARACTERISTICS:
        ( A ) LENGTH: 173 bases
        ( B ) TYPE: nucleic acid
        ( C ) STRANDEDNESS: single
        ( D ) TOPOLOGY: linear ( x i ) SEQUENCE DESCRIPTION: SEQ ID NO:6:

```
GAACACTCAA GAATGGACTC AAGAATGGAA AGAATGCCCT GATTATGTTT                    50

CTGCTGGGGA AAACAGCTGT TACTTTAATT CATCGTTTAC CTCCATCTGG                    100

ATACCTTATT GTATCAAGCT AACTAGCAAT GGTGGTACAG TGGATGAAAA                    150

GTGATTCTCT GTTGATGAAA TAG                                                173
```

( 2 ) INFORMATION FOR SEQ ID NO:7:

( i ) SEQUENCE CHARACTERISTICS:
        ( A ) LENGTH: 57 amino acids
        ( B ) TYPE: amino acid
        ( D ) TOPOLOGY: linear ( x i ) SEQUENCE DESCRIPTION: SEQ ID NO:7:

```
Asn Thr Gln Glu Trp Thr Gln Glu Trp Lys Glu Cys Pro Asp Tyr
 1               5                  10                  15

Val Ser Ala Gly Glu Asn Ser Cys Tyr Phe Asn Ser Ser Phe Thr
                20                  25                  30

Ser Ile Trp Ile Pro Tyr Cys Ile Lys Leu Thr Ser Asn Gly Gly
                35                  40                  45

Thr Val Asp Glu Lys Cys Phe Ser Val Asp Glu Ile
                50                  55      57
```

( 2 ) INFORMATION FOR SEQ ID NO:8:

( i ) SEQUENCE CHARACTERISTICS:
        ( A ) LENGTH: 50 amino acids
        ( B ) TYPE: amino acid
        ( D ) TOPOLOGY: linear ( x i ) SEQUENCE DESCRIPTION: SEQ ID NO:8:

```
Asn Thr Gln Glu Trp Thr Gln Glu Trp Lys Glu Cys Pro Asp Tyr
 1               5                  10                  15

Val Ser Ala Gly Glu Asn Ser Cys Tyr Phe Asn Ser Ser Phe Thr
                20                  25                  30

Ser Ile Trp Ile Pro Tyr Cys Ile Lys Leu Thr Ser Asn Gly Gly
                35                  40                  45

Thr Val Asp Glu Lys
                50
```

( 2 ) INFORMATION FOR SEQ ID NO:9:

( i ) SEQUENCE CHARACTERISTICS:
        ( A ) LENGTH: 240 bases
        ( B ) TYPE: nucleic acid
        ( C ) STRANDEDNESS: single
        ( D ) TOPOLOGY: linear ( x i ) SEQUENCE DESCRIPTION: SEQ ID NO:9:

```
GACTCTTTGG CCAATATGCG TTTATATTTT GTCTTGAAAG ATGGACCCTA                    50
```

```
TATTGACAAC  ATCAGTTCCA  GTGTACTCAT  TGAAAGTGGA  TAAGGAATAT              100

GAAGTGCGTG  TGAGATCCAA  ACAACGAAAC  TCTGGAAATT  ATGGCGAGTT              150

CAGTGAGGTG  CTCTATGTAA  CACTTCCTCA  GATGAGCCAA  TTTACATGTG              200

AAGAAGGTAA  AAGAAATAAA  AGATTAAAAT  AGTAGCTAAC                          240
```

( 2 ) INFORMATION FOR SEQ ID NO:10:

( i ) SEQUENCE CHARACTERISTICS:
        ( A ) LENGTH: 240 bases
        ( B ) TYPE: nucleic acid
        ( C ) STRANDEDNESS: single
        ( D ) TOPOLOGY: linear ( x i ) SEQUENCE DESCRIPTION: SEQ ID NO:10:

```
GACTCTTTGG  CCAATATGCG  TTTATATTTT  GTCTTGAAAG  ATGGACCCTA               50

TATTGACAAC  ATCAGTTCCA  GTGTACTCAT  TGAAAGTGGA  TAAGGAATAT              100

GAAGTGCATG  TGAGATCCAA  ACAACGAAAC  TCTGGAAATT  ATGGCGAGTT              150

CAGTGAGGTG  CTCTATGTAA  CACTTCCTCA  GATGAGCCAA  TTTACATGTG              200

AAGAAGGTAA  AAGAAATAAA  AGATTAAAAT  AGTAGCTAAC                          240
```

( 2 ) INFORMATION FOR SEQ ID NO:11:

( i ) SEQUENCE CHARACTERISTICS:
        ( A ) LENGTH: 55 amino acids
        ( B ) TYPE: amino acid
        ( D ) TOPOLOGY: linear ( x i ) SEQUENCE DESCRIPTION: SEQ ID NO:11:

```
Met  Asp  Pro  Ile  Leu  Thr  Thr  Ser  Val  Pro  Val  Tyr  Ser  Leu  Lys
 1              5                        10                            15

Val  Asp  Lys  Glu  Tyr  Glu  Val  Arg  Val  Arg  Ser  Lys  Gln  Arg  Asn
               20                        25                            30

Ser  Gly  Asn  Tyr  Gly  Glu  Phe  Ser  Glu  Val  Leu  Tyr  Val  Thr  Leu
               35                        40                            45

Pro  Gln  Met  Ser  Gln  Phe  Thr  Cys  Glu  Glu
               50                        55
```

( 2 ) INFORMATION FOR SEQ ID NO:12:

( i ) SEQUENCE CHARACTERISTICS:
        ( A ) LENGTH: 55 amino acids
        ( B ) TYPE: amino acid
        ( D ) TOPOLOGY: linear ( x i ) SEQUENCE DESCRIPTION: SEQ ID NO:12:

```
Met  Asp  Pro  Ile  Leu  Thr  Thr  Ser  Val  Pro  Val  Tyr  Ser  Leu  Lys
 1              5                        10                            15

Val  Asp  Lys  Glu  Tyr  Glu  Val  His  Val  Arg  Ser  Lys  Gln  Arg  Asn
               20                        25                            30

Ser  Gly  Asn  Tyr  Gly  Glu  Phe  Ser  Glu  Val  Leu  Tyr  Val  Thr  Leu
               35                        40                            45

Pro  Gln  Met  Ser  Gln  Phe  Thr  Cys  Glu  Glu
               50                        55
```

( 2 ) INFORMATION FOR SEQ ID NO:13:

( i ) SEQUENCE CHARACTERISTICS:
        ( A ) LENGTH: 240 bases
        ( B ) TYPE: nucleic acid
        ( C ) STRANDEDNESS: single (D) TOPOLOGY: linear (xi) SEQUENCE DESCRIPTION: SEQ ID NO:13:

```
GACTCTTTGG  CCAATATGCG  TTTATATTTT  GTCTTGAAAG  ATGGACCCTA          50
TATTGACAAC  ATCAGTTCCA  GTGTACTCAT  TGAAAGTGGA  TAAGGAATAT         100
GAAGTGCGTG  TGAGATCCAA  ACAACGAAAC  TCTGGAAATT  ATGGCGAGTT         150
CAGTGAGGTG  CTCTATGTAA  CACTTCCTCA  GATGAGCCAA  TTTACATGTG         200
AAGAAGGTAA  AAGAAATAAA  AGATTAAAAT  AGTAGCTAAC                     240
```

(2) INFORMATION FOR SEQ ID NO:14:

(i) SEQUENCE CHARACTERISTICS:
        (A) LENGTH: 240 bases
        (B) TYPE: nucleic acid
        (C) STRANDEDNESS: single
        (D) TOPOLOGY: linear (xi) SEQUENCE DESCRIPTION: SEQ ID NO:14:

```
GACTCTTTGG  CCAATATGCG  TTTATATTTT  GTCTTGAAAG  ATGGACCCTA          50
TATTGACAAC  ATCAGTTCCA  GTGTACTCAT  TGAAAGTGGA  TAAGGAATAT         100
GAAGTGCGTG  TGAGATCCAA  ACAACGAAAC  TCTGGAAATT  ATGGCGACTT         150
CAGTGAGGTG  CTCTATGTAA  CACTTCCTCA  GATGAGCCAA  TTTACATGTG         200
AAGAAGGTAA  AAGAAATAAA  AGATTAAAAT  AGTAGCTAAC                     240
```

(2) INFORMATION FOR SEQ ID NO:15:

(i) SEQUENCE CHARACTERISTICS:
        (A) LENGTH: 55 amino acids
        (B) TYPE: amino acid
        (D) TOPOLOGY: linear (xi) SEQUENCE DESCRIPTION: SEQ ID NO:15:

```
Met  Asp  Pro  Ile  Leu  Thr  Thr  Ser  Val  Pro  Val  Tyr  Ser  Leu  Lys
 1                 5                         10                         15

Val  Asp  Lys  Glu  Tyr  Glu  Val  Arg  Val  Arg  Ser  Lys  Gln  Arg  Asn
                   20                         25                         30

Ser  Gly  Asn  Tyr  Gly  Glu  Phe  Ser  Glu  Val  Leu  Tyr  Val  Thr  Leu
                   35                         40                         45

Pro  Gln  Met  Ser  Gln  Phe  Thr  Cys  Glu  Glu
                   50                         55
```

(2) INFORMATION FOR SEQ ID NO:16:

(i) SEQUENCE CHARACTERISTICS:
        (A) LENGTH: 55 amino acids
        (B) TYPE: amino acid
        (D) TOPOLOGY: linear (xi) SEQUENCE DESCRIPTION: SEQ ID NO:16:

```
Met  Asp  Pro  Ile  Leu  Thr  Thr  Ser  Val  Pro  Val  Tyr  Ser  Leu  Lys
 1                 5                         10                         15

Val  Asp  Lys  Glu  Tyr  Glu  Val  Arg  Val  Arg  Ser  Lys  Gln  Arg  Asn
                   20                         25                         30

Ser  Gly  Asn  Tyr  Gly  Asp  Phe  Ser  Glu  Val  Leu  Tyr  Val  Thr  Leu
                   35                         40                         45

Pro  Gln  Met  Ser  Gln  Phe  Thr  Cys  Glu  Glu
                   50                         55
```

( 2 ) INFORMATION FOR SEQ ID NO:17:

( i ) SEQUENCE CHARACTERISTICS:
        ( A ) LENGTH: 18 bases
        ( B ) TYPE: nucleic acid
        ( C ) STRANDEDNESS: single
        ( D ) TOPOLOGY: linear ( x i ) SEQUENCE DESCRIPTION: SEQ ID NO:17:

TGCTGGGCTT TACCTTAC 18

( 2 ) INFORMATION FOR SEQ ID NO:18:

( i ) SEQUENCE CHARACTERISTICS:
        ( A ) LENGTH: 18 bases
        ( B ) TYPE: nucleic acid
        ( C ) STRANDEDNESS: single
        ( D ) TOPOLOGY: linear ( x i ) SEQUENCE DESCRIPTION: SEQ ID NO:18:

CAAAACACTG AGGGTGGA 18

( 2 ) INFORMATION FOR SEQ ID NO:19:

( i ) SEQUENCE CHARACTERISTICS:
        ( A ) LENGTH: 22 bases
        ( B ) TYPE: nucleic acid
        ( C ) STRANDEDNESS: single
        ( D ) TOPOLOGY: linear ( x i ) SEQUENCE DESCRIPTION: SEQ ID NO:19:

TACACAGGGT CATATCAGAT TG 22

( 2 ) INFORMATION FOR SEQ ID NO:20:

( i ) SEQUENCE CHARACTERISTICS:
        ( A ) LENGTH: 22 bases
        ( B ) TYPE: nucleic acid
        ( C ) STRANDEDNESS: single
        ( D ) TOPOLOGY: linear ( x i ) SEQUENCE DESCRIPTION: SEQ ID NO:20:

CTATTCCAGT TACTACCATC CC 22

( 2 ) INFORMATION FOR SEQ ID NO:21:

( i ) SEQUENCE CHARACTERISTICS:
        ( A ) LENGTH: 18 bases
        ( B ) TYPE: nucleic acid
        ( C ) STRANDEDNESS: single
        ( D ) TOPOLOGY: linear ( x i ) SEQUENCE DESCRIPTION: SEQ ID NO:21:

CTGATTTCAT GCCTTGCC 18

( 2 ) INFORMATION FOR SEQ ID NO:22:

( i ) SEQUENCE CHARACTERISTICS:
        ( A ) LENGTH: 18 bases
        ( B ) TYPE: nucleic acid
        ( C ) STRANDEDNESS: single
        ( D ) TOPOLOGY: linear ( x i ) SEQUENCE DESCRIPTION: SEQ ID NO:22:

AGAAAGGCAT GATGGTGG 18

( 2 ) INFORMATION FOR SEQ ID NO:23:

( i ) SEQUENCE CHARACTERISTICS:
  ( A ) LENGTH: 20 bases
  ( B ) TYPE: nucleic acid
  ( C ) STRANDEDNESS: single
  ( D ) TOPOLOGY: linear ( x i ) SEQUENCE DESCRIPTION: SEQ ID NO:23:

ACTTAAGCTA CAACATGATT 20

( 2 ) INFORMATION FOR SEQ ID NO:24:

( i ) SEQUENCE CHARACTERISTICS:
  ( A ) LENGTH: 19 bases
  ( B ) TYPE: nucleic acid
  ( C ) STRANDEDNESS: single
  ( D ) TOPOLOGY: linear ( x i ) SEQUENCE DESCRIPTION: SEQ ID NO:24:

GCTTCCCCAT TTATTTAGT 19

( 2 ) INFORMATION FOR SEQ ID NO:25:

( i ) SEQUENCE CHARACTERISTICS:
  ( A ) LENGTH: 19 bases
  ( B ) TYPE: nucleic acid
  ( C ) STRANDEDNESS: single
  ( D ) TOPOLOGY: linear ( x i ) SEQUENCE DESCRIPTION: SEQ ID NO:25:

ATGCTCTGTT GAATTGCAC 19

( 2 ) INFORMATION FOR SEQ ID NO:26:

( i ) SEQUENCE CHARACTERISTICS:
  ( A ) LENGTH: 19 bases
  ( B ) TYPE: nucleic acid
  ( C ) STRANDEDNESS: single
  ( D ) TOPOLOGY: linear ( x i ) SEQUENCE DESCRIPTION: SEQ ID NO:26:

GTGTAAGGTG TAGCAACAT 19

( 2 ) INFORMATION FOR SEQ ID NO:27:

( i ) SEQUENCE CHARACTERISTICS:
  ( A ) LENGTH: 18 bases
  ( B ) TYPE: nucleic acid
  ( C ) STRANDEDNESS: single
  ( D ) TOPOLOGY: linear ( x i ) SEQUENCE DESCRIPTION: SEQ ID NO:27:

GACTCTTTGG CCAATATG 18

( 2 ) INFORMATION FOR SEQ ID NO:28:

( i ) SEQUENCE CHARACTERISTICS:
  ( A ) LENGTH: 18 bases
  ( B ) TYPE: nucleic acid
  ( C ) STRANDEDNESS: single
  ( D ) TOPOLOGY: linear ( x i ) SEQUENCE DESCRIPTION: SEQ ID NO:28:

AAGCCAGGTT AGCTACTA 18

( 2 ) INFORMATION FOR SEQ ID NO:29:

( i ) SEQUENCE CHARACTERISTICS:
  ( A ) LENGTH: 21 bases (B) TYPE: nucleic acid
(C) STRANDEDNESS: single
(D) TOPOLOGY: linear (xi) SEQUENCE DESCRIPTION: SEQ ID NO:29:

GAAACTGTGC TTCAACTAGT C 21

(2) INFORMATION FOR SEQ ID NO:30:

(i) SEQUENCE CHARACTERISTICS:
(A) LENGTH: 20 bases
(B) TYPE: nucleic acid
(C) STRANDEDNESS: single
(D) TOPOLOGY: linear (xi) SEQUENCE DESCRIPTION: SEQ ID NO:30:

GGTCTAACAC AACTGGTACA 20

(2) INFORMATION FOR SEQ ID NO:31:

(i) SEQUENCE CHARACTERISTICS:
(A) LENGTH: 21 bases
(B) TYPE: nucleic acid
(C) STRANDEDNESS: single
(D) TOPOLOGY: linear (xi) SEQUENCE DESCRIPTION: SEQ ID NO:31:

ATGTAGCTTT TAACATCTCA A 21

(2) INFORMATION FOR SEQ ID NO:32:

(i) SEQUENCE CHARACTERISTICS:
(A) LENGTH: 18 bases
(B) TYPE: nucleic acid
(C) STRANDEDNESS: single
(D) TOPOLOGY: linear (xi) SEQUENCE DESCRIPTION: SEQ ID NO:32:

ATGACAGGAG TCTTCAGG 18

(2) INFORMATION FOR SEQ ID NO:33:

(i) SEQUENCE CHARACTERISTICS:
(A) LENGTH: 22 bases
(B) TYPE: nucleic acid
(C) STRANDEDNESS: single
(D) TOPOLOGY: linear (xi) SEQUENCE DESCRIPTION: SEQ ID NO:33:

GAGTTTCTTT TCATAGATCT TC 22

(2) INFORMATION FOR SEQ ID NO:34:

(i) SEQUENCE CHARACTERISTICS:
(A) LENGTH: 18 bases
(B) TYPE: nucleic acid
(C) STRANDEDNESS: single
(D) TOPOLOGY: linear (xi) SEQUENCE DESCRIPTION: SEQ ID NO:34:

TTAACCTCTG TGGCTGAG 18

(2) INFORMATION FOR SEQ ID NO:35:

(i) SEQUENCE CHARACTERISTICS:
(A) LENGTH: 18 bases
(B) TYPE: nucleic acid
(C) STRANDEDNESS: single ( D ) TOPOLOGY: linear ( x i ) SEQUENCE DESCRIPTION: SEQ ID NO:35:

ACATGAGGGT ACCTCAGA                                                                                                18

( 2 ) INFORMATION FOR SEQ ID NO:36:

( i ) SEQUENCE CHARACTERISTICS:
                ( A ) LENGTH: 18 bases
                ( B ) TYPE: nucleic acid
                ( C ) STRANDEDNESS: single
                ( D ) TOPOLOGY: linear ( x i ) SEQUENCE DESCRIPTION: SEQ ID NO:36:

CAGAAGTAGG CATTGTCC                                                                                                18

( 2 ) INFORMATION FOR SEQ ID NO:37:

( i ) SEQUENCE CHARACTERISTICS:
                ( A ) LENGTH: 18 bases
                ( B ) TYPE: nucleic acid
                ( C ) STRANDEDNESS: single
                ( D ) TOPOLOGY: linear ( x i ) SEQUENCE DESCRIPTION: SEQ ID NO:37:

GGAAATGGTC TCACTCTG                                                                                                18

( 2 ) INFORMATION FOR SEQ ID NO:38:

( i ) SEQUENCE CHARACTERISTICS:
                ( A ) LENGTH: 18 bases
                ( B ) TYPE: nucleic acid
                ( C ) STRANDEDNESS: single
                ( D ) TOPOLOGY: linear ( x i ) SEQUENCE DESCRIPTION: SEQ ID NO:38:

CCAAAGAAAG GCTAAGGC                                                                                                18

( 2 ) INFORMATION FOR SEQ ID NO:39:

( i ) SEQUENCE CHARACTERISTICS:
                ( A ) LENGTH: 21 bases
                ( B ) TYPE: nucleic acid
                ( C ) STRANDEDNESS: single
                ( D ) TOPOLOGY: linear ( x i ) SEQUENCE DESCRIPTION: SEQ ID NO:39:

GTCCTACAGG TATGGATCTC T                                                                                            21

( 2 ) INFORMATION FOR SEQ ID NO:40:

( i ) SEQUENCE CHARACTERISTICS:
                ( A ) LENGTH: 21 bases
                ( B ) TYPE: nucleic acid
                ( C ) STRANDEDNESS: single
                ( D ) TOPOLOGY: linear ( x i ) SEQUENCE DESCRIPTION: SEQ ID NO:40:

GAATATCTGC ATTGCGTGGT G                                                                                            21

( 2 ) INFORMATION FOR SEQ ID NO:41:

( i ) SEQUENCE CHARACTERISTICS:
                ( A ) LENGTH: 21 bases
                ( B ) TYPE: nucleic acid
                ( C ) STRANDEDNESS: single
                ( D ) TOPOLOGY: linear ( x i ) SEQUENCE DESCRIPTION: SEQ ID NO:41:

CTGGTATAGA ACAGCTGTAT G                      21

( 2 ) INFORMATION FOR SEQ ID NO:42:

( i ) SEQUENCE CHARACTERISTICS:
        ( A ) LENGTH: 27 bases
        ( B ) TYPE: nucleic acid
        ( C ) STRANDEDNESS: single
        ( D ) TOPOLOGY: linear ( x i ) SEQUENCE DESCRIPTION: SEQ ID NO:42:

ATTCTTCTAA GGAGCCTAAA TTCACCA                27

( 2 ) INFORMATION FOR SEQ ID NO:43:

( i ) SEQUENCE CHARACTERISTICS:
        ( A ) LENGTH: 21 bases
        ( B ) TYPE: nucleic acid
        ( C ) STRANDEDNESS: single
        ( D ) TOPOLOGY: linear ( x i ) SEQUENCE DESCRIPTION: SEQ ID NO:43:

CCACCATTGC TAGTTAGCTT G                      21

( 2 ) INFORMATION FOR SEQ ID NO:44:

( i ) SEQUENCE CHARACTERISTICS:
        ( A ) LENGTH: 24 bases
        ( B ) TYPE: nucleic acid
        ( C ) STRANDEDNESS: single
        ( D ) TOPOLOGY: linear ( x i ) SEQUENCE DESCRIPTION: SEQ ID NO:44:

ATGGACTCAA GAATGGAAAG AATG                   24

( 2 ) INFORMATION FOR SEQ ID NO:45:

( i ) SEQUENCE CHARACTERISTICS:
        ( A ) LENGTH: 21 bases
        ( B ) TYPE: nucleic acid
        ( C ) STRANDEDNESS: single
        ( D ) TOPOLOGY: linear ( x i ) SEQUENCE DESCRIPTION: SEQ ID NO:45:

CACCACGCAA TGCAGATATT C                      21

( 2 ) INFORMATION FOR SEQ ID NO:46:

( i ) SEQUENCE CHARACTERISTICS:
        ( A ) LENGTH: 21 bases
        ( B ) TYPE: nucleic acid
        ( C ) STRANDEDNESS: single
        ( D ) TOPOLOGY: linear ( x i ) SEQUENCE DESCRIPTION: SEQ ID NO:46:

CTCATGGTCA CTGCTTAGAA G                      21

( 2 ) INFORMATION FOR SEQ ID NO:47:

( i ) SEQUENCE CHARACTERISTICS:
        ( A ) LENGTH: 21 bases
        ( B ) TYPE: nucleic acid
        ( C ) STRANDEDNESS: single
        ( D ) TOPOLOGY: linear ( x i ) SEQUENCE DESCRIPTION: SEQ ID NO:47:

GTTACATAGA GCACCTCACT G                                                                                    21

( 2 ) INFORMATION FOR SEQ ID NO:48:

( i ) SEQUENCE CHARACTERISTICS:
        ( A ) LENGTH: 23 bases
        ( B ) TYPE: nucleic acid
        ( C ) STRANDEDNESS: single
        ( D ) TOPOLOGY: linear ( x i ) SEQUENCE DESCRIPTION: SEQ ID NO:48:

ATGGACCCTA TATTGACAAC ATC                                                                                  23

( 2 ) INFORMATION FOR SEQ ID NO:49:

( i ) SEQUENCE CHARACTERISTICS:
        ( A ) LENGTH: 23 bases
        ( B ) TYPE: nucleic acid
        ( C ) STRANDEDNESS: single
        ( D ) TOPOLOGY: linear ( x i ) SEQUENCE DESCRIPTION: SEQ ID NO:49:

CCTTTAATCT TTGGAACTGG AAC                                                                                  23

( 2 ) INFORMATION FOR SEQ ID NO:50:

( i ) SEQUENCE CHARACTERISTICS:
        ( A ) LENGTH: 21 bases
        ( B ) TYPE: nucleic acid
        ( C ) STRANDEDNESS: single
        ( D ) TOPOLOGY: linear ( x i ) SEQUENCE DESCRIPTION: SEQ ID NO:50:

GGGCTAACAG TGATGCTATT T                                                                                    21

( 2 ) INFORMATION FOR SEQ ID NO:51:

( i ) SEQUENCE CHARACTERISTICS:
        ( A ) LENGTH: 21 bases
        ( B ) TYPE: nucleic acid
        ( C ) STRANDEDNESS: single
        ( D ) TOPOLOGY: linear ( x i ) SEQUENCE DESCRIPTION: SEQ ID NO:51:

GCTTAGAAGT CTGTCTGTGT C                                                                                    21

( 2 ) INFORMATION FOR SEQ ID NO:52:

( i ) SEQUENCE CHARACTERISTICS:
        ( A ) LENGTH: 21 bases
        ( B ) TYPE: nucleic acid
        ( C ) STRANDEDNESS: single
        ( D ) TOPOLOGY: linear ( x i ) SEQUENCE DESCRIPTION: SEQ ID NO:52:

GCTAGATATT GATGAGCCAG A                                                                                    21

( 2 ) INFORMATION FOR SEQ ID NO:53:

( i ) SEQUENCE CHARACTERISTICS:
        ( A ) LENGTH: 21 bases
        ( B ) TYPE: nucleic acid
        ( C ) STRANDEDNESS: single
        ( D ) TOPOLOGY: linear ( x i ) SEQUENCE DESCRIPTION: SEQ ID NO:53:

GCTAAGGCAT GATTTTGTTC A                                                                                    21

(2) INFORMATION FOR SEQ ID NO:54:

(i) SEQUENCE CHARACTERISTICS:
  (A) LENGTH: 21 bases
  (B) TYPE: nucleic acid
  (C) STRANDEDNESS: single
  (D) TOPOLOGY: linear (xi) SEQUENCE DESCRIPTION: SEQ ID NO:54:

GTCGATGTTT GACAGTGAAC T  21

(2) INFORMATION FOR SEQ ID NO:55:

(i) SEQUENCE CHARACTERISTICS:
  (A) LENGTH: 21 bases
  (B) TYPE: nucleic acid
  (C) STRANDEDNESS: single
  (D) TOPOLOGY: linear (xi) SEQUENCE DESCRIPTION: SEQ ID NO:55:

GAAGGAGCTG AGTCAACTCA C  21

(2) INFORMATION FOR SEQ ID NO:56:

(i) SEQUENCE CHARACTERISTICS:
  (A) LENGTH: 21 bases
  (B) TYPE: nucleic acid
  (C) STRANDEDNESS: single
  (D) TOPOLOGY: linear (xi) SEQUENCE DESCRIPTION: SEQ ID NO:56:

GCTTGGCTGT ATGTGTGATT C  21

(2) INFORMATION FOR SEQ ID NO:57:

(i) SEQUENCE CHARACTERISTICS:
  (A) LENGTH: 21 bases
  (B) TYPE: nucleic acid
  (C) STRANDEDNESS: single
  (D) TOPOLOGY: linear (xi) SEQUENCE DESCRIPTION: SEQ ID NO:57:

TACTTCTGTG AGGCAGATGC C  21

TREATMENT OF PARTIAL GROWTH HORMONE INSENSITIVITY SYNDROME

This application is a continuation of Ser. No. 08/410,452, filed Mar. 24, 1995, which is a CIP of application U.S. Ser. No. 08/224,982 filed on 7 Apr. 1994, now U.S. Pat. No. 5,646,113.

BACKGROUND OF THE INVENTION

1. Field of the Invention

This invention relates to a method for increasing the growth rates of human patients having partial growth hormone insensitivity syndrome.

2. Description of Background and Related Art

Most children with significant short stature do not have growth hormone (GH) deficiency as classically defined by the GH response to provocative stimuli. Once known causes of short stature have been excluded, these patients are classified with various terms, including familial short stature, constitutional delay of growth, or "idiopathic" short stature (ISS). Some of these children may not reach their genetic potential for height, although results from large-scale longitudinal studies have not been reported. Since there are so many factors that contribute to normal growth and development, it is likely that patients with ISS are heterogeneous with regard to their etiology of short stature. Despite not being classically GH deficient, most children with ISS respond to treatment with GH, although not as well.

Many investigators have searched for disturbances in spontaneous GH secretion in this set of patients. One hypothesis suggests that some of these patients have inadequate secretion of endogenous GH under physiologic conditions, but are able to demonstrate a rise in GH in response to pharmacologic stimuli, as in traditional GH stimulation tests. This disorder has been termed "GH neurosecretory dysfunction," and the diagnosis rests on the demonstration of an abnormal GH pattern on prolonged serum sampling. Numerous investigators have reported results of such studies, and have found this abnormality to be only occasionally present. Other investigators have postulated that these patients have "bioinactive GH;" however, this has not yet been demonstrated conclusively.

When the GH receptor (GHR) was cloned, it was shown that the major GH binding activity in blood was due to a protein which derives from the same gene as the GHR and corresponds to the extracellular domain of the full-length GHR. Most patients with growth hormone insensitivity (or Laron) syndrome (GHIS) lack growth hormone receptor binding activity and have absent or very low GH-binding protein (GHBP) activity in blood. Such patients have a mean height standard deviation score (SDS) of about −5 to −6, are resistant to GH treatment, and have increased serum concentrations of GH and low serum concentrations of insulin-like growth factor (IGF-I). They respond to treatment with IGF-I. In patients with defects in the extracellular domain of the GHR, the lack of functional GHBP in the circulation can serve as a marker for the GH insensitivity.

There is a subclass of patients with ISS having low GHBP in their blood who have a mean height SDS intermediate between patients with complete GHIS (Laron syndrome) and normal children, and who respond somewhat, but not completely, to GH treatment. This class of patients can be characterized as having partial GHIS.

It is an object of the present invention to identify a subset of patients with ISS who exhibit partial GHIS and do not have complete GHIS or Laron syndrome.

It is another object to treat this identified subset of patients so that they attain ultimate height consistent with their genetic potential as determined by the mid-parental target height.

These and other objects will be apparent to those of ordinary skill in the art.

SUMMARY OF THE INVENTION

Accordingly, in one aspect, the present invention provides a method for increasing the growth rate of a human patient having partial GHIS comprising administering an effective amount of GH to said patient, whereby said patient has a height less than about −2 standard deviations below normal for age and sex, has a serum level of high-affinity GHBP that is at least 2 standard deviations below normal levels, has a serum level of IGF-I that is below normal mean levels, and has a mean or maximum stimulated serum level of GH that is at least normal, wherein the patient does not have Laron syndrome. Preferably, the GH is human recombinant GH.

In another aspect, the invention provides a method for increasing the growth rate of a human patient having partial GHIS comprising administering an effective amount of IGF-I (preferably human recombinant IGF-I) to said patient, whereby said patient has a height less than about −2 standard deviations below normal for age and sex, has a serum level of high-affinity GHBP that is at least 2 standard deviations below normal levels, has a serum level of IGF-I that is below normal mean levels, and has a mean or maximum stimulated serum level of GH that is at least normal, wherein the patient does not have Laron syndrome.

In a further aspect, the invention supplies a method for increasing the growth rate of a human patient having partial GHIS comprising administering amounts of IGF-I and GH to said patient which amounts are effective in combination, whereby said patient has a height less than about −2 standard deviations below normal for age and sex, has a serum level of high-affinity GHBP that is at least 2 standard deviations below normal levels, has a serum level of IGF-I that is below normal mean levels, and has a mean or maximum stimulated serum level of GH that is at least normal, wherein the patient does not have Laron syndrome.

BRIEF DESCRIPTION OF THE DRAWINGS

FIG. 4 shows the first-year annualized growth rate (cm/yr) by GHBP SDS for patients treated with human GH (hGH) who remained prepubertal during the first year of GH therapy (n=166). The shaded area represents the normal range for GHBP (−2 SDS to +2 SDS).

FIG. 5 is a graph of pre-treatment, first-year treatment, and second-year treatment growth rates for patients whose data is set forth in Table VII of Example III below having a GHBP SDS −2 (n=14) (squares) or a GHBP SDS >−2 (n=29) (circles).

FIG. 8 shows the DNA sequences (SEQ ID NOS: 1 and 2, respectively) and predicted amino acid sequences (SEQ ID NOS: 3 and 4, respectively) of two GHR alleles in ISS Patient 4 (exons 4–6). The mutations in alleles 1 and 2 are boxed. The vertical bars indicate exon boundaries in the cDNA sequence.

FIG. 9 shows the DNA sequences (SEQ ID NOS: 5 and 6, respectively) and predicted amino acid sequences (SEQ ID NOS: 7 and 8, respectively) of two GHR alleles in ISS Patient 2 (exon 5). The mutation in allele 2 is boxed.

FIG. 10 shows the DNA sequences (SEQ ID NOS: 9 and 10, respectively) and predicted amino acid sequences (SEQ ID NOS: 11 and 12, respectively) of two GHR alleles in ISS Patient 1 (exon 7). The mutation in allele 2 is boxed. The intron sequence is given in lower-case letters and the exon sequence in upper-case lettering. The vertical bars indicate exon boundaries in the DNA sequence.

FIG. 11 shows the DNA sequences (SEQ ID NOS: 13 and 14, respectively) and predicted amino acid sequences (SEQ ID NOS: 15 and 16, respectively) of two GHR alleles in ISS Patient 7 (exon 7). The mutation in allele 2 is boxed. The intron sequence is given in lower-case letters and the exon sequence in upper-case lettering. The vertical bars indicate exon boundaries in the DNA sequence.

DESCRIPTION OF THE PREFERRED EMBODIMENTS

Figure 1A:
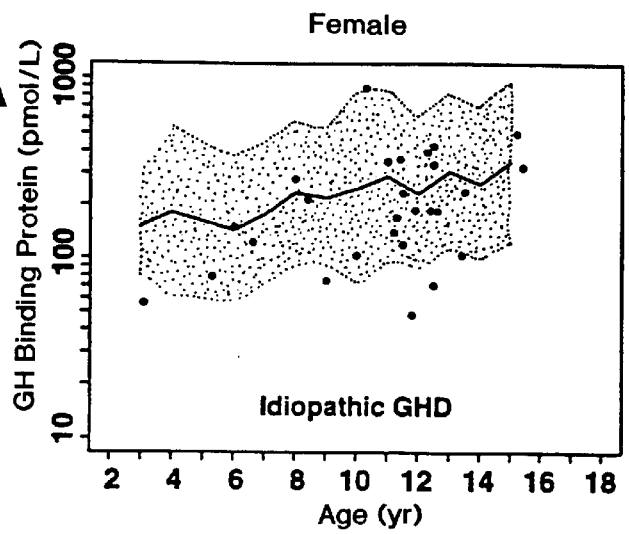
FIGS. 1A–1E show serum GHBP concentrations in children in the Genentech National Cooperative Growth Study (NCGS) with growth hormone deficiency (GHD) FIGS. 1A–1B, ISS FIGS. 1C–1D, and Turner syndrome (TS) FIG. 1E standardized for age and sex and expressed as SDS, by age at the time of enrollment in the study. The shaded area represents the normal range (−2 SD to +2 SD) for each sex. The solid line indicates the normal mean for age and sex. Occasionally, points for two or more patients overlap and appear as a single point.
Figure 1B:
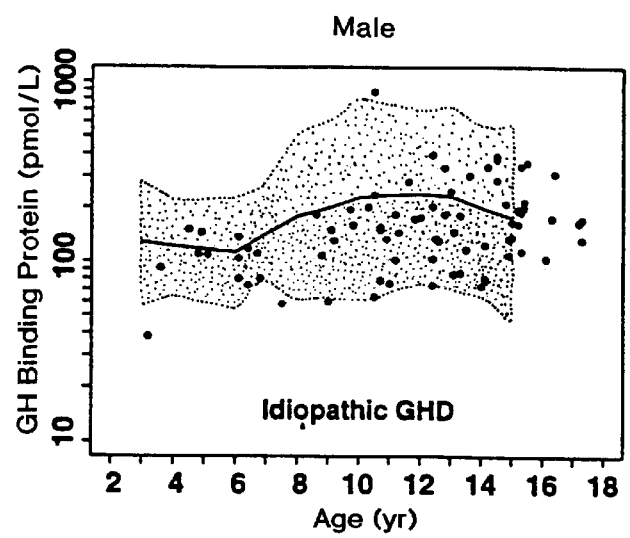
Figure 1C:
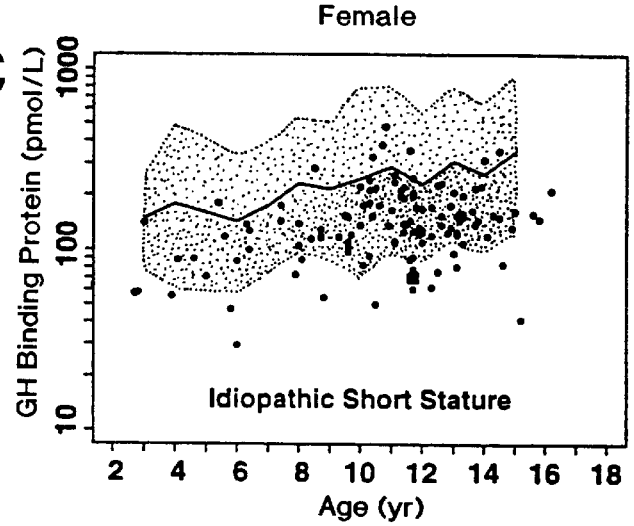
Figure 1D:
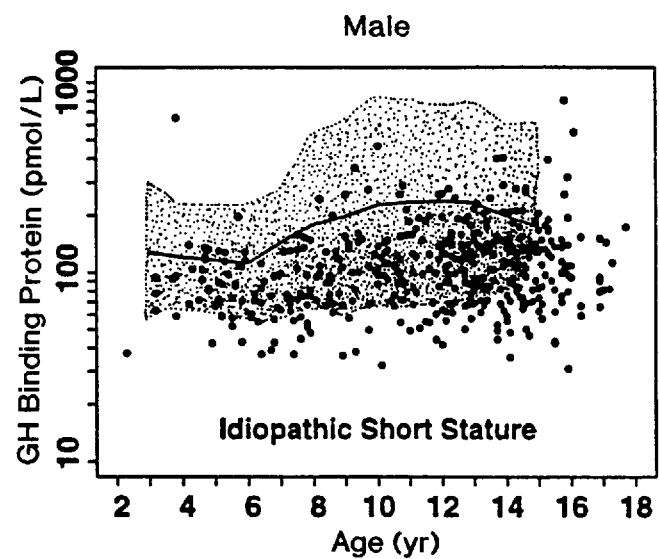
Figure 1E:
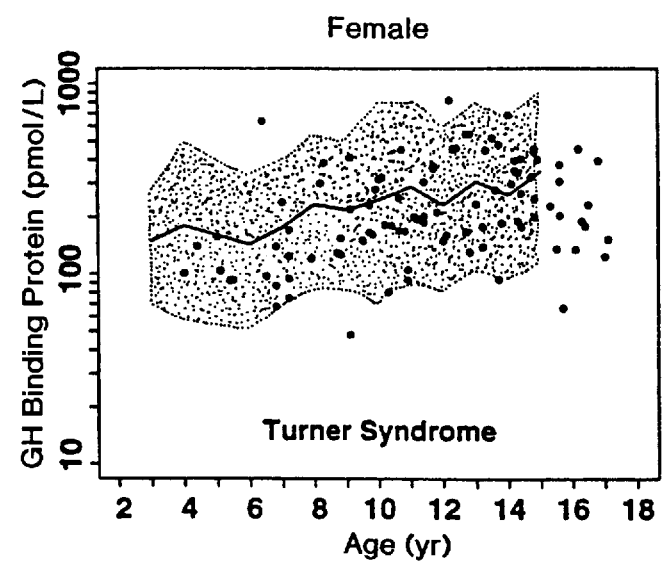

Definitions:

The patient population treated by the method of this invention excludes patients with "Laron syndrome," otherwise known and defined herein as people with complete lack of GHR function or complete GHIS. These patients attain an adult height of only 110–130 cm. Additional common symptoms include small face and jaw, depressed nasal bridge, frontal bossing, obesity, high-pitched voice, and hypoglycemia in early childhood. Biochemically, they are characterized by having increased serum concentrations of GH but low serum concentrations of IGF-I.

"Increasing the growth rate of a human patient" includes not only the situation where the patient attains at least the same ultimate height as GH-deficient patients treated with GH (i.e., patients diagnosed with GHD), but also refers to a situation where the patient catches up in height at the same growth rate as GH-deficient patients treated with GH, or achieves adult height that is within the target height range, i.e., an ultimate height consistent with their genetic potential as determined by the mid-parental target height.

"Partial growth hormone insensitivity syndrome", or "partial GHIS" refers to a syndrome wherein the patient responds to the same doses of GH as that given to GH-deficient patients, but does not respond as well. This syndrome is further characterized in that the patient has a height of less than about −2 standard deviations below normal for age and sex, preferably in the range of less than about −2 to about −4 standard deviations below normal for age and sex, has a serum level of high-affinity GHBP that is at least 2 standard deviations (typically 2–4 standard deviations) below the normal level for humans, has a serum level of IGF-I that is below the normal mean level for humans, and has a mean or maximum stimulated serum level of GH that is at least normal for humans. Mean serum levels are the mean of measurements in the patient.

As used herein, "non-GH-deficient short stature" refers to a patient who has a height SDS of about ≦2 SD below normal for age and sex and does not have GHD (as classically defined based on secreting levels of GH below a minimum threshold level).

As used herein, "growth hormone" or "GH" refers to growth hormone in native-sequence or in variant form, and from any source, whether natural, synthetic, or recombinant. Examples include human growth hormone (hGH), which is natural or recombinant GH with the human native sequence (somatotropin or somatropin), and recombinant growth hormone (rGH), which refers to any GH or GH variant produced by means of recombinant DNA technology, including somatrem, somatotropin, and somatropin. Preferred herein for human use is recombinant human native-sequence, mature GH with or without a methionine at its N-terminus. More preferred is methionyl human growth hormone (met-hGH) produced in *E. coli*, e.g., by the process described in U.S. Pat. No. 4,755,465 issued Jul. 5, 1988 and Goeddel et al., *Nature*, 282: 544 (1979). Met-hGH, which is sold under the trademark PROTROPIN® by Genentech, Inc., is identical to the natural polypeptide, with the exception of the presence of an N-terminal methionine residue. This added amino acid is a result of the bacterial protein synthesis process. Also preferred is recombinant hGH available from Genentech, Inc. under the trademark NUTROPIN®. This latter hGH lacks this methionine residue and has an amino acid sequence identical to that of the natural hormone. See Gray et al., *Biotechnology* 2: 161 (1984). Both methionyl hGH and hGH have equivalent potencies and pharmacokinetic values. Moore et al., *Endocrinology*, 122: 2920–2926 (1988). Another appropriate hGH candidate is an hGH variant that is a placental form of GH with pure somatogenic and no lactogenic activity as described in U.S. Pat. No. 4,670,393 issued 2 Jun. 1987. Also included are GH variants as described in WO 90/04788 published 3 May 1990 and WO 92/09690 published 11 Jun. 1992.

As used herein, "IGF-I" refers to insulin-like growth factor-I from any species, including bovine, ovine, porcine, equine, avian, and preferably human, in native-sequence or in variant form, and from any source, whether natural, synthetic, or recombinant. IGF-I has been isolated from human serum and produced recombinantly. See, e.g., EP 123,228 and 128,733.

Preferred herein for human use is human native-sequence, mature IGF-I, more preferably without a N-terminal methionine, prepared, e.g., by the process described in EP 230,869 published Aug. 5, 1987; EP 128,733 published Dec. 19, 1984; or EP 288,451 published Oct. 26, 1988. More preferably, this native-sequence IGF-I is recombinantly produced and is available from Genentech, Inc., South San Francisco, Calif. for clinical investigations.

The preferred IGF-I variants are those described in U.S. Pat. No. 5,077,276 issued Dec. 31, 1991, in PCT WO 87/01038 published Feb. 26, 1987 and in PCT WO 89/05822 published Jun. 29, 1989, i.e., those wherein at least the glutamic acid residue is absent at position 3 from the N-terminus of the mature molecule or those having a deletion of up to five amino acids at the N-terminus. The most preferred variant has the first three amino acids from the N-terminus deleted (variously designated as brain IGF, tIGF-I, des(1–3)-IGF-I, or des-IGF-I).

"High-affinity growth hormone binding protein" or "high-affinity GHBP" refers to the extracellular domain of the GHR that circulates in blood and functions as a GHBP in several species (Ymer and Herington, *Mol. Cell. Endocrino.,* 41: 153 [1985]; Smith and Talamantes, *Endocrinology,* 123: 1489–1494 [1988]; Emtner and Roos, *Acta Endocrinologica (Copenh.),* 122: 296–302 [1990]), including man. Baumann et al., *J. Clin. Endocrinol. Metab.,* 62: 134–141 (1986); EP 366,710 published 9 May 1990; Herington et al., *J. Clin. Invest.,* 77: 1817–1823 (1986); Leung et al., *Nature,* 330: 537–543 (1987). A second BP with lower affinity for GH has also been described that appears to be structurally unrelated to the GHR. Baumann and Shaw, *J. Clin. Endocrinol. Metab.,* 70: 680–686 (1990). Various methods exist for measuring functional GHBP in serum, with the preferred method being a ligand-mediated immunofunctional assay (LIFA) described by Carlsson et al., *J C E M,* 73: 1216 (1991) and U.S. Pat. No. 5,210,017.

Modes for Carrying Out the Invention:

The subpopulation of patients targeted for treatment by the current invention consists of those patients with partial GHIS as defined above. The patient must exhibit each of the clinical signs set forth to be treatable by the method claimed herein.

The GH and/or IGF-I is directly administered to the patient by any suitable technique, including parenterally, intranasally, intrapulmonary, orally, or by absorption through the skin. If they are administered together, they need not be administered by the same route. They can be administered locally or systemically. Examples of parenteral administration include subcutaneous, intramuscular, intravenous, intraarterial, and intraperitoneal administration. Preferably, they are administered by daily subcutaneous injection.

The GH and/or IGF-I to be used in the therapy will be formulated and dosed in a fashion consistent with good medical practice, taking into account the clinical condition of the individual patient (especially the side effects of treatment with GH or IGF-I alone), the site of delivery of the IGF-I and GH composition(s), the method of administration, the scheduling of administration, and other factors known to practitioners. The "effective amounts" of each component for purposes herein are thus determined by such considerations and are amounts that increase the growth rates of the patients.

If GH is administered alone, a dose of greater than about 0.2 mg/kg/week is preferably employed, more preferably greater than about 0.25 mg/kg/week, and even more preferably greater than or equal to about 0.3 mg/kg/week. In one embodiment, the dose of GH ranges from about 0.3 to 1.0 mg/kg/week, and in another embodiment, 0.35 to 1.0 mg/kg/week. Preferably, the GH is administered once per day subcutaneously.

The GH is suitably administered continuously or non-continuously, such as at particular times (e.g., once daily) in the form of an injection of a particular dose, where there will be a rise in plasma GH concentration at the time of the injection, and then a drop in plasma GH concentration until the time of the next injection. Another non-continuous administration method results from the use of PLGA microspheres and many implant devices available that provide a discontinuous release of active ingredient, such as an initial burst, and then a lag before release of the active ingredient. See, e.g., U.S. Pat. No. 4,767,628, col. 2, lines 19–37.

The GH may also be administered so as to have a continual presence in the blood that is maintained for the duration of the administration of the GH. This is most preferably accomplished by means of continuous infusion via, e.g., mini-pump such as an osmotic mini-pump. Alternatively, it is properly accomplished by use of frequent injections of GH (i.e., more than once daily, for example, twice or three times daily).

In yet another embodiment, GH may be administered using long-acting GH formulations that either delay the clearance of GH from the blood or cause a slow release of GH from, e.g., an injection site. The long-acting formulation that prolongs GH plasma clearance may be in the form of GH complexed, or covalently conjugated (by reversible or irreversible bonding) to a macromolecule such as one or more of its binding proteins (WO 92/08985 published 29 May 1992) or a water-soluble polymer selected from PEG and polypropylene glycol homopolymers and polyoxyethylene polyols, i.e., those that are soluble in water at room temperature. Alternatively, the GH may be complexed or bound to a polymer to increase its circulatory half-life. Examples of polyethylene polyols and polyoxyethylene polyols useful for this purpose include polyoxyethylene glycerol, polyethylene glycol, polyoxyethylene sorbitol, polyoxyethylene glucose, or the like. The glycerol backbone of polyoxyethylene glycerol is the same backbone occurring in, for example, animals and humans in mono-, di-, and triglycerides.

The polymer need not have any particular molecular weight, but it is preferred that the molecular weight be between about 3500 and 100,000, more preferably between 5000 and 40,000. Preferably the PEG homopolymer is unsubstituted, but it may also be substituted at one end with an alkyl group. Preferably, the alkyl group is a C1–C4 alkyl group, and most preferably a methyl group. Most preferably, the polymer is an unsubstituted homopolymer of PEG, a monomethyl-substituted homopolymer of PEG (mPEG), or polyoxyethylene glycerol (POG) and has a molecular weight of about 5000 to 40,000.

The GH is covalently bonded via one or more of the amino acid residues of the GH to a terminal reactive group on the polymer, depending mainly on the reaction conditions, the molecular weight of the polymer, etc. The polymer with the reactive group(s) is designated herein as activated polymer. The reactive group selectively reacts with free amino or other reactive groups on the GH. It will be understood, however, that the type and amount of the reactive group chosen, as well as the type of polymer employed, to obtain optimum results, will depend on the particular GH employed to avoid having the reactive group react with too many particularly active groups on the GH. As this may not be possible to avoid completely, it is recommended that generally from about 0.1 to 1000 moles, preferably 2 to 200 moles, of activated polymer per mole of protein, depending on protein concentration, is employed. The final amount of activated polymer per mole of protein is a balance to maintain optimum activity, while at the same time optimizing, if possible, the circulatory half-life of the protein.

While the residues may be any reactive amino acids on the protein, such as one or two cysteines or the N-terminal amino acid group, preferably the reactive amino acid is lysine, which is linked to the reactive group of the activated polymer through its free epsilon-amino group, or glutamic or aspartic acid, which is linked to the polymer through an amide bond.

The covalent modification reaction may take place by any appropriate method generally used for reacting biologically active materials with inert polymers, preferably at about pH 5–9, more preferably 7–9 if the reactive groups on the GH are lysine groups. Generally, the process involves preparing an activated polymer (with at least one terminal hydroxyl group), preparing an active substrate from this polymer, and thereafter reacting the GH with the active substrate to produce the GH suitable for formulation. The above modification reaction can be performed by several methods, which may involve one or more steps. Examples of modifying agents that can be used to produce the activated polymer in a one-step reaction include cyanuric acid chloride (2,4,6-trichloro-S-triazine) and cyanuric acid fluoride.

In one embodiment the modification reaction takes place in two steps wherein the polymer is reacted first with an acid anhydride such as succinic or glutaric anhydride to form a carboxylic acid, and the carboxylic acid is then reacted with a compound capable of reacting with the carboxylic acid to form an activated polymer with a reactive ester group that is capable of reacting with the GH. Examples of such compounds include N-hydroxysuccinimide, 4-hydroxy-3-nitrobenzene sulfonic acid, and the like, and preferably N-hydroxysuccinimide or 4-hydroxy-3-nitrobenzene sulfonic acid is used. For example, monomethyl substituted PEG may be reacted at elevated temperatures, preferably about 100°–110° C. for four hours, with glutaric anhydride. The monomethyl PEG-glutaric acid thus produced is then reacted with N-hydroxysuccinimide in the presence of a carbodiimide reagent such as dicyclohexyl or isopropyl carbodiimide to produce the activated polymer, methoxypolyethylene glycolyl-N-succinimidyl glutarate, which can then be reacted with the GH. This method is described in detail in Abuchowski et al., *Cancer Biochem. Biophys.,* 7: 175–186 (1984). In another example, the monomethyl substituted PEG may be reacted with glutaric anhydride followed by reaction with 4-hydroxy-3-nitrobenzene sulfonic acid (HNSA) in the presence of dicyclohexyl carbodiimide to produce the activated polymer. HNSA is described by Bhatnagar et al., *Peptides: Synthesis-Structure-Function, Proceedings of the Seventh American Peptide Symposium,* Rich et al. (eds.) (Pierce Chemical Co., Rockford, Ill., 1981), p. 97–100, and in Nitecki et al., *High-Technology Route to Virus Vaccines* (American Society for Microbiology: 1986) entitled "Novel Agent for Coupling Synthetic Peptides to Carriers and Its Applications."

Specific methods of producing GH conjugated to PEG include the methods described in U.S. Pat. No. 4,179,337 on PEG-GH and U.S. Pat. No. 4,935,465, which discloses PEG reversibly but covalently linked to GH. Other specific methods for producing PEG-GH include the following:

PEGylation with methoxypolyethylene glycol aldehyde (Me-PEG aldehyde) by reductive alkylation and purification is accomplished by adding to 2 mg/mL of GH in phosphate-buffered saline (PBS) pH 7.0, 5 mM of Me-PEG aldehyde-5000 (molecular weight 5000 daltons) and 20 mM of NaCNBH3 and gently mixing at room temperature for 3 hours. Ethanolamine is then added to 50 mM to reductively amidate the remaining unreacted Me-PEG. The mixture is separated on an anion-exchange column, FPLC Mono Q. The surplus unreacted Me-PEG does not bind to the column and can then be separated from the mixture. Two main PEGylated GH fractions are obtained with apparent molecular weights of 30K and 40K on reduced SDS-PAGE, vs. 20K of the unreacted GH. GH-GHBP complex is PEGylated in the same manner to give a derivative of 150K by gel filtration.

PEGylation with N-hydroxysuccinimidyl PEG (NHS-PEG) and purification are accomplished by adding NHS-PEG at a 5-fold molar excess of the total lysine concentration of GH to a solution containing 2 mg/mL of GH in 50 mM of sodium borate buffer at pH 8.5 or PBS at pH 7, and mixing at room temperature for one hour. Products are separated on a Superose 12 sizing column and/or Mono Q of FPLC. The PEGylated GH varies in size depending on the pH of the reaction from approximately 300K for the reaction run at pH 8.5 to 40K for pH 7.0 as measured by gel filtration. The GH-GHBP complex is also PEGylated the same way with a resulting molecular weight of 400 to 600 Kd from gel filtration.

PEGylation of the cysteine mutants of GH with PEG-maleimide is accomplished by preparing a single cysteine mutant of GH by site-directed mutagenesis, secreting it from an *E. coli* 16C9 strain (W3110 ΔtonA phoA ΔE15 Δ(argF-lac)169 deoC2 that does not produce the deoC protein), and purifying it on an anion-exchange column.

Strain 16C9 was constructed genetically by transferring the deoC2 allele from strain CGSC#6092 (No. 6092, available from the *E. coli* Genetic Stock Center, New Haven, Conn. and described in Mark et al., *Molec. Gen. Genet.,* 155: 145–152 (1977), with genotype trxA1 recA1 ilvE720::tn5 metE70 deoC2 lacZ53 rha5 malB45 rpsL151) into a strain designated 7C1.

Strain 7C1 [with genotype W3110 ΔtonA phoA AE15 Δ(argF-lac)169] was constructed in several steps using techniques involving transductions with phage P1Kc, derived from P1 (J. Miller, *Experiments in Molecular Genetics* [Cold Spring Harbor, N.Y.: Cold Spring Harbor Laboratory, 1972]), and transposon genetics (Kleckner et al., *J. Mol. Biol.,* 116: 125–159 [1977]). *E. coli* K12 W3110, which is a K12 strain that is F–, λ– (the wild type is F+, λ+) (Bachmann, *Bact. Rev.,* 36: 525–557 [1972]), was used as the starting host.

First, the tonA gene (fhuA) (Kadner et al., *J. Bact.,* 143: 256–264 [1980]; Bachmann, *Microbiol. Rev.,* 47: 180–230 [1983]) was deleted by the insertion and subsequent imprecise excision of a Tn10 transposon into the tonA gene.

In the first step of this procedure, *E. coli* W3110 was transduced with A::Tn10 to generate a Tn10 hop pool of *E. coli* W3110 (Kleckner et al., *J. Mol. Biol.,* supra).

The *E. coli* W3110::Tn10 hop pool was grown in L broth at 37° C. to a cell density of about $1\times10^9$/mL. A total of 0.5 mL of the culture was centrifuged and the pellet was resuspended in 0.2 mL of a λphi80 lysate containing $7.0\times10^9$ pfu. The phage was allowed to adsorb for 30 minutes at 37° C. The suspension was then spread on EMB plates supplemented with tetracycline (15 µg/mL). After an overnight incubation at 37° C., the colonies were pooled in 3 mL of L broth, grown overnight at 37° C., washed twice, and resuspended in L broth. A bacteriophage P1kc lysate was made on this culture (Miller, J. H., *Experiments in Molecular Biology,* supra, page 304).

*E. coli* AT982 (no. 4546, *E. coli* Genetic Stock Center, New Haven, Conn.) was transduced to tetracycline resistance by this P1kc lysate. Transductants were selected on L broth plates supplemented with tetracycline (15 µg/mL) and 40 µg/mL diaminopimelic acid (dap). The resulting transductants were screened for tetracycline resistance and the regeneration of the dap gene (dap+, tet$^R$). dap+, tet$^R$ transductants were then tested for λphi80 resistance.

P1kc lysates were then made on several dap+, tet$^R$, λhi80-resistant strains. The lysates were used to transduce *E. coli* W3110 to tetracycline resistance. The transductants were screened and selected for λphi80 resistance.

Tetracycline-sensitive isolates were selected from the W3110 tonA::Tn10-λphi80R transductants. Maloy and Nunn, *J. Bacteriol.*, 145: 1110 (1981). These isolates were checked for λphi80 resistance and tetracycline sensitivity after single colony purification.

DNA was isolated from several tetracycline-sensitive λphi80-resistant mutants and digested with SstII. The SstII-digested DNA was characterized by the Southern blot procedure using radioactively labeled and SstII-digested λ::Tn10 DNA as a probe to determine if the Tn10 had been excised. Davis et al., *Advanced Bacterial Genetics* (Cold Spring Harbor Laboratory, New York, 1980). One of the tetracycline-sensitive isolates was shown to have lost two of the Tn10 hydridization bands as compared to the hybridization between DNA from the λ::Tn10 and the parental W3110 tonA::Tn10λphi80R. A third hybridization band had an altered mobility, indicating that a deletion caused by the imprecise excision of Tn10 had occurred.

SDS-gel electrophoresis of outer membrane preparations from the strain with an imprecise Tn10 excision revealed that the band assumed to be the TonA protein had an altered electrophoretic mobility as compared to the wild-type TonA protein. The resulting protein was non-functional as a λphi80 phage receptor protein. A second independent strain that also had undergone imprecise excision of Tn10 showed no TonA protein on the SDS gel.

Neither of these strains demonstrated reversion to tetracycline resistance or to λphi80 susceptibility, indicating that there was an imprecise excision of all or part of the Tn10 transposon together with either a partial or complete deletion of the tonA gene. Thus, the TonA protein (MW 78,000) was eliminated from the outer membrane, rendering the W3110 tonA strain resistant to several bacteriophages.

Then, two more deletion mutations, phoA Δ E15 (Sarthy et al., *J. Bact.*, 145: 288–292 [1981]) and Δ (argF-lac)-169 (Schweizer et al., *Mol. Gen. Genet.*, 192: 293–294 [1983]), were simultaneously transferred into W3110 tonA by genetic linkage to a kanamycin-resistance transposon inserted into a proline biosynthetic gene (proC::Tn5).

The transposon was eliminated by selecting for a spontaneous prototrophic (pro$^+$) revertant on glucose minimal agar plates. The introduction of the phoA mutation was recognized as transductants that form white colonies on glucose-minimal agar plates with 0.2 mM phosphate and 20 mg/L 5-bromo-4-chloro-3-indolyl phosphate. Likewise, the Δ(argF-lac)169 mutation causes the loss of the enzyme beta-galactosidase and results in cells that form white colonies on MacConkey-1% lactose agar plates. The result was strain 7C1.

Finally, the deoC mutation (Bachmann, supra), removing the aldolase, was introduced into 7C1 by a multistep process of transductions using phage P1kc. Standard methods for transduction were utilized. First, threonine auxotrophy was introduced into 7C1 to provide a means for positive selection of transduced chromosomal segments in the region of the deoC gene as follows.

P1kc was grown on a threonine auxotroph, such auxotrophs being described in Clare N. Berg and Douglas E. Berg, *Microbioloy*-1981, "Bacterial Transposons", pp. 107–116 (Amer. Soc. for Microbiology, Washington, DC, 1981).

The resulting lysate was used to transduce strain 7C1 to tetracycline resistance, selecting for transductants on LB plates containing 25 μg/mL tetracycline. The resulting strain, designated 14A9 (tonAΔ, phoAΔE15, Δ(argF-lac)169 thr::tn10), reverted spontaneously to prototrophy at a high frequency, so fusaric acid plates (*J. Bact.*, 145: 1110 [1981]) were used to select a stable tetracycline-sensitive threonine auxotroph, designated strain 16C4.

P1kc was grown on Strain CGSC#6092, described supra.

The resulting lysate was used to transduce strain 16C4 to prototrophy, selecting for growth on glucose minimal agar plates. To obtain a high-frequency transducing lysate from strain 2D4, the P1kc phage had to be cycled for growth two times on this host. Five prototrophic transductants of strain 16C4 were isolated, purified, and tested for growth on thymidine minimal agar plates. Four out of five of these isolates could not grow on thymidine and therefore had received the deoC2 mutation that eliminates synthesis of the deoC protein. One of these four isolates was saved and was designated strain 16C9 (ΔtonA, phoA, Δ6E15, Δ(argF-lac) 169, deoC2).

PEG-maleimide is made by reacting monomethoxyPEG amine with sulfo-MBs in 0.1M sodium phosphate pH 7.5 for one hour at room temperature and buffer exchanged to phosphate buffer pH 6.2. Next GH with a free extra cysteine is mixed in for one hour and the final mixture is separated on a Mono Q column as in Me-PEG aldehyde PEGylated GH.

As ester bonds are chemically and physiologically labile, it may be preferable to use a PEG reagent in the conjugating reaction that does not contain ester functionality. For example, a carbamate linkage can be made by reacting PEG-monomethyl ether with phosgene to give the PEG-chloroformate. This reagent could then be used in the same manner as the NHS ester to functionalize lysine side-chain amines. In another example, a urea linkage is made by reacting an amino-PEG-monomethyl ether with phosgene. This would produce a PEG-isocyanate that will react with lysine amines.

A preferred manner of making PEG-GH, which does not contain a cleavable ester in the PEG reagent, is described as follows:

Methoxypoly(ethylene glycol) is converted to a carboxylic acid by titration with sodium naphthalene to generate the alkoxide, followed by treatment with bromoethyl acetate to form the ethyl ester, followed by hydrolysis to the corresponding carboxylic acid by treatment with sodium hydroxide and water, as reported by Buckmann et al., *Macromol. Chem.*, 182: 1379–1384 (1981). The resultant carboxylic acid is then converted to a PEG-N-hydroxysuccinimidyl ester suitable for acylation of GH by reaction of the resultant carboxylic acid with dicyclohexylcarbodiimide and NHS in ethyl acetate.

The resultant NHS-PEG reagent is then reacted with 12 mg/mL of GH using a 30-fold molar excess over GH in a sodium borate buffer, pH 8.5, at room temperature for one hour and applied to a Q Sepharose column in TRIS buffer and eluted with a salt gradient. Then it is applied to a second column (phenyl Toyopearl) equilibrated in 0.3M sodium citrate buffer, pH 7.8. The PEGylated GH is then eluted with a reverse salt gradient, pooled, and buffer-exchanged using a G25 desalting column into a mannitol, glycine, and sodium phosphate buffer at pH 7.4 to obtain a suitable formulated PEG7-GH.

The PEGylated GH molecules and GH-GHBP complex can be characterized by SDS-PAGE, gel filtration, NMR, tryptic mapping, liquid chromatography-mass spectrophotometry, and in vitro biological assay. The extent of PEGylation is suitably first shown by SDS-PAGE and gel filtration and then analyzed by NMR, which has a specific resonance peak for the methylene hydrogens of PEG. The number of PEG groups on each molecule can be calculated from the NMR spectrum or mass spectrometry. Polyacrylamide gel electrophoresis in 10% SDS is appropriately run in 10 mM Tris-HCl pH 8.0, 100 mM NaCl as elution buffer. To demonstrate which residue is PEGylated, tryptic mapping can be performed. Thus, PEGylated GH is digested with trypsin at the protein/enzyme ratio of 100 to 1 in mg basis at 37° C. for 4 hours in 100 mM sodium acetate, 10 mM Tris-HCl, 1 mM calcium chloride, pH 8.3, and acidified to pH <4 to stop digestion before separating on HPLC Nucleosil C-18 (4.6 mm×150 mm, 5µ, 100 Å). The chromatogram is compared to that of non-PEGylated starting material. Each peak can then be analyzed by mass spectrometry to verify the size of the fragment in the peak. The fragment(s) that carried PEG groups are usually not retained on the HPLC column after injection and disappear from the chromatograph. Such disappearance from the chromatograph is an indication of PEGylation on that particular fragment that should contain at least one lysine residue. PEGylated GH may then be assayed for its ability to bind to the GHBP by conventional methods.

The various PEGylation methods used produced various kinds of PEGylated wild-type GH, with apparent molecular weights of 35K, 51K, 250K, and 300K by size exclusion chromatography, which should be close to their native hydrodynamic volume. These were designated PEG1-GH, PEG2-GH, PEG3-GH, and PEG7-GH, respectively. From the results of the tryptic mapping, the PEG1-GH and PEG2-GH both had the N-terminal 9-amino-acid fragment missing from the chromatogram and possibly PEGylated, which could be confirmed by the mass spectrometry of the big molecular species found in the flow-through of the liquid chromatograph. From the molecular weight on SDS-PAGE, PEG1-GH may have one PEG on the N-terminal amine, and the PEG2-GH may have two PEG molecules on the N-terminal amine, forming a tertiary amide. The PEG3-GH has about 5 PEG groups per molecule based upon the NMR result, and on the tryptic map, at least five peptide fragments were missing, suggesting that they are PEGylated. The PEG7-GH molecule is believed to have 6–7 PEG groups per molecule based on mass spectrometry.

The sites for adding PEG groups to GH, and those that are preferred residues for such conjugation, are N-terminal methionine or phenylalanine, lysine 38, lysine 41, lysine 70, lysine 140, lysine 145, lysine 158, and lysine 168. Two lysines that appeared not to be PEGylated were lysine 115 and lysine 172.

The GH is also suitably administered by sustained-release systems. Examples of sustained-release compositions useful herein include semi-permeable polymer matrices in the form of shaped articles, e.g., films, or microcapsules. Sustained-release matrices include polylactides (U.S. Pat. No. 3,773, 919, EP 58,481), copolymers of L-glutamic acid and gamma-ethyl-L-glutamate (Sidman et al., *Biopolymers,* 22: 547–556 [1983]), poly(2-hydroxyethyl methacrylate) (Langer et al., *J. Biomed. Mater. Res.,* 15: 167–277 [1981]; Langer, *Chem. Tech.,* 12: 98–105 [1982]), ethylene vinyl acetate (Langer et al., supra) or poly-D-(−)-3-hydroxybutyric acid (EP 133,988), or PLGA microspheres.

Sustained-release GH compositions also include liposomally entrapped GH. Liposomes containing GH are prepared by methods known per se: DE 3,218,121; Epstein et al., *Proc. Natl. Acad. Sci. USA,* 82: 3688–3692 (1985); Hwang et al., *Proc. Natl. Acad. Sci. USA,* 77: 4030–4034 (1980); EP 52,322; EP 36,676; EP 88,046; EP 143,949; EP 142,641; Japanese Pat. Appln. 83-118008; U.S. Pat. Nos. 4,485,045 and 4,544,545; and EP 102,324. ordinarily, the liposomes are of the small (about 200–800 Angstroms) unilamellar type in which the lipid content is greater than about 30 mol. percent cholesterol, the selected proportion being adjusted for the optimal therapy. In addition, a biologically active sustained-release formulation can be made from an adduct of the GH covalently bonded to an activated polysaccharide as described in U.S. Pat. No. 4,857,505 issued Aug. 15, 1989. In addition, U.S. Pat. No. 4,837,381 describes a microsphere composition of fat or wax or a mixture thereof and GH for slow release.

In another embodiment, the patients identified above are treated with an effective amount of IGF-I. As a general proposition, the total pharmaceutically effective amount of IGF-I administered parenterally per dose will be in the range of about 50 to 240 µg/kg/day, preferably 100 to 200 µg/kg/day, of patient body weight, although, as noted above, this will be subject to a great deal of therapeutic discretion. Also, preferably the IGF-I is administered once or twice per day by subcutaneous injection.

The IGF-I may be administered by any means, including injections (single or multiple, e.g., 1–4 per day) or infusions. As with the GH, the IGF-I may be formulated so as to have a continual presence in the blood during the course of treatment, as described above for GH. Thus, it may be covalently attached to a polymer or made into a sustained-release formulation as described above.

In addition, the IGF-I is appropriately administered together with any one or more of its binding proteins, for example, those currently known, i.e., IGFBP-1, IGFBP-2, IGFBP-3, IGFBP-4, IGFBP-5, or IGFBP-6. The IGF-I may also be coupled to a receptor or antibody or antibody fragment for administration. The preferred binding protein for IGF-I herein is IGFBP-3, which is described in U.S. Pat. No. 5,258,287 and by Martin and Baxter, *J. Biol. Chem.,* 261: 8754–8760 (1986). This glycosylated IGFBP-3 protein is an acid-stable component of about 53 Kd on a non-reducing SDS-PAGE gel of a 125–150 Kd glycoprotein complex found in human plasma that carries most of the endogenous IGFs and is also regulated by GH.

The administration of the IGF binding protein with IGF-I may be accomplished by the method described in U.S. Pat. No. 5,187,151. Briefly, the IGF-I and IGFBP are administered in effective amounts by subcutaneous bolus injection in a molar ratio of from about 0.5:1 to about 3:1, preferably about 1:1.

In a further embodiment, both IGF-I and GH can be administered to the patient, each in effective amounts, or each in amounts that are sub-optimal but when combined are effective. Preferably such amounts are about 50 to 100 µg/kg/day of IGF-I and about 0.3 mg/kg/week GH. Preferably, the administration of both IGF-I and GH is by injection using, e.g., intravenous or subcutaneous means. More preferably, the administration is by subcutaneous injection for both IGF-I and GH, most preferably daily injections.

It is noted that practitioners devising doses of both IGF-I and GH should take into account the known side effects of treatment with these hormones. For GH, the side effects include sodium retention and expansion of extracellular volume (Ikkos et al., *Acta Endocrinol.* (Copenhagen), 32: 341–361 [1959]; Biglieri et al., *J. Clin. Endocrinol. Metab.,* 21: 361–370[1961]), as well as hyperinsulinemia and hyperglycemia. The major apparent side effect of IGF-I is hypoglycemia. Guler et al., *Proc. Natl. Acad. Sci. USA,* 86: 2868–2872 (1989). Indeed, the combination of IGF-I and GH may lead to a reduction in the unwanted side effects of both agents (e.g., hypoglycemia for IGF-I and hyperinsulinism for GH) and to a restoration of blood levels of GH, the secretion of which is suppressed by IGF-I.

For parenteral administration, in one embodiment, the IGF-I and GH are formulated generally by mixing each at the desired degree of purity, in a unit dosage injectable form (solution, suspension, or emulsion), with a pharmaceutically acceptable carrier, i.e., one that is non-toxic to recipients at the dosages and concentrations employed and is compatible with other ingredients of the formulation. For example, the formulation preferably does not include oxidizing agents and other compounds that are known to be deleterious to polypeptides.

Generally, the formulations are prepared by contacting the IGF-I and GH each uniformly and intimately with liquid carriers or finely divided solid carriers or both. Then, if necessary, the product is shaped into the desired formulation. Preferably the carrier is a parenteral carrier, more preferably a solution that is isotonic with the blood of the recipient. Examples of such carrier vehicles include water, saline, Ringer's solution, and dextrose solution. Non-aqueous vehicles such as fixed oils and ethyl oleate are also useful herein, as well as liposomes.

The carrier suitably contains minor amounts of additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; low molecular weight (less than about ten residues) polypeptides, e.g., polyarginine or tripeptides; proteins, such as serum albumin, gelatin, or immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, mannose, or dextrins; chelating agents such as EDTA; sugar alcohols such as mannitol or sorbitol; counterions such as sodium; and/or non-ionic surfactants such as polysorbates, poloxamers, or PEG.

The IGF-I and GH are each typically formulated individually in such vehicles at a concentration of about 0.1 mg/mL to 100 mg/mL, preferably 1–10 mg/mL, at a pH of about 4.5 to 8. Full-length IGF-I is preferably formulated at a pH about 5–6, and des(1–3)-IGF-I is preferably formulated at a pH about 3.2 to 5. GH is preferably at a pH of 7.4–7.8. It will be understood that use of certain of the foregoing excipients, carriers, or stabilizers will result in the formation of IGF-I or GH salts.

While GH can be formulated by any suitable method, the preferred formulations for GH are as follows: For met-GH (PROTROPIN® brand), the pre-lyophilized bulk solution contains 2.0 mg/mL met-GH, 16.0 mg/mL mannitol, 0.14 mg/mL sodium phosphate, and 1.6 mg/mL sodium phosphate (monobasic monohydrate), pH 7.8. The 5-mg vial of met-GH contains 5 mg met-GH, 40 mg mannitol, and 1.7 mg total sodium phosphate (dry weight) (dibasic anhydrous), pH 7.8. The 10-mg vial contains 10 mg met-GH, 80 mg mannitol, and 3.4 mg total sodium phosphate (dry weight) (dibasic anhydrous), pH.7.8.

For metless-GH (NUTROPIN® brand), the pre-lyophilized bulk solution contains 2.0 mg/mL GH, 18.0 mg/mL mannitol, 0.68 mg/mL glycine, 0.45 mg/mL sodium phosphate, and 1.3 mg/mL sodium phosphate (monobasic monohydrate), pH 7.4. The 5-mg vial contains 5 mg GH, 45 mg mannitol, 1.7 mg glycine, and 1.7 mg total sodium phosphates (dry weight) (dibasic anhydrous), pH 7.4. The 10-mg vial contains 10 mg GH, 90 mg mannitol, 3.4 mg glycine, and 3.4 mg total sodium phosphates (dry weight) (dibasic anhydrous).

Alternatively, a liquid formulation for NUTROPIN® brand hGH can be used, for example: 5.0±0.5 mg/mL rhGH; 8.8±0.9 mg/mL sodium chloride; 2.0±0.2 mg/mL Polysorbate 20; 2.5±0.3 mg/mL phenol; 2.68±0.3 mg/mL sodium citrate dihydrate; and 0.17±0.02 mg/mL citric acid anhydrous (total anhydrous sodium citrate/citric acid is 2.5 mg/mL, or 10 mM); pH 6.0±0.3. This formulation is suitably put in a 10-mg vial, which is a 2.0-mL fill of the above formulation in a 3-cc glass vial. Alternatively, a 10-mg (2.0 mL) cartridge containing the above formulation can be placed in an injection pen for injection of liquid GH to the patient.

While the IGF-I can be formulated in any way suitable for administration, the preferred formulation contains about 2–20 mg/mL of IGF-I, about 2–50 mg/mL of an osmolyte, about 1–15 mg/mL of a stabilizer, and a buffered solution at about pH 5–5.5. Preferably, the osmolyte is an inorganic salt at a concentration of about 2–10 mg/mL or a sugar alcohol at a concentration of about 40–50 mg/mL, the stabilizer is benzyl alcohol or phenol, or both, and the buffered solution is an acetic acid salt buffered solution. More preferably, the osmolyte is sodium chloride and the acetic acid salt is sodium acetate. Even more preferably, the amount of IGF-I is about 8–12 mg/mL, the amount of sodium chloride is about 5–6 mg/mL, the amount of benzyl alcohol is about 8–10 mg/mL, the amount of phenol is about 2–3 mg/mL, and the amount of sodium acetate is about 50 mM so that the pH is about 5.4. Additionally, the formulation can contain about 1–5 mg/mL of a surfactant, preferably polysorbate or poloxamer, in an amount of about 1–3 mg/mL.

In addition, the IGF-I and GH, preferably the full-length IGF-I, may be formulated together in an appropriate carrier vehicle to form a pharmaceutical composition that preferably does not contain cells. In one embodiment, the buffer used for formulation will depend on whether the composition will be employed immediately upon mixing or stored for later use. If employed immediately after mixing, a mixture of full-length IGF-I and GH can be formulated in mannitol, glycine, and phosphate, pH 7.4. If this mixture is to be stored, it is formulated in a buffer at a pH of about 6, such as citrate, with a surfactant that increases the solubility of the GH at this pH, such as 0.1% polysorbate 20 or poloxamer 188. The final preparation may be a stable liquid or lyophilized solid.

The preferred combined composition comprises IGF-I and GH in a weight ratio of IGF-I:GH of between about 1:1 and 100:1 (w/w), about 0.05–0.3 mM of an osmolyte, about 0.1–10 mg/mL of a stabilizer, about 1–5 mg/mL of a surfactant, and about 5–100 mM of a buffer at about pH 5–6. Preferably, the osmolyte is an inorganic salt and the surfactant is nonionic. More preferably, the inorganic salt is sodium chloride or potassium chloride, the stabilizer is phenol or benzyl alcohol, the surfactant is polysorbate or poloxamer, the buffer is sodium acetate or sodium citrate or both, and the amounts of IGF-I and GH are about 2–20 mg/mL and about 0.2–10 mg/mL, respectively, with the weight ratio of IGF-I:GH being between about 1:1 and 50:1. Even more preferably, the amount of IGF-I is about 5–10 mg/mL, the amount of GH is about 1–5 mg/mL, the weight ratio of IGF-I:GH is about 1:1 to 4:1, the amount of sodium chloride is about 5–7 mg/mL, the amount of phenol is about 0.1–3 mg/mL, the amount of benzyl alcohol is about 6–10 mg/mL, the surfactant is polysorbate in an amount of about 1–3 mg/mL, the amount of sodium acetate is about 2.5–4 mg/mL, and the amount of sodium citrate is about 0.1–1 mg/mL.

IGF-I and GH to be used for therapeutic administration are preferably sterile. Sterility is readily accomplished by filtration through sterile filtration membranes (e.g., 0.2 micron membranes). Therapeutic IGF-I and GH compositions generally are placed into a container having a sterile access port, for example, an intravenous solution bag or vial having a stopper pierceable by a hypodermic injection needle.

The IGF-I and GH ordinarily will be stored in unit or multi-dose containers, for example, sealed ampoules or vials, as an aqueous solution, or as a lyophilized formulation for reconstitution. As an example of a lyophilized formulation, 10-mL vials are filled with 5 mL of sterile-filtered it (w/v) aqueous IGF-I and GH solutions, and the resulting mixture is lyophilized. The infusion solution is prepared by reconstituting the lyophilized IGF-I and GH using bacteriostatic Water-for-Injection.

The invention will be more fully understood by reference to the following examples. They should not, however, be construed as limiting the scope of the invention. All literature and patent citations are expressly incorporated by reference.

EXAMPLE I

In this example, serum concentrations of GHBP were measured in a large number of samples from short children with either defined etiologies of growth failure (GHD or TS) or ISS, and were compared to GHBP levels in normal controls.

Control subjects

To establish the normal range for GHBP in serum, samples from 773 children, 366 females and 407 males, were analyzed. Ages ranged from 3 to 16 years; in some cases, age for a given subject was reported to the nearest year. The majority of the samples were obtained from a normal, school-aged population through a screening program for detection of antibodies to pancreatic β-cells (Pasco Co. School System, Fla.), and additional samples were generously provided by Dr. Juan Sotos of Children's Hospital of Columbus, Ohio and Dr. Rebecca Kirkland of Baylor College of Medicine, Houston, Tex. The children were healthy and are believed to represent a cross-section of the American population with regard to stature.

Subjects with growth retardation

Serum samples from growth-retarded children (age 1 to 17 years) were collected at baseline evaluation of 776 subjects enrolled in a post-marketing surveillance project, the NCGS. Samples were provided by 106 of the centers participating in this study.

All children with GHD and ISS included for analysis had heights that were 2 or more SDS below the mean for age and sex. Subjects were classified as having GHD by their enrolling physician. None of the children with GHD had maximum stimulated or endogenous GH levels above 10 $\mu$g/L reported by the treating physician (using an unspecified assay) or measured at Genentech Inc. using a double monoclonal immunoradiometric assay (Tandem-R HGH, Hybritech, San Diego, Calif.). Excluded are subjects with organic causes of GHD, such as central nervous system (CNS) tumors.

Patients classified as ISS in the NCGS database were either designated as such by the enrolling physician (using various terms) or had a stimulated or endogenous GH level >10 $\mu$g/L with no organic etiology of short stature indicated. Patients with TS were so identified by their enrolling physicians and include those with various forms of mosaicism. None of the subjects included had previously received any form of GH therapy.

GHBP measurements

GHBP was measured by LIFA as described above. Briefly, ninety-six-well microtiter plates (Corning Glass Works, Corning, N.Y.) were coated with a monoclonal antibody directed against GHBP (MAb 263, Agen, Australia) by incubating overnight at 4° C. with 100 $\mu$L/well of antibody at 10 $\mu$g/mL in 50 mmol/L carbonate buffer, pH 9.6. The coated wells were blocked with 150 $\mu$L PBS, pH 7.2, containing bovine serum albumin (BSA) (5 g/L) and washed. Standards (recombinant hGHBP) or samples (50 $\mu$L/well) were dispensed into the coated wells together with 50 $\mu$L/well of recombinant hGH (200 $\mu$g/L; Genentech, Inc.) and mouse immunoglobulin G (10 g/L; Fitzgerald Industries, Chelmsford, Mass.).

Plates were sealed, incubated at room temperature for 2 hr with gentle agitation, and washed before addition of a monoclonal anti-GH antibody (MAb MCB, Genentech, Inc.) conjugated to horseradish peroxidase (100 $\mu$L/well). After further incubation for 2 hours at room temperature, the plates were washed six times with wash buffer. Freshly prepared substrate solution (0.4 g of o-phenylenediamine dihydrochloride in one liter of PBS plus 0.4 mL of 30% hydrogen peroxide) was added to the plates (100 $\mu$L per well) and the incubation carried out in the dark for 15 minutes at room temperature. The reaction was stopped by the addition of 100 $\mu$L of 2.25 mol/L sulfuric acid and the absorbance at 490 nm determined. The detection range in the LIFA was 15.6 to 1000 pmol/L. The intra- and interassay coefficients of variation were approximately 7% and 11%, respectively. All samples were measured in duplicate.

GH measurements

To assess spontaneous GH secretion in the different groups, GH concentrations were measured in serum samples taken at 20-minute intervals for 12 hours (8 pm to 8 am) from 851 of the children. Mean values were calculated for each subject. GH concentrations were measured using a monoclonal antibody-based immunoradiometric assay (IRMA), with a detection limit of 0.5 $\mu$g/L (Tandem-R HGH, Hybritech).

IGF-I measurements

IGF-I concentrations were measured in serum samples taken from 858 of the children at baseline at the time of overnight GH sampling, using RIA following acid ethanol extraction (IGF-I RIA Kit, Nichols Institute, San Juan Capistrano, Calif.).

Statistical analysis

Standardized height (SDS) was calculated from age- and sex-specific mean and standard deviations derived from the National Center for Health Statistics (NCHS) normative data for American children. Hamill et al., *Am. J. Clin. Nutrition*, 32: 607–629 (1979). Body mass index (BMI) was calculated utilizing the formula: weight (kg)/[height (m)]$^2$. Mean and SD values for age, height SDS, and BMI for growth-retarded children were calculated from data reported on NCGS enrollment forms.

Means and standard deviations for GHBP concentrations (Tables I and III) and for mean 12-hour GH concentrations (Table IV) were calculated after log transformation due to the skewed nature of the data. The antilogs of the mean, mean ±2 SD (GHBP, Table I) and mean ±1 SD (GHBP, Table III, and mean 12-hr GH, Table IV) were then calculated to provide the listed values. Effects of age and sex on log GHBP concentrations in the control group were assessed by analysis of variance (ANOVA).

The calculation of standardized GHBP levels (SDS) was based on the means and associated SD's from the control subject data grouped by sex and age utilizing the equation below. For a GHBP concentration in an individual 3–15 years of age (the age range for which control samples were available), $$SDS = \frac{\log(GHBP) - \text{mean}(\log(GHBP) | \text{age, sex})}{SD(\log(GHBP) | \text{age, sex})}$$

where mean (log (GHBP)|age, sex) is the average log value of GHBP for control subjects of the same age and sex as that of the individual, and SD (log (GHBP)|age, sex) is the associated SD. After conversion to SDS, the serum GHBP concentrations in children diagnosed with GHD, ISS, and TS were compared with each other and to controls of the same sex by ANOVA. The GHBP SDS was also calculated based on bone age, rather than chronological age.

When multiple between-group comparisons on any variable were performed, Bonferroni adjustments to the p-values for statistical significance were applied to maintain an overall 0.05 level of significance for the test. Nominal p-values for the significant statistical comparisons are included in the text.

Results

The normal range (mean ±2 SD) for serum GHBP concentrations in children between 3 and 15 years of age is shown in Table I. Due to a technical problem, results are not available for children 5 years of age. Both age and sex had a significant effect on GHBP concentrations. Females had higher GHBP concentrations than males (p<0.0001). In both sexes, GHBP concentrations increased with age (p<0.0001).

TABLE I

| Sex | Age | n | Mean − 2SD | Mean | Mean + 2SD |
|---|---|---|---|---|---|
| Male | 3 | 20 | 57 | 127 | 282 |
| " | 4 | 21 | 65 | 120 | 224 |
| " | 6 | 31 | 60 | 114 | 214 |
| " | 7 | 31 | 70 | 138 | 272 |
| " | 8 | 31 | 72 | 193 | 519 |
| " | 9 | 36 | 60 | 193 | 619 |
| " | 10 | 39 | 62 | 221 | 783 |
| " | 11 | 37 | 79 | 244 | 751 |
| " | 12 | 50 | 69 | 228 | 750 |
| " | 13 | 33 | 80 | 242 | 733 |
| " | 14 | 40 | 65 | 190 | 558 |
| " | 15 | 33 | 52 | 173 | 582 |
| Female | 3 | 15 | 77 | 149 | 288 |
| " | 4 | 17 | 62 | 179 | 519 |
| " | 6 | 32 | 58 | 144 | 358 |
| " | 7 | 32 | 71 | 172 | 419 |
| " | 8 | 32 | 92 | 230 | 572 |
| " | 9 | 34 | 96 | 214 | 477 |
| " | 10 | 35 | 72 | 247 | 844 |
| " | 11 | 32 | 98 | 289 | 849 |
| " | 12 | 36 | 86 | 226 | 595 |
| " | 13 | 35 | 110 | 306 | 856 |
| " | 14 | 34 | 111 | 271 | 660 |
| " | 15 | 32 | 103 | 316 | 965 |

Normal Range for Serum GHBP Concentration (pmol/L)

Table II shows the mean (±SD) age, height SDS, and EMI for each group of subjects (height and BMI data were not available for all control subjects). Mean age was similar in all groups (approximately 11 years). Mean height SDS values were not statistically different among the GHD, ISS, and TS females or between the GHD and ISS males. Mean BMI values were significantly lower in the ISS groups compared with the other growth-retarded groups in both females (p≦0.0137) and males (p<0.0001).

TABLE II

Age, Height SDS, and BMI (mean ± SD)

| Etiology | Sex | n | Age (yr) | Height (SDS) | BMI |
|---|---|---|---|---|---|
| Control | M | 47 | 11.7 ± 2.8 | 0.3 ± 0.8 | 18.4 ± 2.9 |
| " | F | 35 | 11.6 ± 2.4 | 0.3 ± 0.8 | 19.0 ± 3.0 |
| GHD | M | 80 | 11.8 ± 3.6 | −2.9 ± 0.8 | 18.3 ± 4.5 |
| " | F | 27 | 10.8 ± 2.9 | −3.2 ± 0.9 | 17.8 ± 4.0 |
| TS | F | 96 | 11.5 ± 3.3 | −3.3 ± 0.9 | 19.1 ± 4.0 |
| ISS | M | 449 | 11.4 ± 3.4 | −2.9 ± 0.7 | 16.6 ± 2.3 |
| " | F | 124 | 10.8 ± 3.0 | −3.1 ± 0.7 | 16.4 ± 2.4 |

FIGS. 1A–1E show serum GHBP concentrations in individual children with GHD, ISS, and TS compared to the normal range for the same sex (−2 SD to +2 SD). The corresponding mean GHBP concentrations and mean SDS values in all groups are listed in Table III.

For males with either GHD or ISS, the mean GHBP SDS was lower than that of control males (both p<0.0001), and the mean SDS in males with ISS was lower than that of males with GHD (p<0.0001). The mean SDS for females with ISS and GHD was lower than that of control females (p<0.0001 and p=0.0046, respectively). In addition, the mean SDS in ISS females was lower than that in GHD females (p=0.0039). When the GHD groups were limited to subjects with maximum-stimulated GH levels ≦5 µg/L (n=23), the GHBP SDS was not significantly different from the control mean.

Because of differences in BMI between the GHD and ISS groups and the recognized relationship between BMI and GHBP levels, an analysis of covariance (ANCOVA) was performed using BMI as a covariate to determine if the between-group difference in GHBP was independent of differences in BMI. In both males and females, the differences in GHBP between the GHD and ISS groups remained significant (p<0.02).

In 91% of male ISS subjects and 92% of female ISS subjects, GHBP concentrations were below the mean for age- and sex-matched controls. The difference between ISS and GHD subjects was particularly striking in males, where 79 of 394 (20.1%) males with ISS had values >2 SDS below the mean, compared with only 6 of 69 (8.7%) males with GHD.

In contrast to the females with GHD or ISS, the mean GHBP SDS in children with TS did not differ significantly from that of control females. GHBP SDS computed for all growth-retarded groups using bone age rather than chronological age showed little difference (Table III).

TABLE III

Serum GHBP Concentrations (pmol/L)

| Etiology | Sex | n | Mean | Mean − 1 SD | Mean + 1 SD | Mean GHBP SDS$_{CA}$ (n) | Mean GHBP SDS$_{BA}$ (n) |
|---|---|---|---|---|---|---|---|
| Control | M | 407 | 183 | 103 | 326 | 0.0 (402) | n/a |
| Control | F | 366 | 228 | 133 | 394 | 0.0 (366) | n/a |
| GHD (GH < 10) | M | 80 | 146 | 86 | 250 | −0.6 (69) | −0.5 (46) |
| GHD (GH < 10) | F | 27 | 182 | 89 | 372 | −0.6 (26) | −0.5 (18) |
| GHD (GH ≦ 5) | M | 15 | 183 | 111 | 302 | 0.1 (12) | −0.2 (5) |

TABLE III-continued

Serum GHBP Concentrations (pmol/L)

| Etiology | Sex | n | Mean | Mean − 1 SD | Mean + 1 SD | Mean GHBP $SDS_{CA}$ (n) | Mean GHBP $SDS_{BA}$ (n) |
|---|---|---|---|---|---|---|---|
| GHD (GH ≦ 5) | F | 11 | 203 | 117 | 352 | −0.5 (11) | 0.1 (8) |
| TS | F | 96 | 208 | 115 | 378 | −0.3 (80) | −0.1 (61) |
| ISS | M | 449 | 103 | 63 | 166 | −1.2 (394) | −1.1 (244) |
| ISS | F | 124 | 131 | 81 | 213 | −1.2 (117) | −1.1 (67) | n/a - not available
CA - chronological age
BA - bone age

For mean GH concentrations obtained during 12-hour overnight GH sampling (Table IV), ANCOVA with etiology, sex, and age revealed that only etiology had a significant impact on the mean 12-hour GH level. As expected, the mean value in children with GHD was significantly less than in controls ($p<0.0001$). The value in girls with TS was greater than that in GHD females ($p<0.0001$) and less than that in either ISS or control females (both $p<0.002$). The mean 12-hour GH concentration in subjects with ISS was not statistically different from that in the controls. However, ISS subjects with GHBP levels >2 SD below the mean had higher mean 12-hour GH values than those with normal GHBP levels (2.8 vs. 2.3 μg/L, $p<0.005$). Mean IGF-I levels were lowest in GHD patients, and were lower than controls for ISS and TS patients.

Serum GHBP concentrations in some children with ISS are lower than those in age-matched control children. Compared with control subjects, children with GHD also had lower GHBP concentrations, but the reduction was less pronounced than in children with ISS. In girls with TS, a condition where the diagnosis is based on the presence of a chromosomal abnormality and therefore is absolute, the GHBP levels were not different from those of the control group, indicating that the GHBP levels do not simply correlate with short stature.

In addition to geographically and genetically well-defined populations with impaired peripheral GH action, such as patients with Laron syndrome and African pygmies, there may be subjects with more subtle forms of GH insensitivity, most likely representing a variety of molecular defects. In spite of the probable heterogeneity of the causes of growth retardation in children with ISS, the results above show that as a group they have reduced serum GHBP concentrations, and a significant subset (20%) have GHBP levels 2 SD or more below the normal mean for age and sex.

The children with ISS that were studied did not differ from the control group in terms of GH secretion and had significantly lower GHBP concentrations than those of the group with GHD. Patients defined as GHD, based on the arbitrary cutoff of maximum GH <10 μg/L, had lower GHBP levels than controls. However, in GHD patients with maximum GH ≦5 μg/L, mean GHBP SDS was greater than that of the GHD group with GH>5 μg/L and was not different from that of the controls.

EXAMPLE II

Figure 2:
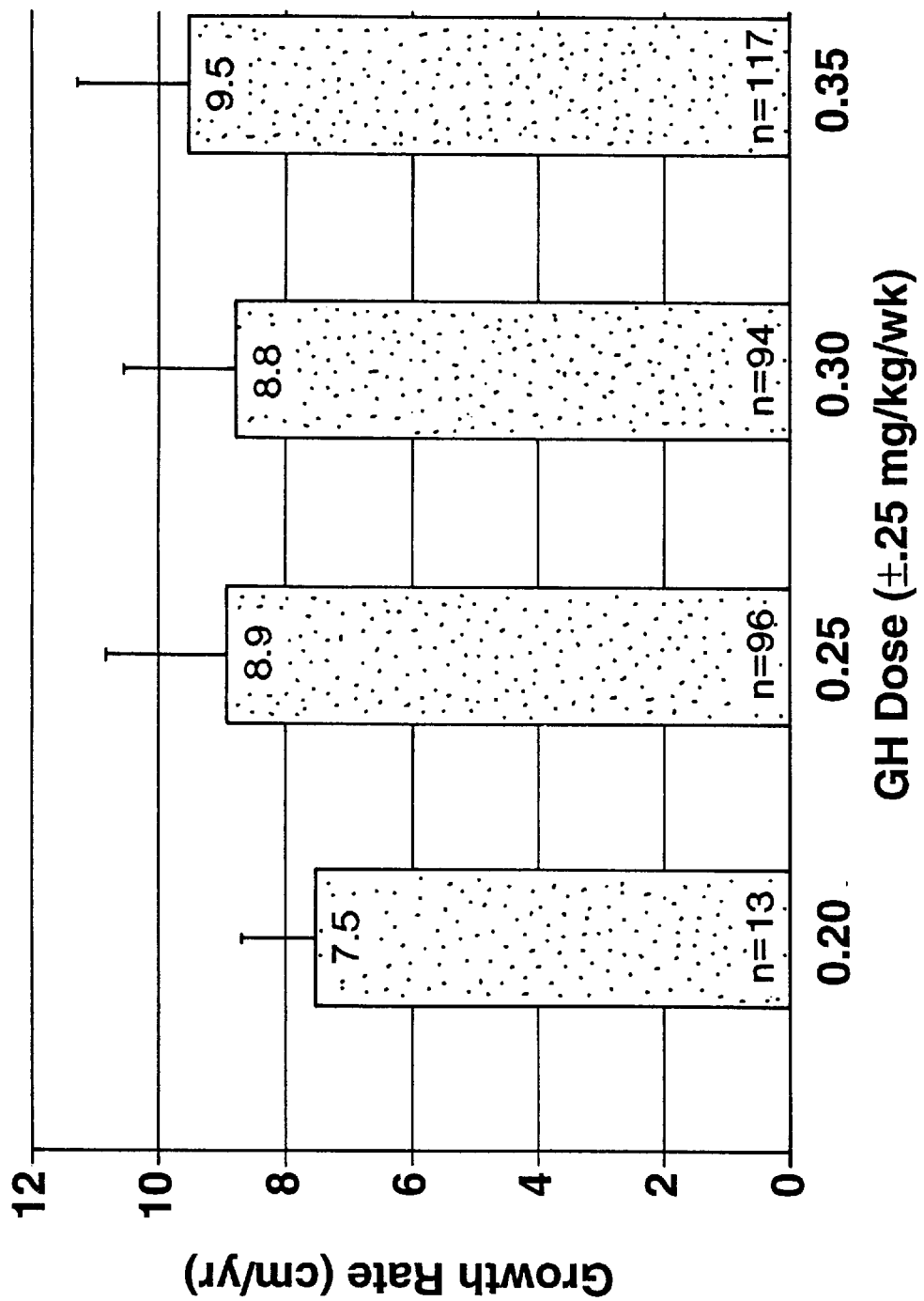
FIG. 2 shows the growth rate in cm/year of patients enrolled in the NCGS with ISS, treated with various doses of GH administered by daily injection.

Patients followed in a post-marketing surveillance study, the National Cooperative Growth Study (NCGS), were studied to compare growth rates for GHD patients with those for ISS patients treated with various doses of GH. The ISS patients include both those with normal GHBP levels and those with low GHBP levels. The results for the ISS patients, shown in FIG. 2, demonstrate that a substantially higher growth rate was obtained for children treated with 0.25±0.025 mg/kg/week of GH as compared to 0.20 mg/kg/week or less. Comparison with the GHD patients reveals that the normal doses of GH of up to 0.20 mg/kg/week were not sufficient to allow patients to have a mean growth rate range close to that seen in the GHD patients; however, doses of 0.25±0.025 mg/kg/week resulted in a mean growth rate closer to the range seen in GHD patients (about 10 cm/year). Hence, a dose of GH of greater than about 0.20 mg/kg/week is suitable for at least some patients identified by this invention.

TABLE IV

Mean 12-hour GH and IGF-I Concentrations (μg/L)

| Etiology | Sex | Mean 12-hr GH (μg/L) | | | | Extracted IGF-I (μg/L) | | | |
|---|---|---|---|---|---|---|---|---|---|
| | | n | Mean | Mean − 1 SD | Mean + 1 SD | n | Mean | Mean − 1 SD | Mean + 1 SD |
| Control | M | 47 | 2.1 | 1.2 | 3.5 | 47 | 217 | 130 | 363 |
| Control | F | 35 | 2.7 | 1.4 | 5.1 | 35 | 308 | 178 | 531 |
| GHD (GH < 10) | M | 79 | 1.4 | 0.9 | 2.1 | 80 | 99 | 41 | 238 |
| GHD (GH < 10) | F | 26 | 1.2 | 0.7 | 2.0 | 27 | 84 | 36 | 195 |
| GHD (GH ≦ 5) | M | 37 | 1.2 | 0.8 | 1.9 | 37 | 73 | 30 | 174 |
| GHD (GH ≦ 5) | F | 15 | 1.0 | 0.6 | 1.6 | 16 | 74 | 31 | 175 |
| TS | F | 96 | 1.8 | 1.0 | 3.2 | 96 | 141 | 80 | 248 |
| ISS | M | 446 | 2.2 | 1.4 | 3.4 | 449 | 108 | 51 | 231 |
| ISS | F | 122 | 2.2 | 1.3 | 3.5 | 124 | 120 | 56 | 257 |

EXAMPLE III

Patients with ISS (as defined by a maximum GH level >10 μg/L and height SDS <−2) have low GHBP levels compared to normal controls as determined by LIFA. This was not the case in short children with GHD or TS.

To assess the utility of the GHBP assay in the evaluation of short children, ISS patients were grouped according to their GHBP SDS. Patients with low GHBP SDSD defined as <−2, were compared with patients with normal GHBP levels (GHEP SDS >−2) to determine whether there was evidence of impaired sensitivity to GH treatment in the former group.

Patient Population

Serum samples were collected at 96 sites from 511 children with ISS who were subsequently treated with Protropin® brand hGH (with the mean ±SD dose of GH being 0.26±0.07 mg/kg/week by injection parenterally for patients with one-year growth data, with the particular dose and schedule of GH being at the discretion of the individual clinical investigator), and enrolled in the NCGS. To be included in this study, patients had to have a maximum stimulated GH >10 μg/L, height SDS ≦−2, and no other reported etiology of short stature. The results of the GHEP measurements were not known before the initiation of GH therapy. For analyses involving growth response while on GH treatment, only prepubertal patients were included.

Assay Methods

GHBP was assayed using the LIFA, as described in Carlsson et al., supra. Monoclonal antibodies to GHBP (MAb 263) and GH (MAb MCB) were used. GHBP values were standardized for age and sex using normative data for the LIFA based on samples provided by Dr. Thomas Merimee at University of Florida, Division of Endocrinology and Metabolism, Health Science Center, P.O. Box 100226, Gainesville, Fla. 32610-0226, and by Drs. Sotos and Kirkland mentioned above. These values have been previously reported. Carlsson et al., *J. C. E. M.*, 78: 1325–1330 (1994).

Overnight samples for GH were assayed using a double monoclonal immunoradiometric assay (Tandem-R HGH, Hybritech, San Diego, Calif.). Values reported for GH stimulation tests were measured using various GH assays.

IGF-I was measured by radioimmunoassay following acid-ethanol extraction (IGF-I by Extraction, Nichols Institute, San Juan Capistrano, Calif.) and standardized for age and sex using the normative data provided.

Statistical Methods

Heights were standardized for age and sex, and weights were standardized for height and sex using norms derived from published data for North American children. Hamill et al., *Am. J. Clin. Nutrition*, 32: 607–629 (1979). Mothers' and fathers' height SDS were calculated based on height percentiles for normal adults. Hamill et al., supra.

Multiple linear regression was used to determine which explanatory variables were linearly related to GHBP SDS, if any. In addition, subjects were divided into two groups based on their GHBP SDS (≦−2 SD and >−2 SD), to determine the significance, if any, of GHBP values that are below the normal range. The two groups were compared to each other with respect to the means or medians of several covariates (see Table VI). Univariate tests of significance between groups were performed using one of three tests: the t-test (for Gaussian-distributed variables), the Wilcoxon rank sum test (for non-Gaussian-distributed variables), or the Chi-square test (for categorical variables). To adjust for multiple comparisons, p-values <0.005 were considered statistically significant. ANCOVA was used to test for differences between the two GHBP groups after controlling for other significant variables.

Results

Patients in the low GHBP group were younger and had lower weight-for-height SDS and BMI than the normal GHBP group (Table V). The mean height SDS was −2.9 in both groups, with values ranging from −5.8 to −2.0. Approximately three-fourths of the patients were male; a similar sex distribution is seen in the total NCGS database. August et al., *J. Pediatr.*, 116: 899–903 (1990). Seventy-two percent of the patients were pre-pubertal at baseline.

TABLE V

Baseline Patient Characteristics

| | GHBP SDS ≦ −2 | | | GHBP SDS > −2 | | | |
|---|---|---|---|---|---|---|---|
| | n | mean | SD | n | mean | SD | p-value |
| Male | 80 (79%) | | | 315 (77%) | | | 0.61 |
| Female | 21 (21%) | | | 95 (23%) | | | |
| Prepubertal | 75 (78%) | | | 281 (71%) | | | 0.14 |
| Pubertal | 21 (22%) | | | 117 (29%) | | | |
| Age (yr) | 101 | 10.4 | 3.1 | 410 | 11.4 | 2.8 | 0.003 |
| Bone age (yr) | 64 | 7.8 | 3.2 | 245 | 8.9 | 3.2 | 0.015 |
| Bone age delay (yr) | 64 | 2.4 | 1.9 | 245 | 2.4 | 1.7 | 0.54 |
| Bone age SDS | 64 | −2.8 | 2.1 | 245 | −2.7 | 1.8 | 0.73 |
| Height SDS | 101 | −2.9 | 0.7 | 410 | −2.9 | 0.6 | 0.65 |
| Weight-for-Height SDS | 93 | −0.2 | 0.9 | 357 | 0.1 | 1.1 | 0.019 |
| Body mass index (kg/m²) | 100 | 15.7 | 1.6 | 410 | 16.6 | 2.2 | 0.0006 |
| Mother's height SDS | 93 | −0.9 | 1.3 | 365 | −1.1 | 1.1 | 0.27 |
| Father's height SDS | 92 | −0.7 | 1.4 | 361 | −0.6 | 1.2 | 0.57 |

There were 101 patients with GHBP SDS ≦−2 (mean −2.5) and 410 patients with GHBP SDS >−2 (mean −0.9) (Table VI). The two groups had comparable median maximum GH levels; however, these values are difficult to evaluate because of the use of various GH assays. The average for the mean 12-hour GH concentrations (using the Hybritech assay) was significantly higher in the low GHBP group, whereas the IGF-I SDS was significantly lower in that group (both p=0.0001, Table VI).

Figure 3A:
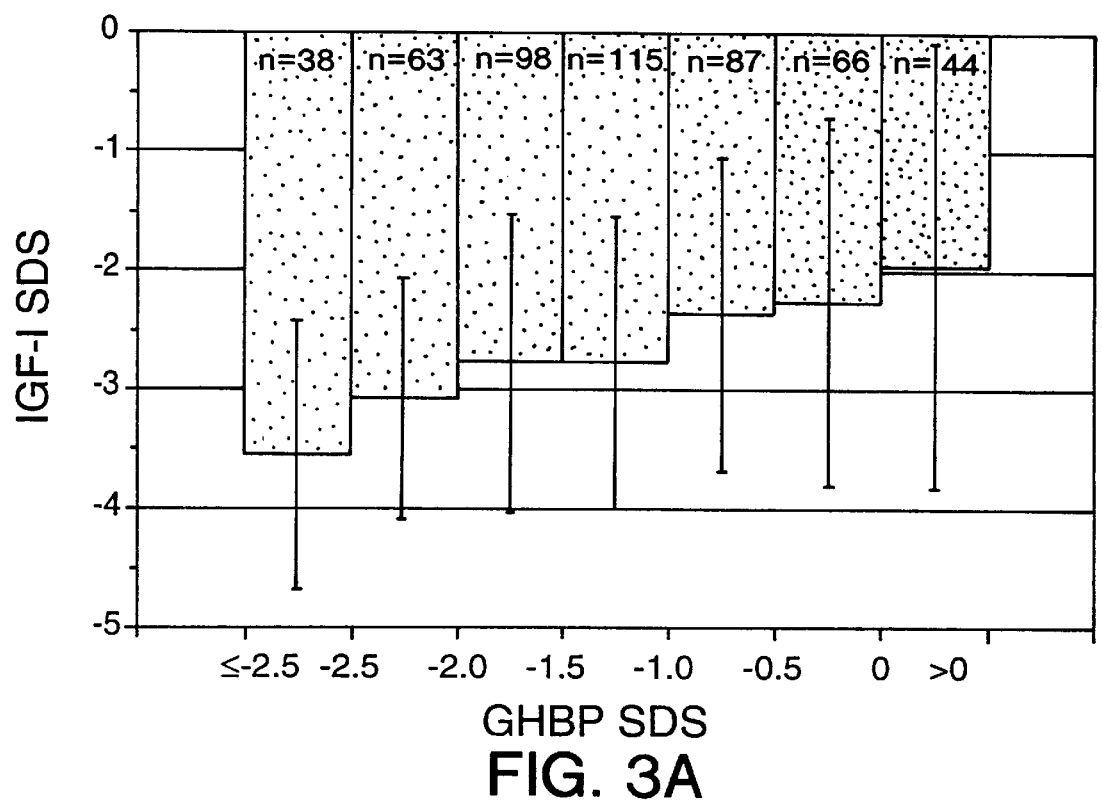
FIG. 3A depicts IGF-I concentrations, standardized for age and sex and expressed as SDS, by GHBP SDS (mean +SD).
Figure 3B:
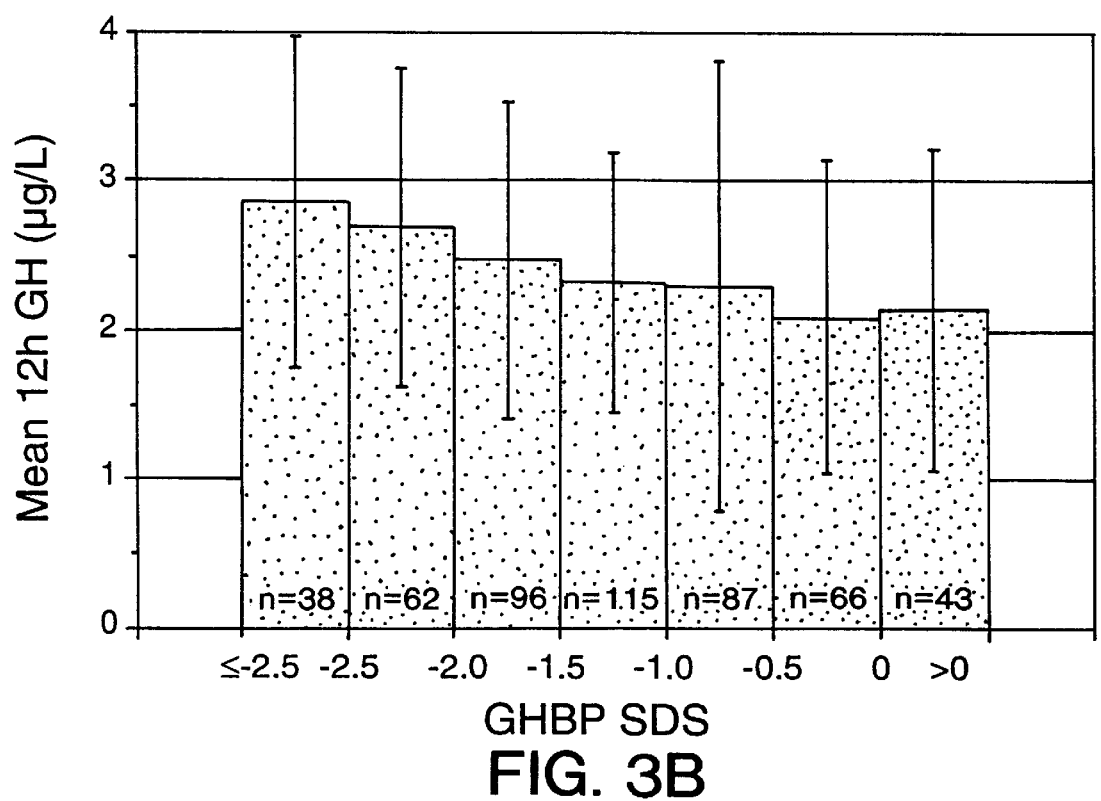
FIG. 3B depicts mean 12-hour GH concentrations from overnight sampling every 20 min for 12 hr, by GHBP SDS (mean +SD) for patients enrolled in the study used to generate FIG. 2.

FIG. 3 shows that those with low GHBP SDS had lower IGF-I SDS (FIG. 3A) and higher mean 12-hour GH levels (FIG. 3B). Among all ISS patients, GHBP SDS was positively correlated with IGF-I SDS (r=0.285, p=0.0001) and negatively correlated with mean 12-hour GH (r=−0.17, p=0.0001).

ANCOVA, controlling for differences in age, weight-for-height SDS, and mean 12-hour GH, showed that patients with GHBP SDS ≦−2 still had significantly lower IGF-I SDS than those with GHBP SDS >−2 (p=0.0001). Similarly, the low-GHBP group had significantly higher mean 12-hour GH than the normal-GHBP group (p=0.0001) after controlling for age, weight-for-height SDS, and IGF-I SDS.

TABLE VI

Baseline GHBP, IGF-I and GH Concentrations (mean ± SD)

| | GHBP SDS ≦ −2 (n = 101) | GHBP SDS > −2 (n = 410) | p-value |
|---|---|---|---|
| GHBP (pmol/L) | 60 ± 14 | 138 ± 68 | 0.0001 |
| GHBP SDS | −2.5 ± 0.4 | −0.9 ± 0.8 | 0.0001 |
| IGF-I (μg/L) | 100 ± 61 | 149 ± 101 | 0.0001 |
| IGF-I SDS | −3.3 ± 1.1 | −2.5 ± 1.4 | 0.0001 |
| Mean 12-hr GH (μg/L) | 2.8 ± 1.1 | 2.3 ± 1.1 | 0.0001 |
| Maximum GH (μg/L) | 15.7 ± 8.2 | 15.5 ± 10.0 | 0.309 |

Growth rate analyses were restricted to patients who remained prepubertal during the treatment periods considered. There were no significant linear correlations of GHBP SDS and either growth rate or change in height SDS during each of the first three years of treatment. The mean pretreatment growth rate was approximately 4 cm/yr regardless of GHBP SDS. The mean growth rate during the first year of GH therapy was approximately 8 cm/yr. FIG. 4 shows first-year growth rates for pre-pubertal patients treated with GH plotted against their GHBP SDS. There was no statistically significant correlation between the two (r=0.047, p=0.55, n=166). The figure shows that the patients who can be treated by the invention herein are those below the shaded area, provided that they also have the GH, IGF-I, and height requirements set forth as required in this subpopulation. The results indicate that the patients with low GHBP SDS levels and having the criteria of this invention responded to pharmacologic administration of GH.

Figure 6A:
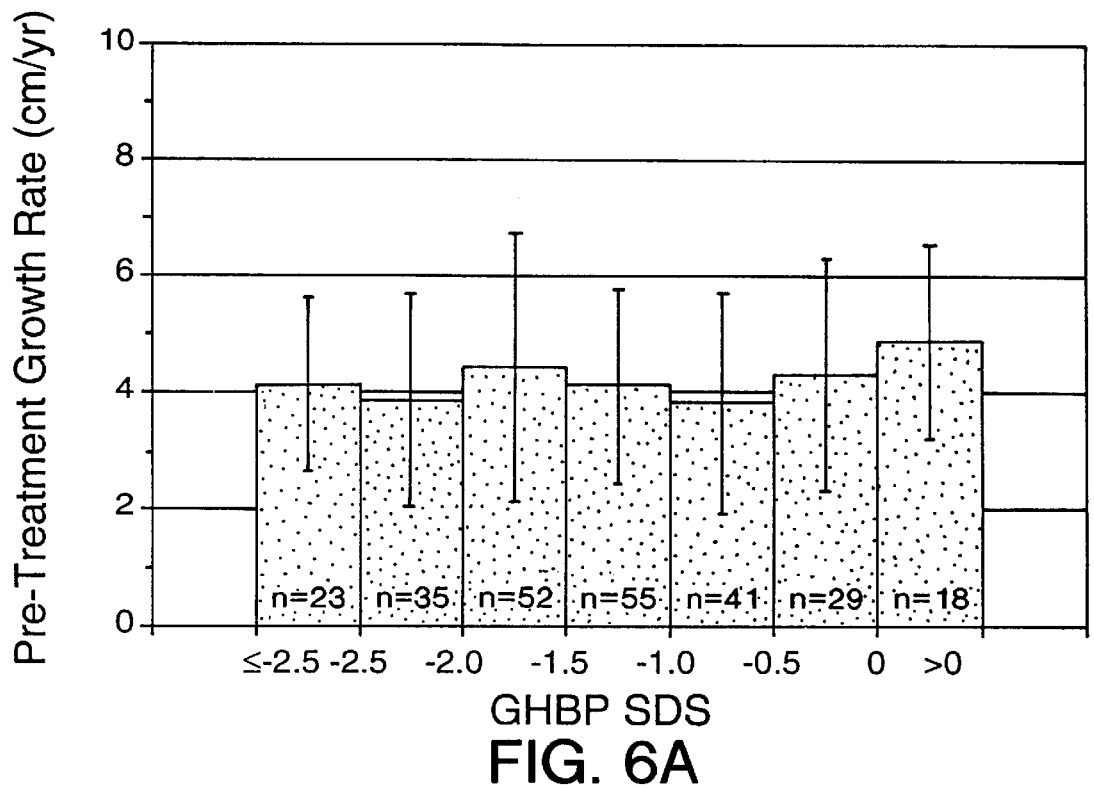
FIGS. 6A and 6B show, in bar-graph form, pre-treatment (FIG. 6A) and first-year treatment (FIG. 6B) growth rates by GHBP SDS for the patients used to generate FIG. 5.
Figure 6B:
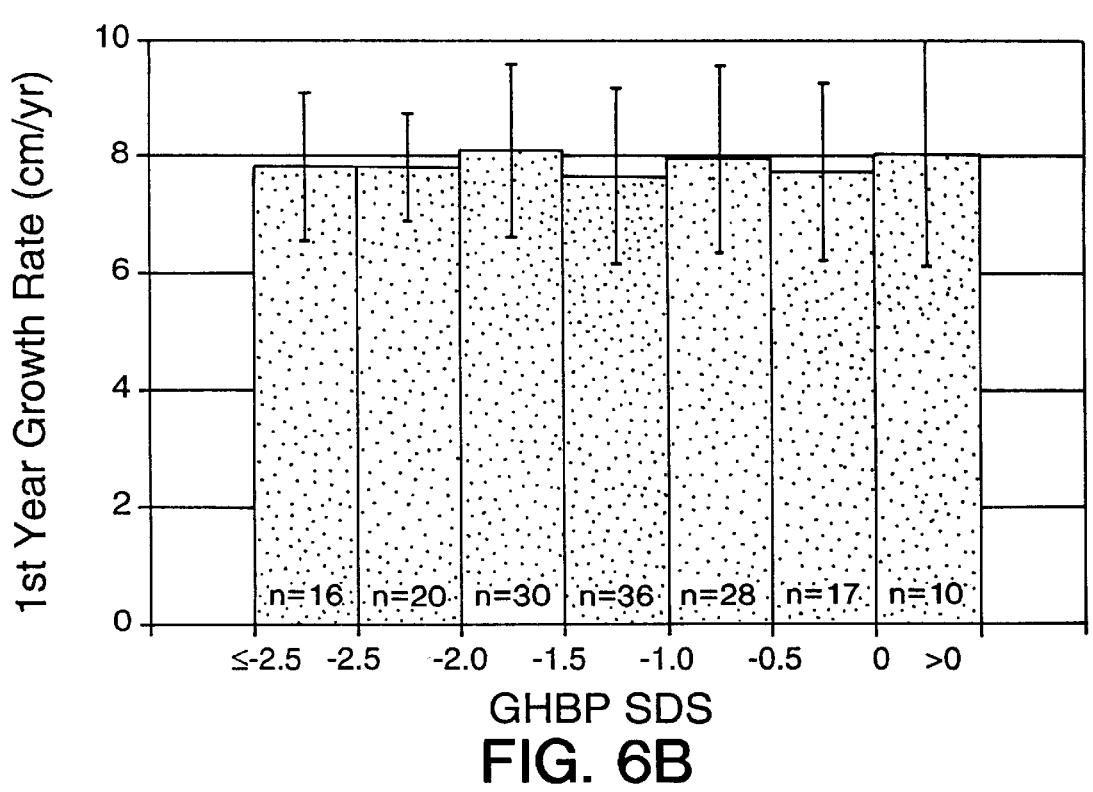

FIGS. 5 and 6 compare the pre-treatment and first-year growth rates of the patients (and in FIG. 5 also second-year growth rates). These figures show that there is a clear increase in growth in the GH-treated patients, regardless of whether the GHBP SDS of the particular patient is −2 or >−2.

Table VII shows the growth response data for the group having low GHBP SDS compared with the group having normal GHBP SDS. The two groups had similar mean GH dose and injection schedules during the first year of therapy. There were no significant differences between the groups for pretreatment growth rate or growth rates during the first four years of GH therapy. The mean change in height SDS was also not statistically different between the two groups; the mean increase in those followed for 4 years was 1.5±0.6 (n=13) in the low GHBP group and 1.7±0.6 (n=21) in the normal GHBP group.

TABLE VII

Growth Rate and Change in Height SDS from Baseline on GH Therapy in Prepubertal Patients

| | GHBP SDS ≦ −2 | | | GHBP SDS > −2 | | | |
|---|---|---|---|---|---|---|---|
| | n | mean | SD | n | mean | SD | p-value |
| 1st year GH Dose (mg/kg/wk) | 42 | 0.26 | 0.07 | 141 | 0.25 | 0.08 | 0.72 |
| 1st year GH Schedule (inj./wk) | 42 | 3.7 | 1.1 | 143 | 3.5 | 1.1 | 0.06 |
| Growth Rate (cm/yr) | | | | | | | |
| Pretreatment | 58 | 4.0 | 1.7 | 197 | 4.2 | 1.9 | 0.47 |
| 1st Year | 36 | 7.8 | 1.1 | 130 | 8.0 | 1.5 | 0.55 |
| 2nd Year | 22 | 7.2 | 1.2 | 45 | 7.0 | 1.1 | 0.80 |
| 3rd Year | 16 | 6.8 | 1.2 | 22 | 7.1 | 1.0 | 0.29 |
| 4th Year | 12 | 5.8 | 1.1 | 16 | 6.3 | 1.0 | 0.30 |
| Cumulative Δ Height SDS | | | | | | | |
| Year 1 | 45 | 0.5 | 0.2 | 145 | 0.5 | 0.3 | 0.91 |
| Years 1,2 | 28 | 1.0 | 0.4 | 67 | 0.9 | 0.4 | 0.65 |
| Years 1,2,3 | 19 | 1.30 | 0.5 | 36 | 1.3 | 0.4 | 0.70 |
| Years 1,2,3,4 | 13 | 1.5 | 0.6 | 21 | 1.7 | 0.6 | 0.24 |

Although short stature may be defined in a variety of ways, such as being below a given percentile for standard height norms, the patients in this study represent a more select group. These patients were all prescribed GH therapy, and thus went through a screening and selection process by the enrolling physicians. In addition, patients with height SDS above −2 were not included in this study. The resulting group had a mean height SDS of −2.9, mean bone age delay of 2.4 years, and mean growth rate of 4.2 cm/yr, similar to other reported patients with ISS treated with GH. Hopwood et al., *J. Pediatr.*, 123: 215–222 (1993); Albertsson-Wikland, *Acta Paediatr. Scand. Suppl.*, 343: 77–84 (1988). In this select group, it was found that some had low serum GHEP levels, after standardization for age and sex, and after adjusting for bone age. Carlsson et al., *J. C. E. M.*, 78, supra.

GHBP has been shown to be derived from the same gene as the GHR and share sequence homology with its extracellular domain. Leung et al., *Nature*, 330: 537–543 (1987). Serum GHBP levels measured using the functional assay were low or undetectable in patients with complete GHIS. Fielder et al. *J. C. E. M.*, 74: 743–750 (1992). In this example the normal range of GHBP levels in children has been determined by age and sex and it has been shown that the low GHBP levels seen in patients with ISS were significantly less than those seen in normal or GH-deficient subjects or in Turner syndrome. Carlsson et al., *J. C. E. M.*, 78, supra.

Overnight 12-hour serial sampling profiles for GH were obtained on all of the children in this study and the mean levels were normal, suggesting, without being limited to any one theory, that neurosecretory dysfunction was not present in most of the patients. The mean 12-hour GH levels showed a negative correlation with mean GHBP SDS, as has been described in normal individuals. Martha et al., *J. C. E. M.*, 73: 175–181 (1991). However, IGF-I SDS was positively correlated with GHEP SDS. Thus, the patients with lower GHBP levels had higher GH yet lower IGF-I levels, consistent with GH insensitivity.

A significant predictor of GHBP concentration is body composition, which was assessed using both BMI and weight standards for height and age. In an ANCOVA, it was found that GHBP remained a significant predictor of mean 12-hour GH and IGF-I SDS after controlling for age and weight-for-height SDS.

The growth data available for prepubertal patients enrolled in the NCGS database revealed no significant linear correlation between baseline GHEP SDS and either pretreatment growth rate or baseline height SDS. Without being limited to any one theory, one possible explanation is that growth rate and height are commonly used to select patients to be treated with GH, and thus are uniformly low in this patient population.

Figure 7:
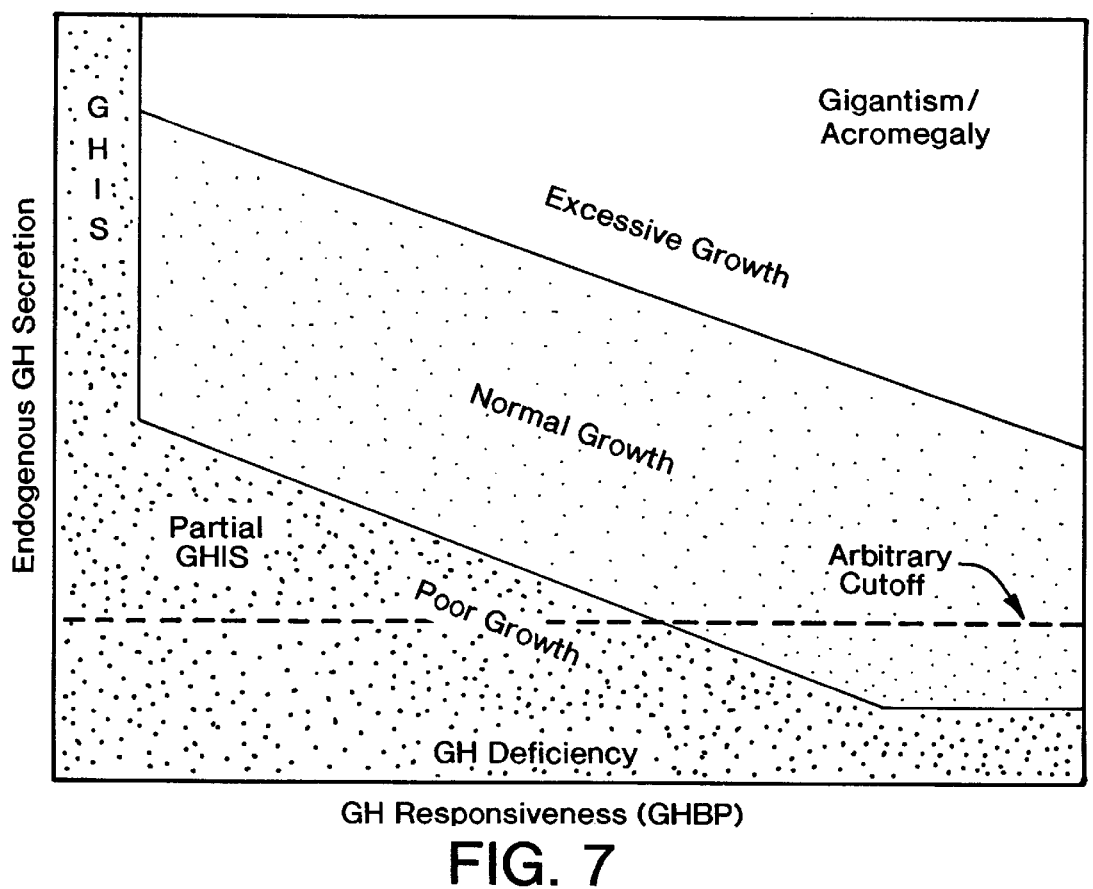
FIG. 7 shows growth status as predicted by a measure of GH secretion (e.g., stimulated or endogenous GH concentration) vs. a measure of GH responsiveness (e.g., GHBP concentration).

An interesting observation was the lack of correlation of GHBP SDS and growth response to GH therapy. Because GH secretion and GHBP levels appear to be negatively correlated in normally growing children (Martha et al., supra), a normal range can be proposed as depicted in FIG. 7. Those with excessive GH relative to their GHBP levels would be expected to have excessive growth, and those whose GH levels are too low for their GHBP levels would have poor growth. Currently, GHD is arbitrarily defined and based solely on measures of GH secretion; it is possible that some patients with GH levels above this arbitrary threshold (and within the scope of this invention) have inadequate amounts of GH relative to their low GHBP levels, resulting in poor growth. Administering exogenous GH to this subset of patients (with lower GHBP and IGF-I levels and higher mean 12-hour GH levels compared to normal, suggesting partial GH insensitivity) would be expected to raise their circulating GH to levels more appropriate for their low GHBP levels, thus overcoming their partially resistant state.

EXAMPLE IV

Introduction

The etiology of the growth failure in the majority of short children without GHD (non-GH-deficient short stature children) is poorly defined. These otherwise normal children with ISS produce normal amounts of GH in response to pharmacological stimulation, but fail to demonstrate a normal growth pattern. Lippe and Nakamoto, *Rec. Prog. Horm.*

Res., 48: 179–235 (1993). A number of GH-related defects have been proposed to account for their growth failure, including neurosecretory dysfunction (Spiliotis et al., *J. Am. Med. Assoc.*, 251: 2223–2230 [19841; Zadik et al., *Pediatrics,* 76: 355–360 [1985]), and immunologically reactive but biologically inactive GH. Kowarski et al., *J. C. E. M.,* 47: 461–464 (1978); Valenta et al., *N. Eng. J. Med.,* 31: 214–217 (1985). While these mechanisms may account for the failure to grow normally in some ISS patients, the majority do not appear to have demonstrable defects in GH secretion or function. Lanes, *Am. J. Dis. Child.,* 143: 1284–1286 (1989); Ilondo et al., *J. Clin. Endocrinol. Metab.,* 70: 1445–1451 (1990).

An alternative possibility is that ISS patients have normal secretory patterns of bioactive GH and that the defect lies in the ability of target cells to respond to GH. Such defects could lie at the level of the GHR or the mediators of GH signaling, such as IGF-I or the IGF-I receptor. Alterations in the IGF-I gene are uncommon in growth disorders. Lajara et al., *J. C. E. M.,* 70: 687–692 (1990). Resistance to GH could be due to reduction in the affinity of the GHR for GH, impaired ability to propagate a signal in response to binding GH, or to defects causing reduced cell surface receptor number. The high-affinity GHBP present in human serum is identical to the extracellular domain of the GHR and is thought to be produced from the receptor by proteolytic cleavage. Sotiropoulos et al., *Endocrinol.,* 132: 1863–1865 (1993). Immunofunctional GHBP levels (Carlsson et al., *J. C. E. M.,* 73, supra) are below the mean in 90% of ISS patients, and are more than two SDs below the mean in 20% of these children (Carlsson et al., *J. C. E. M.,* 78, supra; Mauras et al., Metabolism, 43: 357–359 [1994]). Without being limited to any one theory, it is noted that abnormalities in the GHR that reduce the amount of functional GHBP may be present in ISS patients.

A phenotype of partial GHIS in ISS is postulated by the observation in Example III that ISS patients with lower GHBP levels have lower IGF-I levels and higher mean 12-hour GH levels when compared to those with normal GHBP levels. Without being limited to any one theory, this suggests a deficiency in signaling via the GHR, leading to reduced IGF-I production and reduced negative feedback of IGF-I on GH secretion. Most ISS children respond to recombinant GH treatment with an increase in growth rate (Hopwood et al., supra); however, this response is less than that seen herein in patients with GHD (GH-deficient patients) treated with the same GH dose, once again suggesting, as one theory, a partial insensitivity to GH in ISS patients.

The high frequency of inactivating mutations in the GHR gene in complete GHIS or Laron syndrome (LS) indicates that most complete GHIS cases can be explained by lack of functional GHR. Most LS patients lack detectable GHBP activity in their blood (Baumann et al., *J. C. E. M.,* 65: 814–816 [1987]; Daughaday et al., *Proc. Natl. Acad. Sci. USA,* 84: 4636–4640 [1987]), and when measured, have no or very low levels of specific GH binding to hepatic microsomes. Eshet et al., *Isr. J. Med. Sci.,* 20: 8–11 (1984). There are 17 characterized GHR mutations associated with LS concentrated in the extracellular domain of the protein (reviewed by Rosenfeld et al., *Endocrinol. Rev.,* 15: 369–390 [1994]).

To determine if the milder phenotype of partial GHIS could be caused by less disruptive mutations in GHR, and that the reduced levels of circulating GHBP in the ISS population may serve as a marker for partial GHIS and may indicate mutations in the GHR, a subset of ISS patients with GHBP levels greater than 2 SD below the mean were selected, and the coding region of the GHR gene was analyzed for mutations. Using single-strand conformation analysis (SSCA) and sequencing of polymerase chain reaction (PCR) products with altered mobility, mutations were detected in the extracellular domain of the receptor in 4 out of 14 patients.

Subjects

Fourteen ISS patients were selected from two substudies of the NCGS with some or all of the following criteria: 1) height SDS <−2.5; 2) serum IGF-I levels below normal mean levels (measured by acid-ethanol extraction, Nichols Institute); 3) serum GH >10 $\mu$g/L on one or more provocative tests; 4) maximum serum GHBP SDS $\leq$−2 (measured by LIFA as described in Carlsson et al., *J. C. E. M.,* 73, supra, or by charcoal separation as described in Amit et al., *J. C. E. M.,* 71: 474–479 (1990]) in the case of Patient 1); 5) pre-treatment growth rate <4 cm/year; and 6) absence of underlying systemic illness. Additional information was considered if available, including mean 12-hour GH (Hybritech assay), 1st-year growth rate on GH, and IGFBP-3 levels (Endocrine Sciences). The scoring system used to select the patients from the NCGS database is shown in Table VIII. Out of a maximum score of 12, the patients scored 4–10 and all had GHBP SDS $\leq$−2. Relatives of two patients (#2 and #4) were studied to confirm the heritability of the mutations. Twenty-four normal adult volunteers whose height SDS fell within or above the normal range (−2.0 to +3.5 SDS) served as controls. The statistical significance of population differences was calculated with a Fischer Exact Test.

TABLE VIII

Criteria for Patient Selection

| Parameters | Score = 1 | Score = 2 | Score = 3 |
|---|---|---|---|
| Height SDS | < −2.5 | < 3.5 | — |
| GHBP SDS | < −2 | < −2.5 | < −3 |
| IGF-I SDS | < −2 | < −3 | < −4 |
| Max. stim. GH ($\mu$g/L) | > 10 | > 15 | > 20 |
| Pre-treatment Growth Rate (cm/yr) | < 4 | — | — |

Those patients treated with hGH (those given in Table IX who are not listed under the "GH responsive" column as "na") were injected subcutaneously with PROTROPIN® brand GH (all treated patients except Patient 2) and NUTROPIN® brand GH (Patient 2), at about 0.3 mg/kg/week for at least 6 months.

Sample Preparation and PCR Amplification

Lymphocytes were isolated from 1.5 to 10 mL of blood from each patient using either LeucoPREP Cell Separation Tubes (Becton Dickenson) or LSM Lymphocyte Separation Medium (Organon Teknika) and transformed by Epstein Barr Virus (EBV). Katz et al., *J. Infect. Dis.,* 160: 589–598 (1989). DNA was isolated from EBV-transformed lymphocytes or directly from fresh lymphocytes using the QIAamp Blood Kit (Qiagen Inc.). Genomic fragments of the GHR, specific for the coding exons 2 through 9 and their flanking splice sites, were amplified by PCR using intronic primers. The coding portion of exon 10 was amplified in three overlapping fragments in order to restrict the fragment size to less than 400 base pairs (bp). The location and sequence of the intronic primers are as follows:

| Exon | Fragment Size(bp) | Name | Sequence (5' to 3') |
|---|---|---|---|
| 2 | 154 | 101 | TCGTGGGCTTTACCTTAC (SEQ ID NO: 17) |
|  |  | 102 | CAAAACACTGAGGGTGGA (SEQ ID NO: 18) |
| 3 | 240 | 154.1 | TACACAGGGTCATATCAGATTG (SEQ ID NO: 19) |
|  |  | 154.2 | CTATTCCAGTTACTACCATCCC (SEQ ID NO: 20) |
| 4 | 188 | 105 | CTGATTTCATGCCTTGCC (SEQ ID NO: 21) |
|  |  | 106 | AGAAAGGCATGATGGTGG (SEQ ID NO: 22) |
| 5 | 286 | 107B2 | ACTTAAGCTACAACATGATT (SEQ ID NO: 23) |
|  |  | 108B1 | GCTTCCCCATTTATTTAGT (SEQ ID NO: 24) |
| 6 | 229 | 109 | ATGCTCTGTTGAATTGCAC (SEQ ID NO: 25) |
|  |  | 110 | GTGTAAGGTGTAGCAACAT (SEQ ID NO: 26) |
| 7 | 249 | 111a | GACTCTTTGGCCAATATG (SEQ ID NO: 27) |
|  |  | 112a | AAGCCAGGTTAGCTACTA (SEQ ID NO: 28) |
| 8 | 205 | 113B1 | GAAACTGTGCTTCAACTAGTC (SEQ ID NO: 29) |
|  |  | 114B1 | GGTCTAACACAACTGGTACA (SEQ ID NO: 30) |
| 9 | 179 | 115 | ATGTAGCTTTTAACATCTCAA (SEQ ID NO: 31) |
|  |  | 116 | ATGACAGGAGTCTTCAGG (SEQ ID NO: 32) |
| 10a | 311 | 117B | GAGTTTCTTTTCATAGATCTTC (SEQ ID NO: 33) |
|  |  | 8 | TTAACCTCTGTGGCTGAG (SEQ ID NO: 34) |
| 10b | 396 | 9 | ACATGAGGGTACCTCAGA (SEQ ID NO: 35) |
|  |  | 10 | CAGAAGTAGGCATTGTCC (SEQ ID NO: 36) |
| 10c | 375 | 11 | GGAAATGGTCTCACTCTG (SEQ ID NO: 37) |
|  |  | 12 | CCAAAGAAAGGCTAAGGC (SEQ ID NO: 38) |

DNA (100 ng) was amplified in 50 μL containing 0.2 mM dNTPs, 2 units Taq Polymerase (Perkin Elmer Corp.), 1.5 mM $MgCl_2$, 7 μCi $^{33}P$-α-dATP (duPont New England Nuclear), and 15 ng of each primer for 40 cycles (1 minute, 94° C.; 1 minute, 55° C.; 1 minute, 72° C. with 5 seconds added per cycle). The final cycle was followed by 1 minute 94° C. and cooling to 22° C. over 30 minutes. PCR products were electrophoresed in 2% agarose to check for contamination and to verify fragment size.

Total RNA (5–10 μg) was prepared from the EBV-transformed lymphocytes by the acid phenol method (Chomczynski and Sacchi, *Anal. Biochem.*, 162: 156–159 [1987]) and reverse transcribed (Perkin Elmer Corp., RT kit) using random primers (Promega Corp.). PCR amplification of the GHR cDNA was carried out by a nested PCR strategy. Exons 3–10 were amplified in 3 fragments. Nested primers were used to generate smaller fragments (220–415 bp). Cycle conditions were as follows: denaturation at 95° C. for 3 minutes followed by 30 cycles of 95° C., 1 minute; 55° C., 1 minute; 72° C., 1 minute; and finally 72° C. for 10 minutes. The sequences of the primers used in the nesting primer strategy were as follows:

Three RT-PCR fragments (5' to 3'):

1. C1.1 - C2.1r
    C1.1: GTCCTACAGGTATGGATCTCT (SEQ ID NO: 39)
    C3.1r: GAATATCTGCATTGCGTGGTG (SEQ ID NO: 40)
    Internal nested PCR products:
    C1.1 - C1.1r
        C1.1: GTCCTACAGGTATGGATCTCT (SEQ ID NO: 39)
        C1.1r: CTGGTATAGAACAGCTGTATG (SEQ ID NO: 41)
    ex4 - ex4.r
        ex4: ATTCTTCTAAGGAGCCTAAATTCACCA (SEQ ID NO: 42)
        ex4.r: CCACCATTGCTAGTTAGCTTG (SEQ ID NO: 43)
    ex5 - c3.1r
        ex5: ATGGACTCAAGAATGGAAAGAATG (SEQ ID NO: 44)
        c3.1r: GAATATCTGCATTGCGTGGTG (SEQ ID NO: 40)
2. C5.1 - C8
    C5.1: CACCACGCAATGCAGATATTC (SEQ ID NO: 45)
    C8: CTCATGGTCACTGCTTAGAAG (SEQ ID NO: 46)
    Internal nested PCR products:
    C5.1 - C5.1r
        C5.1: CACCACGCAATGCAGATATTC (SEQ ID NO: 45)
        C5.1r: GTTACATAGAGCACCTCACTG (SEQ ID NO: 47)
    n7 - C6.1
        n7: ATGGACCCTATATTGACAACATC (SEQ ID NO: 48)
        C6.1: CCTTTAATCTTTGGAACTGGAAC (SEQ ID NO: 49)
    C7 - C7.r
        C7: GGGCTAACAGTGATGCTATTT (SEQ ID NO: 50)
        C7.R: GCTTAGAAGTCTGTCTGTGTC (SEQ ID NO: 51)
3. C9 - C14
    C9: GCTAGATATTGATGAGCCAGA (SEQ ID NO: 52)
    C14: GCTAAGGCATGATTTTGTTCA (SEQ ID NO: 53)
    Internal nested PCR products:
    C9 - C10
        C9: GCTAGATATTGATGAGCCAGA (SEQ ID NO: 52)
        C10: GTCGATGTTTGACAGTGAACT (SEQ ID NO: 54)
    C11.1 - C12.1
        C11.1: GAAGGAGCTGAGTCAACTCAC (SEQ ID NO: 55)
        C12.1: GCTTGGCTGTATGTGTGATTC (SEQ ID NO: 56)
    C13 - C14
        C13: TACTTCTGTGAGGCAGATGCC (SEQ ID NO: 57)
        C14: GCTAAGGCATGATTTTGTTCA (SEQ ID NO: 53)

Single-Strand Conformation Analysis

SSCA was carried out on the products from each PCR reaction. 2–4 μL of the reaction mixture was mixed with an equal volume of loading buffer, denatured at 100° C. for 2 minutes and placed on ice. Samples were electrophoresed at room temperature in 0.5×MDE gels (AT Biochem Inc.) with either 1% or 10% glycerol, according to the manufacturer's instructions. Gels were dried on filter paper and autoradiographed.

DNA Sequencing

Mutations detected as aberrant bands by SSCA were confirmed by sequencing. Direct cycle sequencing of the PCR products was carried out with the amplification primers or internal (nested) primers described above and dye-terminator chemistry on the ABI373 sequencer (Applied Biosystems Division of Perkin Elmer Corp.) following standard protocols or using the Ampli-Cycle kit (Perkin Elmer Corp.) and $^{33}P$-α-dATP (duPont New England Nuclear). In addition, multiple subclones from each fragment suspected of containing a mutation were generated in M13mp19 or pBluescript KS+, sequenced with the M13-21 dye-primer, and analyzed on the ABI373 sequencer.

GH Binding Assay

To examine binding of GH to the mutant receptors, recombinant GHR extracellular domains harboring the mutations were engineered. This was done using oligonucleotide-mediated, site-directed mutagenesis, expression in E. coli, and purification. Clackson and Wells, Science, 267: 383–386 (1995); Fuh et al., J. Biol. Chem., 265: 3111–3115 (1990); Bass et al., Proc. Natl. Acad. Sci. USA, 88: 4498–4502 (1991). Affinity for GH was determined by competitive displacement of GH from the mutant receptors using radio-iodinated GH as a tracer. Spencer et al., J. Biol. Chem., 263: 7862–7867 (1988). Dissociation constants (Kds) were calculated by Scatchard analysis. Anti-GHR monoclonal antibody (Mab) 5 (Barnard et al., Endocrinology, 115: 1805 [1984]; Cunningham et al., Science, 254: 821 [1991]) was used to precipitate the GHR:GH complex. Mab 5 prevents receptor homodimerization, allowing the Kd for the initial 1:1 interaction to be determined free from the effects of dimerization. Clackson and Wells, supra; Cunningham et al., supra.

Results

Fourteen children with ISS were selected with a core score of 4 or above in the selection criteria (Table VIII). Clinical data for these patients are listed in Table IX.

(FIG. 8, allele 2 and Table X), and a cytosine to thymidine transition in exon 6, causing an arginine to a cysteine substitution at residue 161 (R161C) (FIG. 8, allele 1 and Table X). RT-PCR products spanning exons 4 through 6 were subcloned and sequenced. The two mutations were found in different subclones; thus, a mutation was found in each of the two alleles. Additionally, genetic analysis of family members indicated that the exon 4 alteration was inherited from the paternal side of the family and the exon 6 mutation from the maternal lineage. The father and paternal grandmother both exhibited the same SSCA band-shift for exon 4 as did the proband, and sequencing confirmed they both carried the identical E44K mutation. Likewise, SSCA and sequencing affirmed the presence of the exon 6 point mutation causing the R161C change in the mother and a maternal uncle. Patient 4 did not respond to exogenous GH with a significant increase in growth rate; his pretreatment growth rate was 5.5 cm/year and his growth rate on GH treatment was 5.8 cm/year.

The effects of these amino acid substitutions on the ability of the receptor to bind GH in a 1:1 complex were investi-

TABLE IX

Clinical Data for Patients Included in Study

| Pat. No. | Score | Sex | Age[1] (year) | Height SDS | GHBP SDS | IGF-I SDS | IGFBP-3 SDS | Max. Stim. GH ($\mu$g/L) | Pre-$R_x$ growth rate (cm/yr) | 1st yr growth rate (cm/yr) | GH responsive |
|---|---|---|---|---|---|---|---|---|---|---|---|
| 1 | 9 | M | 3.0 | −5.1 | ***[2] | −0.7 | na[3] | 42.0 | 2.0 | 3.0[7]–6.0[8] | yes[5,6] |
| 2 | 7 | M | 11.6 | −3.1 | ***[2] | −1.2 | na | 18.8 | 4.1 | 5.7 | yes[6] |
| 3 | 9 | M | 7.8 | −3.3 | −2.7 | −4.5 | na | 12.5 | 3.1 | 7.1 | yes[6] |
| 4 | 9 | M | 8.7 | −2.9 | −2.8 | −4.2 | −3.9 | 20.7 | 5.5 | 5.8 | no[6] |
| 5 | 9 | M | 7.8 | −3.4 | −2.6 | −3.7 | na | 48.9 | 2.9 | nc[4] | na |
| 6 | 10 | F | 14.6 | −5.5 | −2.8 | −8.2 | −5.2 | 18.0 | 2.7 | 7.8 | yes[6] |
| 7 | 7 | F | 3.5 | −3.2 | −2.6 | −2.3 | −3.5 | 19.2 | 7.1 | na | na |
| 8 | 10 | M | 9.3 | −2.5 | −2.8 | −6.1 | na | 18.7 | 2.1 | 7.2 | yes[6] |
| 9 | 7 | M | 10.0 | −3.2 | −3.0 | −2.3 | −3.3 | 20.8 | 1.2 | 7.3 | yes[6] |
| 10 | 6 | M | 7.9 | −3.2 | −2.8 | −3.0 | na | 15.6 | 4.4 | 8.4 | yes[6] |
| 11 | 4 | M | 9.8 | −1.6 | −2.3 | −2.0 | −1.3 | 19.3 | 4.2 | 9.1 | yes[6] |
| 12 | 8 | F | 7.9 | −3.1 | −2.5 | −3.5 | na | 21.6 | 6.3 | 9.0 | yes[6] |
| 13 | 8 | M | 12.8 | −3.4 | −2.3 | −4.1 | na | 16.3 | 1.5 | na | na |
| 14 | 7 | M | 8.1 | −3.5 | −2.0 | −3.2 | na | 11.7 | 3.9 | 8.3 | yes[6] |

[1]Age at enrollment into substudy;
[2]Level of GHBP at or below the limit of detection;
[3]Not available;
[4]Non-compliant;
[5]Positive IGF-I generation test;
[6]growth response with exogenous GH treatment;
[7]at a dose of 0.03 mg/kg/day;
[8]at a dose of about 0.05 mg/kg/day.

detected in the GHR locus in 24 normal adult controls, with the exception of known polymorphisms in exons 6 and 10 (Leung et al., Nature, 330: 537–543 [1987]; Godowkski et al., Proc. Natl. Acad. Sci. USA, 86: 8083–8087 [1989]). Thus, there was a significant increase in alterations in the GHR gene in ISS patients with reduced GHBP when compared to a normal population (p=0.014). Each of the genomic PCR fragments suspected of carrying a mutation was sequenced to characterize the alteration causing the aberrant band. See FIGS. 8–11. Patients 1 through 9 were also analyzed by RT-PCR (exons 3–10) and all fragments were of the predicted size, ruling out splicing alterations.

Patient 4 exhibited abnormal bands on SSCA gels when exons 4 and 6 or RT-PCR fragments covering this region were analyzed. The DNA was sequenced and the child found to be a compound heterozygote for a guanosine to adenosine transition in exon 4, introducing a lysine in place of a glutamic acid at position 44 (E44K) in the mature protein gated using mutant receptor extracellular domain expressed in E. coli. Residue E44 is involved in direct contacts with GH (deVos et al., Science, 255: 306–312 [1992]) and mutation to alanine reduced ligand binding ($Kd_{MUT}/Kd_{WT}$=17.4). Clackson and Wells, supra. It was found that introduction of a lysine at position 44 reduces binding 330-fold with respect to the wild-type receptor extracellular domain (Table X). By contrast, residue 161 is not at any intermolecular interface in the human GH:GHR complex (DeVos et al., supra), and its mutation to cysteine caused a 2.1-fold reduction in binding (Table X).

DNA from Patient 2 exhibited a SSCA bandshift with exon 5 genomic PCR fragments. DNA sequencing identified a thymidine to adenosine transversion at position 418 in the cDNA which introduced a stop codon in place of cysteine 122 (C122X). See FIG. 9. Subcloning and sequencing of multiple genomic PCR products from all exons from Patient 2 gave only the wild-type sequence, as did direct sequencing of the genomic PCR fragments. The likelihood that this patient carries a second mutation that was failed to be detected is, therefore, low. Analysis of DNA from both the mother and father of Patient 2 indicated that he inherited the stop codon mutation from his mother. During the first year of treatment with GH his growth rate increased from 4.1 cm/year to 5.7 cm/year (Table IX), indicating a response to exogenous GH. A puberty-associated growth spurt of 10.3 cm/year occurred during his second year of treatment with exogenous GH.

Patients 1 and 7 both carry heterozygous single-base-pair changes which cause amino acid alterations in the GHR from one allele. In Patient 1 an aberrant band was observed with exon 7 genomic PCR fragments. A guanosine to adenosine transition at base pair 686 caused an arginine residue to be replaced with a histidine at amino acid 211 (R211H). See FIG. 10, allele 2. Patient 1 was responsive to GH; he had a positive IGF-I generation test (baseline IGF-I was 56 µg/L and rose to a peak of 179 µg/L after four days of treatment with 0.1 unit GH/kg per injection). Furthermore, his growth rate increased from 2.0 cm/year to 3.0 cm/year on 0.03 mg GH/kg/day and 6.0 cm/year on 0.05 mg GH/kg/day (Table IX).

Patient 7 is likewise affected by an alteration in a single allele. A guanosine to cytosine transversion at base pair 726 introduces an aspartic acid in place of the wild-type glutamic acid at position 224 (E224D). See FIG. 11, allele 2. Patient 7 had never been treated with GH. Neither SSCA nor direct sequencing of the extracellular domain of the GHR detected a second alteration in either of these patients.

Residue R211 is exposed at the surface of the receptor away from any molecular interface. DeVos et al., supra. The histidine mutant produced a protein with an affinity comparable to wild-type receptor, $Kd_{MUT}/Kd_{WT}=1.4$. However, there was a striking reduction in the expression level of the mutant protein; it was expressed at a level about $10^{-4}$ that of wild-type. The arginine 211 to glycine LS-associated mutation reported by Amselem et al., Hum. Mol. Genet., 2: 355–359 (1993), results in an undetectable level of expression. A similar effect on the receptor's affinity for GH was observed for the R224D substitution (Table X). The conservative E224D substitution was not expected to perturb GH binding and, indeed, it was found that substitution with aspartic acid ($Kd_{MUT}/Kd_{WT}=1.6$) had little effect on affinity.

Conclusion

A subgroup of children with ISS have phenotypes which implicate partial GHIS in the etiology of their short stature. The hypothesis posed herein of reduced GHR signaling as exemplified by lower levels of IGF-I and higher GH concentrations with lower GHBP levels has been confirmed through the identification of GHR mutations in short, non-GH deficient patients selected for low GHBP and low IGF-I. None of 24 normal controls exhibited sequence alterations detectable by SSCA, while 4 out of 14 selected ISS patients had identifiable single-base pair alterations (p=0.014). Since SSCA is able to detect approximately 80% of known mutations in model systems (Vidal-Puig and Moller, Biotechniques, 17: 490–496 [1994]; Ravnik-Glavac et al., Hum. Mol. Genet., 3: 801–807 [1994]), there may be additional mutations present in these ISS patients which were missed.

Two of the four ISS patients with GHR mutations have responded to exogenous GH (Patients 1 and 2 of Table IX). The presence of mutations and the response to GH suggests that these patients may be partially GH insensitive due to dysfunctional GHR. Without being limited to any one theory, it is believed that the inability of Patient 4 to respond to GH most likely reflects the nature of the two mutations carried in his GHR alleles. One alteration reduces receptor affinity for GH 330-fold, presumably rendering this receptor insensitive to physiological or pharmacological levels of GH. The effect of the second alteration, R161C, is not known, but this mutation is severe; in the homozygous state it causes complete GHIS. Amselem et al., supra. The fourth patient (Patient 7) had not yet been treated with GH. It is clear from the results herein that a continuum of GH responsiveness extends from the complete GHIS seen in LS, through severely insensitive ISS patients lacking the phenotypic characteristics of LS syndrome but who may not respond to standard doses of GH, through ISS patients with partial GHIS who are responsive to standard GH therapy, and finally to the normal phenotype.

Patient 4 is a compound heterozygote for the E44K and R161C substitutions, and each parent is heterozygous for one of the two mutations. Parental and grandparental heights are all within the normal range for the adult population; however, the heights of known carriers of a single mutation are below the mean. Patient 2 is heterozygous for the

TABLE X

Mutations in the GHR Gene

| Patient | Exon | Base Change | Zygosity | Amino Acid Alteration | GH Binding $Kd_{[MabS]}$ (nM) | $Kd_{MUT}/Kd_{wt}$ |
|---|---|---|---|---|---|---|
| 1 | 7 | G - > A at 686 | het. | R211H | $0.50 \pm 0.02^1$ | 1.4 |
| 2 | 5 | T - > A at 418 | het. | C122X | nd$^2$ | nd |
| 4 | 4 | G - > A at 184 | comp. het. | E44K | $112 \pm 19$ | 330 |
| 4 | 6 | C - > T at 535 | comp. het. | R161C | $0.73 \pm 0.15$ | 2.1 |
| 7 | 7 | G - > C at 726 | het. | E224D | $0.54 \pm 0.07$ | 1.6 |

[1]Expression of this mutant receptor extracellular domain was reduced by approximately four orders of magnitude compared to wild-type.
[2]nd = not done cysteine to stop mutation at position 122 and thus has one allele producing a truncated, presumably unstable, protein. His mother carries the same mutation. Patient 2, now 19 years of age, is more severely affected by the presence of this mutation (height SDS −3.2) than his mother (height SDS −1.4). Without being limited to any one theory, the proband may have inherited a yet undefined mutation from his father (height SDS −1.4) affecting expression of the structurally normal GHR allele or another step in the GH axis. Family 2 is similar to a suspected LS patient and his unaffected mother, both of whom carried two mutations on one allele of the GHR locus. Kou et al., *J. Clin. Endocrinol. Metab.,* 76: 54–59 (1993). The similarity between this patient and Patient 2 suggests, under one theory, that both may be carriers of an unidentified second mutation, analogous to several insulin-insensitive patients in whom reduced levels of insulin receptor MRNA have been observed despite the lack of mutation in any of the exons (reviewed by Taylor et al., *Endocrine Rev.,* 13: 566–595 [1992]).

Two other patients carry heterozygous mutations leading to amino acid substitutions (R211H in Patient 1 and E224D in Patient 7). The parents of Patient 1 both had heights within the normal range for the adult population. Hamill et al., *Am. J. Clin. Nutrition,* 32: 607–629 (1979). Similarly, the father of Patient 7 has a height SDS of −0.43 and his mother's height SDS is +1.4.

LS is an autosomal recessive condition. Affected individuals usually inherit the same mutation from consanguineous parents. Heterozygotes for GHR mutations (parents and siblings of LS patients) may have mild growth abnormalities. Laron, *The Endocrinologist,* 3: 21–28 (1993); Rosenbloom et al., *Acta Paediatr.,* Suppl. 399: 125–127 (1994). Approximately half of heterozygote carriers have levels of GHBP more than 2 SDs below the mean for age. Aguirre et al., *Horm. Res.,* 34: 4–8 (1990); Laron et al., *Acta Endocrinol.,* 121: 603–608 (1989). In addition, Laron, *The Endocrinologist,* supra, reported that the heights of parents and clinically normal siblings of LS patients are typically below the 50th percentile for their sex and ethnic origin. Without being limited to any one theory, partial GHIS resulting in height SDS less than −2 may arise in carriers of heterozygous mutations of the GHR under the influence of particular genotypes at yet unidentified modifier loci, or when the alterations confer a dominant negative phenotype, as has been proposed for heterozygous insulin receptor mutations in several insulin-insensitive patients.

The five mutations identified in the four patients (E44K, C122X, R161C, R211H, E224D) are confined to the extracellular domain of the receptor. The E44K substitution causes a 330-fold reduction in affinity for GH, while alteration of the R161, R211, or E224 residues had subtle effects on ligand binding (Table X).

Residue R211 is distal to both the ligand-binding and dimerization sites of GHR. It is, however, adjacent to the 'WS-like' motif conserved throughout the cytokine receptor superfamily. Residues from the WS-like motif pack tightly with R211 and other amino acid side chains to form a stack of alternating aromatic and basic side chains.

Residue E224 corresponds to the variable residue of the WS-like motif. Like R211, it lies outside the known binding sites on the GHR molecule and mutations do not alter GH binding significantly (Table X). A E224A substitution expressed in mammalian cells in culture had altered subcellular localization. Baumgartner et al., *J. Biol. Chem.,* 269: 29094–29101 (1994). An increased fraction of the total receptor was observed in a nuclear proximal location. It is not known whether this reflects the accumulation of newly synthesized receptor or increased receptor internalization. Without being limited to any one theory, if the E224D mutation causes a similar effect, incorrect processing could result in reduced receptor numbers on the cell surface and a concomitant reduction in serum GHBP levels.

With this study it is shown that the selection of a subset of ISS children with clinical parameters suggestive of a partial insensitivity to GH identifies patients carrying GHR mutations which may affect GHR function. Since the patients studied were selected on the basis of reduced circulating functional GHBP, the mutations must affect ligand binding directly (E44K) or cause a reduction in the availability of cell surface receptor (R161C, R211H and E224D), thereby contributing to a partial GHIS syndrome. Indeed, two of the three ISS patients with GHR mutations who were treated with exogenous GH had GH-responsive partial GHIS.

EXAMPLE V

Eighty prepubertal children diagnosed as having an average height less than −2 standard deviations below normal height, a serum level of GHBP that is at least 2 standard deviations below the normal level, a serum level of IGF-I that is below the normal mean level, and a mean or maximum stimulated serum level of GH that is at least normal, aged 5–12, are treated as follows: 20 with IGF-I alone, 20 with GH alone, 20 with GH and IGF-I together, and 20 with placebo. When the drugs are given alone, the IGF-I is administered once per day by subcutaneous injection at a dose of 150 µg/kg/day and the GH is administered once per day by subcutaneous injection at a dose of 0.70 mg/kg/week. When the drugs are combined, the IGF-I is administered once per day by subcutaneous injection at a dose of 75 µg/kg/day and the GH is administered once per day by subcutaneous injection at a dose of 0.35 mg/kg/week. The IGF-I formulation is either (a) 10 mg/ml of IGF-I in 20 mM sodium acetate buffer, 2.5 mg/ml (0.25%) phenol, 45 mg/ml mannitol, pH 5.0; or (b) 10 mg/ml of IGF-I in 50 mM sodium acetate buffer, 2.5 mg/ml phenol, 5.84 mg/ml NaCl, and 9 mg/ml benzyl alcohol, pH 5.4. The GH formulation is either NUTROPIN® or PROTROPIN® brand GH available from Genentech, Inc. The patients are treated for 6 months with this protocol. The increase in height of each patient is measured.

In this study it is expected that IGF-I, GH, or the combination would increase the growth rates of all the patients as compared to those patients treated with placebo.

Alternative designs for clinical trials are as follows:

The same groups and subclass of children are treated in the same mode with GH alone at 0.35 mg/kg/week or 0.70 mg/kg/week, or IGF-I alone at 75, 100, 150, or 200 µg/kg/day. For the combination treatment, GH is used at 0.35 mg/kg/week and IGF-I at 75 or 100 µg/kg/day with or without using a placebo for comparison.

What is claimed is:

1. A method for increasing the growth rate of a human patient having partial growth hormone insensitivity syndrome comprising administering an effective amount of growth hormone to said patient, whereby said patient has a height less than about −2 standard deviations below normal for age and sex, has a serum level of high-affinity growth hormone binding protein that is at least 2 standard deviations below normal levels, has a serum level of IGF-I that is below normal mean levels, and has a mean or maximum stimulated serum level of growth hormone that is at least normal, wherein the patient does not have Laron syndrome.

2. The method of claim 1 wherein the effective amount of growth hormone is greater than about 0.2 mg/kg/week.

3. The method of claim 1 wherein the effective amount of growth hormone is greater than about 0.25 mg/kg/week.

4. The method of claim 1 wherein the effective amount of growth hormone is greater than or equal to about 0.3 mg/kg/week.

5. The method of claim 1 wherein the growth hormone is administered once per day.

6. The method of claim 5 wherein the growth hormone is administered by subcutaneous injections.

7. The method of claim 1 wherein the growth hormone is formulated at a pH of about 7.4 to 7.8.

8. A method for increasing the growth rate of a human patient having partial growth hormone insensitivity syndrome comprising administering an effective amount of IGF-I to said patient, whereby said patient has a height less than about −2 standard deviations below normal for age and sex, has a serum level of high-affinity growth hormone binding protein that is at least 2 standard deviations below normal levels, has a serum level of IGF-I that is below normal mean levels, and has a mean or maximum stimulated serum level of growth hormone that is at least normal, wherein the patient does not have Laron syndrome.

9. The method of claim 8 wherein the amount of IGF-I administered is a dose of about 50 to 240 μg/kg/day.

10. The method of claim 9 wherein the IGF-I is administered once or twice daily.

11. The method of claim 10 wherein the IGF-I is administered by subcutaneous injection.

12. The method of claim 8 wherein the IGF-I is formulated at a pH of about 5–6.

13. A method for increasing the growth rate of a human patient having partial growth hormone insensitivity syndrome comprising administering amounts of IGF-I and growth hormone to said patient which amounts are effective in combination, whereby said patient has a height less than about −2 standard deviations below normal for age and sex, has a serum level of high-affinity growth hormone binding protein that is at least 2 standard deviations below normal levels, has a serum level of IGF-I that is below normal mean levels, and has a mean or maximum stimulated serum level of growth hormone that is at least normal, wherein the patient does not have Laron syndrome.

14. The method of claim 13 wherein the IGF-I and growth hormone are together administered by subcutaneous injections.

15. A method for increasing the growth rate of a human patient with non-GH-deficient short stature but not Laron syndrome comprising detecting whether the patient has a height less than about −2 standard deviations below normal for age and sex, has a serum level of high-affinity growth hormone binding protein that is at least 2 standard deviations below normal levels, has a serum level of IGF-I that is below normal mean levels, and has a mean or maximum stimulated serum level of growth hormone that is at least normal, and, if so, administering an effective amount of growth hormone that increases the growth rate of the patient to said patient.

16. A method for increasing the growth rate of a human patient with non-GH-deficient short stature but not Laron syndrome comprising detecting whether the patient has a height less than about −2 standard deviations below normal for age and sex, has a serum level of high-affinity growth hormone binding protein that is at least 2 standard deviations below normal levels, has a serum level of IGF-I that is below normal mean levels, and has a mean or maximum stimulated serum level of growth hormone that is at least normal, and, if so, administering an effective amount of IGF-I to said patient.

* * * * *

UNITED STATES PATENT AND TRADEMARK OFFICE
CERTIFICATE OF CORRECTION

PATENT NO. : 5,824,642
DATED : October 20, 1998
INVENTOR(S) : ATTIE et al.

It is certified that error appears in the above-identified patent and that said Letters Patent is hereby corrected as shown below:

On the cover page, immediately preceding [21] Appl. No.: 468,580, insert a new paragraph to read --The term of this patent shall not extend beyond the expiration date of Pat. No. 5,646,113.--

Signed and Sealed this

Twenty-fifth Day of May, 1999

Attest:

Q. TODD DICKINSON

Attesting Officer

Acting Commissioner of Patents and Trademarks